(12) United States Patent
Gangjee et al.

(10) Patent No.: US 10,793,573 B2
(45) Date of Patent: Oct. 6, 2020

(54) FIRST-IN-CLASS OF SHMT2 AND MTHFD2 INHIBITORS AS ANTITUMOR AGENTS

(71) Applicants: Duquesne University of the Holy Spirit, Pittsburgh, PA (US); Wayne State University, Detroit, MI (US)

(72) Inventors: Aleem Gangjee, Allison Park, PA (US); Larry H. Matherly, Novi, MI (US)

(73) Assignees: Duquesne University of The Holy Spirit, Pittsburgh, PA (US); Wayne State University, Detroit, MI (US)

( * ) Notice: Subject to any disclaimer, the term of this patent is extended or adjusted under 35 U.S.C. 154(b) by 0 days.

(21) Appl. No.: 16/118,007

(22) Filed: Aug. 30, 2018

(65) Prior Publication Data

US 2019/0100524 A1 Apr. 4, 2019

Related U.S. Application Data

(60) Provisional application No. 62/552,432, filed on Aug. 31, 2017.

(51) Int. Cl.
*A61K 31/519* (2006.01)
*C07D 487/04* (2006.01)
*A61P 35/00* (2006.01)

(52) U.S. Cl.
CPC .......... *C07D 487/04* (2013.01); *A61K 31/519* (2013.01); *A61P 35/00* (2018.01)

(58) Field of Classification Search
CPC ............................ A61K 31/519; C07D 487/04
USPC ....................................... 514/265.1; 544/280
See application file for complete search history.

(56) References Cited

U.S. PATENT DOCUMENTS

| 5,554,615 A | 9/1996 | Nomura et al. |
| 6,686,365 B2 | 2/2004 | Riebesehl et al. |
| 2016/0032401 A1 | 2/2016 | Jain et al. |
| 2016/0317539 A1 | 11/2016 | Cho et al. |

OTHER PUBLICATIONS

Taylor, et. al.; J. Org. Chem., 1995, 60, 7947-7952.*
PubChem-Compound Summary for : CID 60843, Pemetrexed, https://pubchem.ncbi.nlm.nih.gov/compound/60843> (Aug. 8, 2005).
PubChem-Compound Summary for : CID 10094027, JLGHPSYFXSLUDR-AWEZNQCLSA-N, https://pubchem.ncbi.nlm.nih.gov/compound/10094027> (Oct. 25, 2006).
PCT International Search Report and Written Opinion for PCT/US18/48905, filed Aug. 30, 2018, dated Dec. 26, 2018.
Hanahan, D. et al., Hallmarks of Center: The Next Generation, Cell, 2011, pp. 646-674, Elsevier Inc.
Newman, A.C. et al., One-carbon metabolism in cancer, British Journal of Cancer, 2017, pp. 1499-1504, Springer Nature.

Yang, M. et al., Serine and one-carbon metabolism in cancer, www.nature.com/nrc, 2016, pp. 650-662, vol. 16, Macmillan Publishers Limited.
Ducker, G.S. et al., One-Carbon Metabolism in Health and Disease, Cell Metabolism, 2017, pp. 27-42, Elsevier Inc.
Tibbetts, A.S. et al., Compartmentalization of Mammalian Folate-Mediated One-Carbon Metabolism, Annual Review of Nutrition, 2010, pp. 57-81, Annual Reviews.
Chattopadhyay, S. et al., Pemetrexed: biochemical and cellular pharmacology, mechanisms, and clinical applications, Molecular Cancer Therapeutics, 2007, pp. 404-417, American Association for Cancer Research.
Matherly, L.H. et al., The Major Facilitative Folate Transporters Solute Carrier 19A1 and Solute Carrier 46A1: Biology and Role in Antifolate Chemotherapy of Cancer, Drug Metabolism and Disposition, 2014, pp. 632-649, The American Society.
Visentin, M. et al., The Antifolates, Hematol Oncol Clin North Am., 2012, pp. 1-23, Elsevier Inc.
Matherly, L.H. et al., Human reduced folate carrier: translation of basic biology to cancer etiology and therapy, Cancer Metastasis Rev, 2007, pp. 111-128, Springer Science.
Zhao, R. et al., Mechanisms of Membrane Transport of Folates into Cells and Across Epithelia, Annu Rev Nutr., 2011, pp. 1-31, Annual Reviews.
McCarthy, E.A. et al., A Mutation Inactivating the Mitochondrial Inner Membrane Folate Transporter Creates a Glycine Requirement for Survival of Chinese Hamster Cells, The Journal of Biological Chemistry, 2004, pp. 33829-33836, vol. 279, The American Society.
Lawrence, S.A. et al., Tetrahydrofolate Recognition by the Mitochondrial Folate Transporter, The Journal of Biological Chemistry, 2011, pp. 31480-31489, vol. 286, The American Society.

(Continued)

*Primary Examiner* — Jeffrey H Murray
(74) *Attorney, Agent, or Firm* — Buchanan Ingersoll & Rooney PC; Craig G. Cocheour, Esq.

(57) ABSTRACT

A compound of the Formula I and optionally a pharmaceutically acceptable salt thereof is provided:

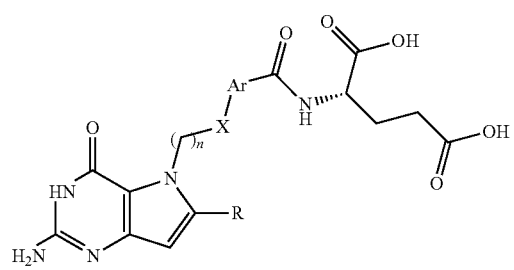

Formula I, wherein, R is one selected from the group consisting of H and $CH_3$;
n is an integer ranging from 1 to 4; X is one selected from the group consisting of $-CH_2-$, O, S, $-NH-$, $-NHCHO-$, $-NHCOCH_3-$, and $-NHCOCF_3-$; and Ar is one selected from the group consisting of (a) 1,4-phenyl, (b) 2'-fluoro-1,4-phenyl, and (c) 2,5-thienyl. Methods of treating a patient having cancer, targeting mitochondrial metabolism, and targeting SHMT2 and MTHFD2 using the compounds of this invention are disclosed.

1 Claim, 16 Drawing Sheets

(56) References Cited

OTHER PUBLICATIONS

Lawrence, S.A. et al., Mammalian Mitochondrial and Cytosolic Folylpolyglutamate Synthetase Maintain the Subcellular Compartmentalization of Folates, The Journal of Biological Chemistry, 2014, pp. 29386-29396, vol. 289, JBC Papers in Press.

Jain, M. et al., Metabolite Profiling Identifies a Key Role for Glycine in Rapid Cancer Cell Proliferation, www.sciencemag.org, 2012, pp. 1040-1044, vol. 336, American Association for the Advancement of Science.

Kim, D. et al., SHMT2 drives glioma cell survival in ischaemia but imposes a dependence on glycine clearance, Nature, 2015, pp. 363-367, vol. 520, Macmillan Publishers Limited.

Nilsson, R. et al., Metabolic enzyme expression highlights a key role for MTHFD2 and the mitochondrial folate pathway in cancer, Nature Communications, 2014, pp. 1-10, Macmillan Publishers Limited.

Zhang, L. et al., Prognostic and therapeutic value of mitochondrial serine hydroxyl-methyltransferase 2 as a breast cancer biomarker, Oncology Reports, 2016, pp. 2489-2500.

Loayza-Puch, F. et al., Tumour-specific proline vulnerability uncovered by differential ribosome codon reading, Nature, 2016, pp. 490-494, vol. 530, Macmillan Publishers Limited.

Ye, J. et al., Serine Catabolism Regulates Mitochondrial Redox Control during Hypoxia, Cancer Discovery, 2014, pp. 1406-1417, American Association for Cancer Research.

Ducker, G.S. et al., Reversal of Cytosolic One-Carbon Flux Compensates for Loss of the Mitochondrial Folate Pathway, Cell Metabolism, 2016, pp. 1140-1153, Elsevier Inc.

Ducker, G.S. et al., Human SHMT inhibitors reveal defective glycine import as a targetable metabolic vulnerability of diffuse large B-cell lymphoma, PNAS, 2017, pp. 11404-11409, vol. 114.

Lee, G.Y. et al., Comparative Oncogenomics Identifies PSMB4 and SHMT2 as Potential Cancer Driver Genes, Cancer Research, 2014, pp. 3114-3126, American Association for Cancer Research.

Deng, Y. et al., Synthesis and Discovery of High Affinity Folate Receptor-Specific Glycinamide Ribonucleotide Formyltransferase Inhibitors with Antitumor Activity, Journal of Medicinal Chemistry, 2008, pp. 5052-5063, vol. 51, American Chemical Society.

Deng, Y. et al., Synthesis and Biological Activity of a Novel Series of 6-Substituted Thieno[2,3-d]pyrimidine Antifolate Inhibitors of Purine Biosynthesis with Selectivity for High Affinity Folate Receptors over the Reduced Folate Carrier and Proton-Coupled Folate Transporter for Cellular Entry, Journal of Medicinal Chemistry, 2009, pp. 2940-2951, vol. 52, American Chemical Society.

Golani, L.K. et al., Tumor Targeting with Novel 6-Substituted Pyrrolo [2,3-d] Pyrimidine Antifolates with Heteroatom Bridge Substitutions via Cellular Uptake by Folate Receptor α and the Proton-Coupled Folate Transporter and Inhibition of de Novo Purine Nucleotide Biosynthesis, Journal of Medicinal Chemistry, 2016, pp. 7856-7876, vol. 59, American Chemical Society.

Mitchell-Ryan, S. et al., Discovery of 5-Substituted Pyrrolo[2,3-d]pyrimidine Antifolates as Dual-Acting Inhibitors of Glycinamide Ribonucleotide Formyltransferase and 5-Aminoimidazole-4-carboxamide Ribonucleotide Formyltransferase in De Novo Purine Nucleotide Biosynthesis: Implications of Inhibiting 5-Aminoimidazole-4-carboxamide Ribonucleotide Formyltransferase to AMPK Activation and Antitumor Activity, Journal of Medicinal chemistry, 2013, pp. 10016-10032, vol. 56, American Chemical Society.

Wang, L. et al., Synthesis, Biological, and Antitumor Activity of a Highly Potent 6-Substituted Pyrrolo[2,3-d]pyrimidine Thienoyl Antifolate Inhibitor with Proton-Coupled Folate Transporter and Folate Receptor Selectivity over the Reduced Folate Carrier That Inhibits β-Glycinamide Ribonucleotide Formyltransferase, Journal of Medicinal Chemistry, 2011, pp. 7150-7164, vol. 54, American Chemical Society.

Wang, Y. et al., Novel 5-Substituted Pyrrolo[2,3-d]pyrimidines as Dual Inhibitors of Glycinamide Ribonucleotide Formyltransferase and 5-Aminoimidazole-4-carboxamide Ribonucleotide Formyltransferase and as Potential Antitumor Agents, Journal of Medicinal Chemistry, 2015, pp. 1479-1493, vol. 58, American Chemical Society.

Ravindra, M. et al., Fluorine-Substituted Pyrrolo[2,3-d]Pyrimidine Analogues with Tumor Targeting via Cellular Uptake by Folate Receptor α and the Proton-Coupled Folate Transporter and Inhibition of de Novo Purine Nucleotide Biosynthesis, Journal of Medicinal Chemistry, 2018, pp. 4228-4248, vol. 61, American Chemical Society.

Flintoff, W.F. et al., Isolation and Partial Characterization of Three Methotrexate-Resistant Phenotypes from Chinese Hamster Ovary Cells, Somatic Cell Genetics, 1976, pp. 245-261, vol. 2, Plenum Publishing Corporation.

Desmoulin, S.K. et al., The human proton-coupled folate transporter, Biology and Therapeutic Applications to Cancer; Cancer Biology & Therapy, 2012, pp. 1355-1373, Landes Bioscience.

Fu, T. et al., Location of the Pteroylpolyglutamate-binding Site on Rabbit Cytosolic Serine Hydroxymethyltransferase, The Journal of Biological Chemistry, 2003, pp. 2645-2653, vol. 278, The American Society.

Wilson, M.R. et al., Targeting Nonsquamous Nonsmall Cell Lung Cancer via the Proton-Coupled Folate Transporter with 6-Substituted Pyrrolo [2,3-d]Pyrimidine Thienoyl Antifolates, Molecular Pharmacology, 2016, pp. 425-434, The American Society.

Desmoulin, S.K. et al., Therapeutic Targeting of a Novel 6-Substituted Pyrrolo [2,3-d]pyrimidine Thienoyl Antifolate to Human Solid Tumors Based on Selective Uptake by the Proton-Coupled Folate Transporter, Molecular Pharmacology, 2011, pp. 1096-1107, vol. 80, The American Society.

Altschul, S.F. et al., Protein database searches using compositionally adjusted substitution matrices, FEBS Journal, 2005, pp. 5101-5109, FEBS.

Cheong, C. et al., Crystal Structures of Human Bifunctional Enzyme Aminoimidazole-4-carboxamide Ribonucleotide Transformylase/ IMP Cyclohydrolase in Complex with Potent Sulfonyl-containing Antifolates, The Journal of Biological Chemistry, 2004, pp. 18034-18045, vol. 279, The American Society.

Deis, S.M. et al., Structural and Enzymatic Analysis of Tumor-Targeted Antifolates That Inhibit Glycinamide Ribonucleotide Formyltransferase, Biochemistry, 2016, pp. 4574-4582, American Chemical Society.

Morscher, R.J. et al., Mitochondrial translation requires folate-dependent tRNA methylation, Nature, 2018, pp. 128-132, vol. 554, Macmillan Publishers Limited.

Minton, D.R. et al., Serine Catabolism by SHMT2 Is Required for Proper Mitochondrial Translation Initiation and Maintenance of Formylmethionyl-tRNAs, Molecular Cell, 2018, pp. 610-621, Elsevier Inc.

Gangjee, A. et al., Design, Synthesis, and Biological Evaluation of Classical and Nonclassical 2-Amino-4-oxo-5-substituted-6-methylpyrrolo[3,2-d]pyrimidines as Dual Thymidylate Synthase and Dihydrofolate Reductase Inhibitors, Journal of Medicinal Chemistry, 2008, pp. 68-76, vol. 51, American Chemical Society.

Wong, S.C. et al., Isolation of Human cDNAs That Restore Methotrexate Sensitivity and Reduced Folate Carrier Activity in Methotrexate Transport-defective Chinese Hamster Ovary Cells, The Journal of Biological Chemistry, 1995, pp. 17468-17475, vol. 270, The American Society.

Lowry, O.H. et al., Protein Measurement With the Folin Phenol Reagent, J. Biol. Chem., 1951, pp. 265-275.

Laemmli, U.K., Cleavage of Structural Proteins during the Assembly of the Head of Bacteriophage T4, Nature, 1970, pp. 680-685, vol. 227, Nature Publishing Group.

Matsudaira, P., Sequence from Picomole Quantities of Proteins Electroblotted onto Polyvinylidene Difluoride Membranes, The Journal of Biological Chemistry, 1987, pp. 10035-10038, vol. 262, The American Society of Biological Chemists, Inc.

Cherian, C. et al., Therapeutic targeting malignant mesothelioma with a novel 6-substituted pyrrolo[2,3-d]pyrimidine thienoyl antifolate via its selective uptake by the proton-coupled folate transporter, Cancer Chemother Pharmacol, 2013, pp. 999-1011, Springer.

Wang, L. et al., Synthesis and Antitumor Activity of a Novel Series of 6-Substituted Pyrrolo[2,3-d]pyrimidine Thienoyl Antifolate Inhibi-

(56) References Cited

OTHER PUBLICATIONS tors of Purine Biosynthesis with Selectivity for High Affinity Folate Receptors and the Proton-Coupled Folate Transporter over the Reduced Folate Carrier for Cellular Entry, Journal of Medicinal Chemistry, 2010, pp. 1306-1318, vol. 53, American Chemical Society.

Wang, L. et al., 6-Substituted Pyrrolo[2,3-d]pyrimidine Thienoyl Regioisomers as Targeted Antifolates for Folate Receptor α and the Proton-Coupled Folate Transporter in Human Tumors, Journal of Medicinal Chemistry, 2015, pp. 6938-6959, American Chemical Society.

Verela-Moreiras, G. et al., Long-Term Folate Deficiency Alters Folate Content and Distribution Differentially in Rat Tissues, Nutrient Requirements and Interactions, 1992, pp. 986-991, American Institute of Nutrition.

Kotake, Y. et al., Synthesis and Antitumor Activities of Novel 6-5 Fused Ring Heterocycle Antifolates: N-[4-[ω-(2-Amino-4-substituted-6,7-dihydrocyclopenta[d]pyrimidin-5-yl)alkyl]benzoyl]-L-glutamic Acids, Journal of Medicinal Chemistry, 1994, pp. 1616-1624, vol. 37, American Chemical Society.

Guan, Y. et al., Catalytic Asymmetric Synthesis of Alkynyl Aziridines: Both Enantiomers of cis-Aziridines from One Enantiomer of the Catalyst, Chemistry A European Journal, 2014, pp. 13894-13900, Wiley.

Golani, L.K. et al., Structure-Activity Profiles of Novel 6-Substituted Pyrrolo[2,3-d]pyrimidine Thienoyl Antifolates with Modified Amino Acids for Cellular Uptake by Folate Receptors α and β and the Proton-Coupled Folate Transporter, Journal of Medicinal Chemistry, 2014, pp. 8152-8166, American Chemical Society.

Gangjee, A. et al., Synthesis of Classical, Three-Carbon-Bridged 5-Substituted Furo[2,3-d]pyrimidine and 6-Substituted Pyrrolo[2,3-d]pyrimidine Analogues as Antifolates, Journal of Medicinal Chemistry, 2004, pp. 6893-6901, vol. 47, American Chemical Society.

Rondla, N.R. et al., Palladium-Catalyzed C—Cn Activation for Intramolecular Cyanoesterification of Alkynes, Organic Letters, 2011, pp. 1940-1943, vol. 13, American Chemical Society.

de Leseleuc, M. et al, Direct synthesis of macrodiolides via hafnium(iv) catalysis, Chem. Commun., 2015, pp. 10471-10474, The Royal Society of Chemistry.

\* cited by examiner

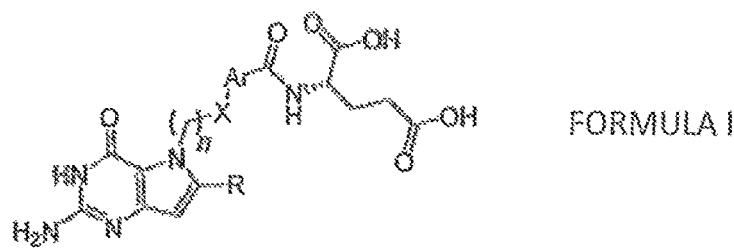

1 n = 1, 3-4; R = H; X = CH$_2$; Ar = 1,4-phenyl or 2,5-thienyl
2 n = 1-4; R = CH$_3$; X = CH$_2$; Ar = 1,4-phenyl or 2,5-thienyl
3 n = 2-4; R = H; X = O, S, NH, NHCHO, NHCOCH$_3$, NHCOCF$_3$; Ar = 1,4-phenyl or 2,5-thienyl

AGF291 n = 2, Ar = 1,4-phenyl, R = H, X = CH$_2$
AGF300 n = 3, Ar = 1,4-phenyl, R = H, X = CH$_2$
AGF307 n = 4, Ar = 1,4-phenyl, R = CH$_3$, X = CH$_2$
AGF312 n = 3, Ar = 1,4-phenyl, R = CH$_3$, X = CH$_2$
AGF318 n = 3, Ar = 2,5-thienyl, R = H, X = CH$_2$
AGF320 n = 4, Ar = 2,5-thienyl, R = H, X = CH$_2$
AGF323 n = 3, Ar = 1,4-phenyl, R = H, X = O
AGF331 n = 2, Ar = 2,5-thienyl, R = H, X = CH$_2$

FORMULA I

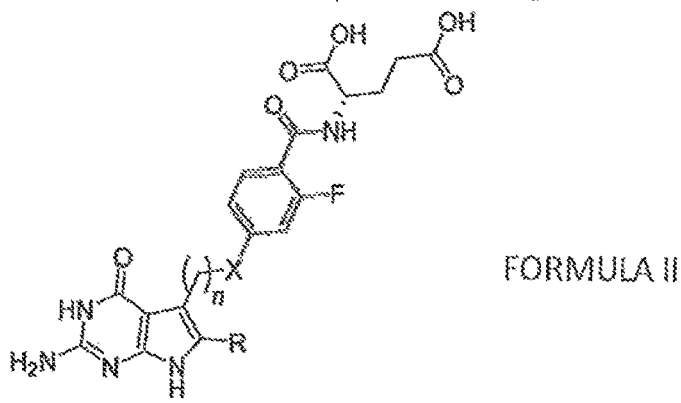

4 n = 1-2, 4; R = H; X = CH$_2$
5 n = 1-4; R = CH$_3$; X = CH$_2$
6 n = 1-4; R = H; X = O, S, NH, NHCHO, NHCOCH$_3$, NHCOCF$_3$
AGF287 n = 3, R = H, X = CH$_2$

FORMULA II

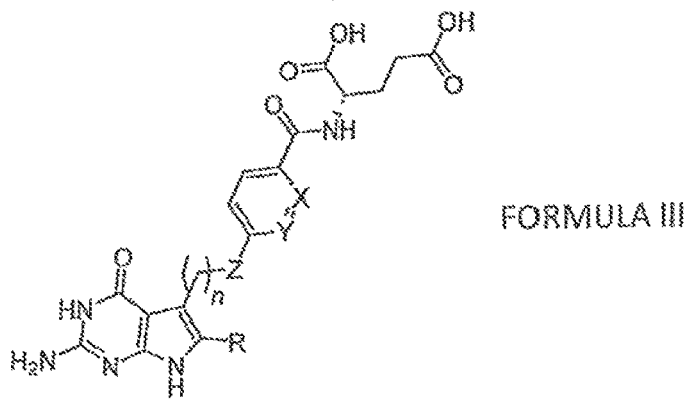

7 n = 1-4; R = H; X = N; Y = CH; Z = CH$_2$, O, S, NH, NHCHO, NHCOCH$_3$, NHCOCF$_3$
8 n = 1-4; R = H; X = CH; Y = N; Z = CH$_2$, O, S, NH, NHCHO, NHCOCH$_3$, NHCOCF$_3$
9 n = 1-4; R = CH$_3$; X = N; Y = CH; Z = CH$_2$, O, S, NH, NHCHO, NHCOCH$_3$, NHCOCF$_3$
10 n = 1-4; R = CH$_3$; X = N; Y = CH; Z = CH$_2$, O, S, NH, NHCHO, NHCOCH$_3$, NHCOCF$_3$

AGF315 n = 2; R = H; X = N; Y = CH; Z = CH$_2$
AGF317 n = 3; R = H; X = N; Y = CH; Z = CH$_2$

FORMULA III

Figure 7

5N-substituted pyrrolo[3,2-d]pyrimidine as multi-targeted agents with selective uptake All IC$_{50}$ values in nM

| AGF | hRFC | | hFRα | hRFC /hFRα | hPCFT | hRFC /PCFT | hRFC/ hFRα/hPCFT |
|---|---|---|---|---|---|---|---|
| | PC43-10 | R2 | RT16 | | R2/hPCFT4 | | KB |
| 291 | 43 | >1000 | 50 | 0.86 | 25.2 | 1.71 | 6.7 |
| 287 | 40 | >1000 | 5.23 | 7.64 | 52.7 | 0.94 | 7.99 |

| | IC50 (nM) | Ade/Thd/AICA/Gly Protection |
|---|---|---|
| AGF71 | 0.55(0.10) | Ade/AICA |
| AGF94 | 0.26(0.08) | Ade/AICA |
| AGF147 | 1.10(0.0.88) | Ade/AICA |
| AGF150 | 0.17 (0.20) | Ade/AICA |
| AGF154 | 0.09(0.02) | Ade/AICA |
| AGF287 | 8.00+/-0.54 | Gly+Ade |
| AGF291 | 5.73+/-0.28 | Gly+Ade |
| AGF300 | 26.03+/-12.97 | Gly+Ade |
| AGF307 | 5.53+/-0.11 | Gly+Ade |
| AGF312 | 9.61+/-0.47 | Ade |
| AGF315 | 15.93/0.86 | Ade |
| AGF317 | 2.51+/-0.90 | Gly+Ade |
| AGF318 | 2.58+/-0.34 | Not Determined |
| AGF320 | 7.47+/-0.34 | Gly+Ade |
| AGF323 | 8.23+/-0.17 | Gly+Ade |
| AGF331 | 23.70+-2.69 | Gly+Ade |

Figure 11

FIRST-IN-CLASS OF SHMT2 AND MTHFD2 INHIBITORS AS ANTITUMOR AGENTS

CROSS REFERENCE TO RELATED APPLICATION

This non-provisional patent application claims the benefit of U.S. Provisional Patent Application Ser. No. 62/552,432, filed Aug. 31, 2017. The entire contents of U.S. Provisional Patent Application Ser. No. 62/552,432, is incorporated by reference into this non-provisional patent application as if fully written herein.

STATEMENT REGARDING FEDERALLY SPONSORED RESEARCH

This invention was made with government support under Grant Nos. R01 CA166711, R01 CA152316, and R01 CA53535, and T32 CA009531 and F30 CA228221 and P30 CA022453, awarded by the National Institutes of Health. The government has certain rights in the invention.

BACKGROUND OF THE INVENTION

1. Field of the Invention

The present invention relates to novel compounds of Formulae I, II, and III, as described herein, and pharmaceutically acceptable salts thereof, that are effective to inhibit human tumor cells, including lung cancer and pancreatic cancer cells. This invention also relates to compositions, which include these novel compounds, for use in treating a patient with cancer including providing to the patient a therapeutically effective dose of one or more of the compounds and/or compositions as described herein to a patient.

2. Description of the Background Art

Serine hydroxymethyltransferase 2 (SHMT2) and 5,10-methylene tetrahydrofolate dehydrogenase 2 (MTHFD2) are critical enzymes in mitochondrial one-carbon metabolism. SHMT2 has recently been identified as an oncodriver and its inhibition, as determined by SHMT2 and knockouts MTHFD2, generates glycine auxotrophs. There are no known inhibitors of SHMT2 or MTHFD2. Thus, there is a need in the art to develop compounds that are inhibitors of SHMT2 or MTHFD2, as well as anticancer agents against cancers, such as, but not limited to, lung cancer and pancreatic cancer.

Metabolic reprogramming to support tumor progression has emerged as a hallmark of cancer (1). Of the many altered metabolic pathways associated with the malignant phenotype, one-carbon (C1) metabolism is particularly notable (2-4). C1 metabolism depends on an adequate supply of tetrahydrofolate (THF) metabolites and generates critical purine, thymidylate, and glycine metabolites essential for cell proliferation and tumor progression (3-5). Thymidylate and purine nucleotides are synthesized de novo in the cytosol (3-5), and C1 enzymes such as thymidylate synthase (TS) and the purine biosynthetic enzymes glycinamide ribonucleotide (GAR) formyltransferase (GARFTase) and 5-aminoimidazole-4-carboxamide (AICA) ribonucleotide (AICAR) formyltransferase (AICARFTase) (respectively, the third and ninth steps in de novo purine biosynthesis) are important therapeutic targets for cancer (6-8). Serine biosynthesis from glycine in the cytosol involves serine hydroxymethyltransferase (SHMT) 1 and uses C1 units from 5,10-methylene-THF (2-4).

Cytosolic and mitochondrial C1 metabolic pathways are interconnected by an exchange of serine, glycine and formate, see FIG. 1. Extracellular folates are transported into cells by the reduced folate carrier (RFC), proton-coupled folate transporter (PCFT) and folate receptors (FRs) (9, 10). Whereas cytosolic folates are transported into mitochondria via the mitochondrial folate transporter (MFT) (SLC25A32) (11, 12), mitochondrial folates do not exchange with those in the cytosol (13). In cancer cells, the 3-carbon of serine is the major source of C1 units, and in mitochondria, serine catabolic enzymes including SHMT2, 5,10-methylene-THF dehydrogenase 2 (MTHFD2) and 10-formyl-THF synthetase (reverse) (MTHFD1L) generate glycine and C1 units (i.e., formate) to sustain C1-dependent nucleotide and amino acid biosynthesis in the cytosol, see FIG. 1. 10-Formyl-THF is resynthesized from formate in the cytosol by the trifunctional enzyme MTHFD1. 10-Formyl-THF is utilized for purine nucleotide biosynthesis and can be converted to 5,10-methylene-THF for TS and SHMT1.

Several studies have implicated mitochondrial C1 metabolism as critical to the malignant phenotype (14-17). A study (16) of messenger RNA profiles for over one thousand enzymes spanning nearly two thousand tumors across nineteen different cancer types identified SHMT2 and MTHFD2 among the top five most upregulated genes, highlighting the key role of mitochondrial C1 metabolism across a wide spectrum of cancers. Metabolomics analyses of 219 extracellular metabolites from the NCI-60 cancer cell lines showed that glycine consumption and the glycine biosynthetic pathway strongly correlated with cancer cell proliferation (14). These findings, combined with evidence of functional shortages of amino acids (e.g., glycine) in tumors (18), suggested a therapeutic opportunity for SHMT2 targeting in cancer.

SHMT2 is induced by hypoxic stress in Myc-transformed cells (19) and is critical to tumor cell survival in the hypoxic, nutrient-poor tumor microenvironment (15, 19). SHMT2 (or MTHFD2) knockout (KO) cells are viable and tumorigenic (albeit with decreased growth rates) in nutrient-rich conditions, as reversal of cytosolic SHMT1 (serine→glycine) provides sufficient C1 units to sustain some level of de novo nucleotide biosynthesis (20). However, SHMT1 only restores a small fraction of the C1 pools in wild-type (WT) cells (20). Further, SHMT1 does not generate sufficient glycine for protein, nucleotide and glutathione biosynthesis, rendering both SHMT2 and MTHFD2 KO cells as glycine auxotrophs (4). This, in part, was the impetus for studies of a series of pyranopyrazole compounds (e.g., SHIN 1) with dual SHMT1/SHMT2 inhibition (21). While structurally unrelated to folates, these compounds bound to the folate binding site in SHMT2 and showed in vitro anti-tumor efficacy (particularly with B-cell cancers). However, they were inactive in vivo, likely reflecting their poor metabolic stabilities (21).

SUMMARY OF THE INVENTION

The present invention satisfies the above described needs by providing novel compounds to potently inhibit human tumor cells including lung cancer and pancreatic cancer cells. In addition, the novel analogs according to the invention target a novel oncodriver, serine hydroxymethyltransferase from the mitochondria (SHMT2) and methylene tetrahydrofolate dehydrogenase (MTHFD2). Since there are no known inhibitors of SHMT2 or MTHFD2, these novel compounds of this invention are first-in-class SHMT2 and/or MTHFD2 inhibitors useful in cancer treatment.

One embodiment of this invention provides a compound of Formula I, and optionally a pharmaceutically acceptable salt thereof:

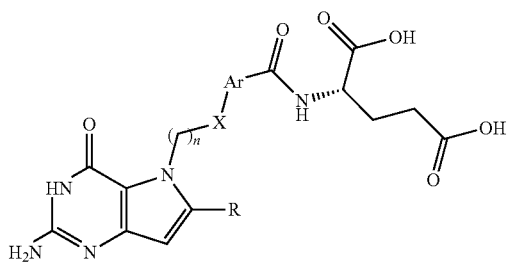

Formula I,
wherein, R is selected from the group consisting of H and CH$_3$; n is an integer ranging from 1 to 4; X is selected from the group of —CH$_2$—, O, S, —NH—, —NHCHO—, —NHCOCH$_3$—, and —NHCOCF$_3$—; and Ar is selected from the group of (a) 1,4-phenyl, (b) 2'-fluoro-1,4-phenyl, and (c) 2,5-thienyl.

In a preferred embodiment of this invention, a compound of Formula I, and optionally a pharmaceutically acceptable salt thereof, is provided wherein n=2, Ar is 1,4-phenyl, R is H, and X is CH$_2$. This compound is further identified herein as AGF291.

In a preferred embodiment of this invention, a compound of Formula I, and optionally a pharmaceutically acceptable salt thereof, is provided wherein n=3, Ar is 1,4-phenyl, R is H, and X is CH$_2$. This compound is further identified herein as AGF300.

In a preferred embodiment of this invention, a compound of Formula I, and optionally a pharmaceutically acceptable salt thereof, is provided wherein n=4, Ar is 1,4-phenyl, R is CH$_3$, and X is CH$_2$. This compound is further identified herein as AGF307.

In a preferred embodiment of this invention, a compound of Formula I, and optionally a pharmaceutically acceptable salt thereof, is provided wherein n=3, Ar is 1,4-phenyl, R is CH$_3$, and X is CH$_2$. This compound is further identified herein as AGF312.

In a preferred embodiment of this invention, a compound of Formula I, and optionally a pharmaceutically acceptable salt thereof, is provided wherein n=3, Ar is 2,5-thienyl, R is H, and X is CH$_2$. This compound is further identified herein as AGF318.

In a preferred embodiment of this invention, a compound of Formula I, and optionally a pharmaceutically acceptable salt thereof, is provided wherein n=4, Ar is 2,5-thienyl, R is H, and X is CH$_2$. This compound is further identified herein as AGF320.

In a preferred embodiment of this invention, a compound of Formula I, and optionally a pharmaceutically acceptable salt thereof, is provided wherein n=2, Ar is 2,5-thienyl, R is H, and X is CH$_2$. This compound is further identified herein as AGF331.

In a preferred embodiment of this invention, a compound of Formula I, and optionally a pharmaceutically acceptable salt thereof, is provided wherein n is selected from the group of integers of 1,3, and 4, R is H, X is CH$_2$, Ar is selected from the group of 1,4-phenyl and 2,5-thienyl.

In a preferred embodiment of this invention, a compound of Formula I, and optionally a pharmaceutically acceptable salt thereof, is provided wherein n is selected from the group of integers of 1, 2, 3, and 4, R is CH$_3$, X is CH$_2$, Ar is selected from the group of 1,4-phenyl and 2,5-thienyl.

In a preferred embodiment of this invention, a compound of Formula I, and optionally a pharmaceutically acceptable salt thereof, is provided wherein n is selected from the group of integers of 2, 3, and 4, R is H, X is selected from the group of O, S, NH, NHCHO, NHCOCH$_3$, and NHCOCF$_3$, and Ar is selected from the group of (a) 1,4-phenyl, (b) 2'-fluoro-1,4-phenyl, and (c) 2,5-thienyl.

Another embodiment of this invention provides a pharmaceutical composition comprising a therapeutically effective amount of a compound of Formula I, and optionally a pharmaceutically acceptable salt thereof:

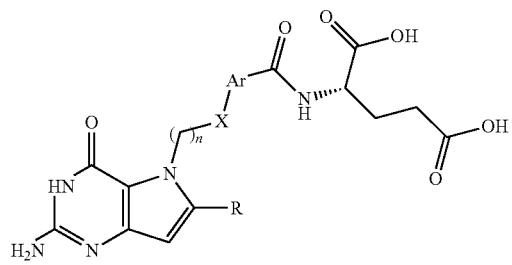

Formula I,
wherein, R is selected from the group consisting of H and CH$_3$; n is an integer ranging from 1 to 4; X is selected from the group of —CH$_2$—, O, S, —NH—, —NHCHO—, —NHCOCH$_3$—, and —NHCOCF$_3$—; and Ar is selected from the group of (a) 1,4-phenyl, (b) 2'-fluoro-1,4-phenyl, and (c) 2,5-thienyl. Another embodiment of this invention provides the pharmaceutical composition having the compound of Formula I, as described herein, including a pharmaceutically acceptable carrier.

In another embodiment of this invention, a compound is provided of Formula II, and optionally a pharmaceutically acceptable salt thereof:

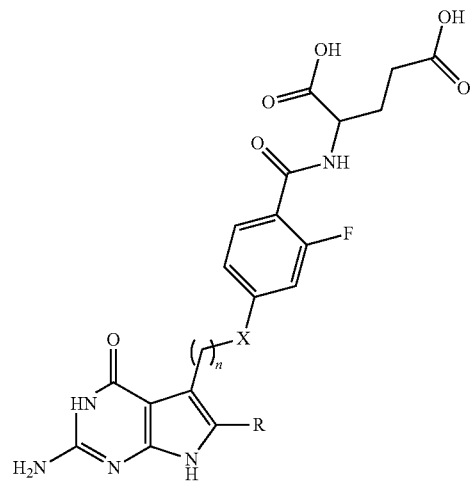

Formula II, wherein, R is selected from the group consisting of H and CH$_3$;

n is an integer ranging from 1 to 4; X is selected from the group of —CH$_2$—, O, S, —NH—, —NHCHO—, —NHCOCH$_3$—, and —NHCOCF$_3$—.

In a preferred embodiment of this invention, a compound of Formula II, and optionally a pharmaceutically acceptable salt thereof, is provided wherein n is 3, R is H, X is CH$_2$. This compound is identified herein as AGF287.

In a preferred embodiment of this invention, a compound of Formula II, and optionally a pharmaceutically acceptable salt thereof, is provided wherein n is selected from the group of integers of 1, 2, and 4, R is H, and X is CH$_2$.

In a preferred embodiment of this invention, a compound of Formula II, and optionally a pharmaceutically acceptable salt thereof, is provided wherein n is selected from the group of integers of 1, 2, 3, and 4, R is CH$_3$, and X is CH$_2$.

In a preferred embodiment of this invention, a compound of Formula II, and optionally a pharmaceutically acceptable salt thereof, is provided wherein n is selected from the group of integers of 1, 2, 3, and 4, R is H, and X is selected from the group of O, S, NH, NHCHO, NHCOCH$_3$, and NHCOCF$_3$.

Another embodiment of this invention provides a pharmaceutical composition comprising a therapeutically effective amount of a compound of Formula II, and optionally a pharmaceutically acceptable salt thereof:

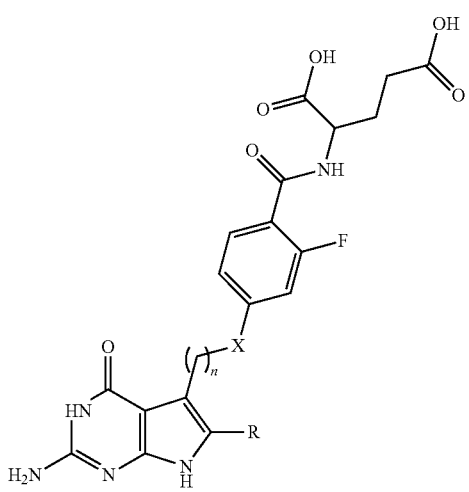

Formula II, wherein, R is selected from the group consisting of H and CH$_3$; n is an integer ranging from 1 to 4; X is selected from the group of —CH$_2$—, O, S, —NH—, —NHCHO—, —NHCOCH$_3$—, and —NHCOCF$_3$—. A further embodiment of this invention provides a pharmaceutical composition having a compound of Formula II, as described herein, and including a pharmaceutically acceptable carrier.

Another embodiment of this invention provides a compound of Formula III, and optionally a pharmaceutically acceptable salt thereof:

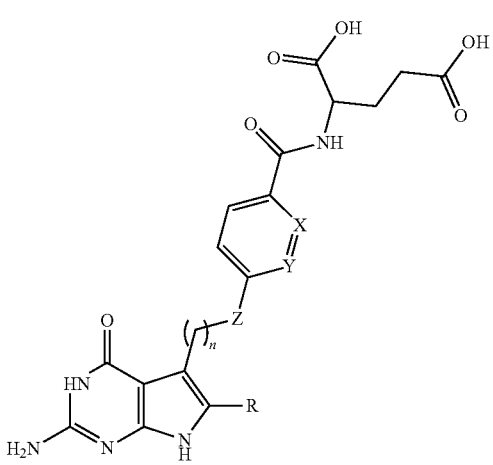

Formula III, wherein, R is selected from the group consisting of H and CH$_3$; n is an integer ranging from 1 to 4; X is selected from the group of CH and N; Y is selected from the group of CH and N; and Z is selected from the group of —CH$_2$—, O, S, —NH—, —NHCHO—, —NHCOCH$_3$—, and —NHCOCF$_3$—.

In a preferred embodiment of this invention, a compound of Formula III, and optionally a pharmaceutically acceptable salt thereof, is provided wherein n is 2, and R is H, and X is N, Y is either CH or N, and Z is selected from the group of CH$_2$, O, S, NH, NHCHO, NHCOCH$_3$, and NHCOCF$_3$.

In a preferred embodiment of this invention, a compound of Formula III, and optionally a pharmaceutically acceptable salt thereof, is provided wherein n=2, R is H, Z is CH$_2$, X is N and Y is CH. An example of this compound is identified herein as AGF315.

In a preferred embodiment of this invention, a compound of Formula III, and optionally a pharmaceutically acceptable salt thereof, is provided wherein n is 3, and R is H, and X is either CH or N, Y is either CH or N, and Z is selected from the group of CH$_2$, O, S, NH, NHCHO, NHCOCH$_3$, and NHCOCF$_3$.

In a preferred embodiment of this invention, a compound of Formula III, and optionally a pharmaceutically acceptable salt thereof, is provided wherein n is 3, R is H, Z is CH$_2$, X is N and Y is CH. An example of this compound is identified herein as AGF317.

In a preferred embodiment of this invention, a compound of Formula III, and optionally a pharmaceutically acceptable salt thereof, is provided wherein n is an integer selected from the group of 1, 2, 3, and 4, and R is H, and X is N, Y is CH, and Z is selected from the group of CH$_2$, O, S, NH, NHCHO, NHCOCH$_3$, and NHCOCF$_3$.

In a preferred embodiment of this invention, a compound of Formula III, and optionally a pharmaceutically acceptable salt thereof, is provided wherein n is an integer selected from the group of 1, 2, 3, and 4, and R is H, and X is CH, Y is N, and Z is selected from the group of CH$_2$, O, S, NH, NHCHO, NHCOCH$_3$, and NHCOCF$_3$.

In a preferred embodiment of this invention, a compound of Formula III, and optionally a pharmaceutically acceptable salt thereof, is provided wherein n is an integer selected from the group of 1, 2, 3, and 4, and R is CH$_3$, and X is N, Y is CH, and Z is selected from the group of $CH_2$, O, S, NH, NHCHO, NHCOCH$_3$, and NHCOCF$_3$.

In a preferred embodiment of this invention, a compound of Formula III, and optionally a pharmaceutically acceptable salt thereof, is provided wherein n is an integer selected from the group of 1, 2, 3, and 4, and R is $CH_3$, and X is N, Y is CH, and Z is selected from the group of $CH_2$, O, S, NH, NHCHO, NHCOCH$_3$, and NHCOCF$_3$.

Another embodiment of this invention provides a pharmaceutical composition comprising a therapeutically effective amount of a compound of Formula III, and optionally a pharmaceutically acceptable salt thereof:

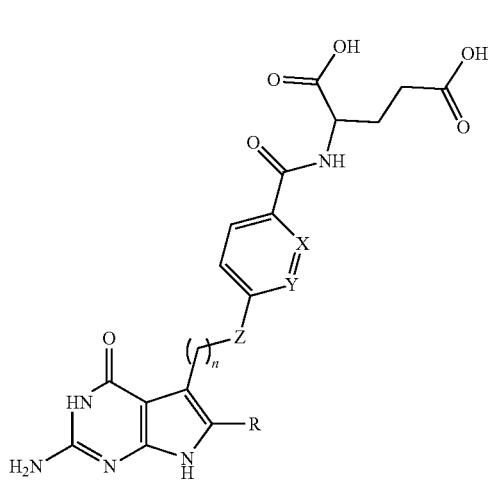

Formula III, wherein, R is selected from the group consisting of H and $CH_3$; n is an integer ranging from 1 to 4; X is selected from the group of CH and N; Y is selected from the group of CH and N; and Z is selected from the group of —$CH_2$—, O, S, —NH—, —NHCHO—, —NHCOCH$_3$—, and —NHCOCF$_3$—. A further embodiment of this invention provides the pharmaceutical composition having the compound of Formula III, as described herein, and a pharmaceutically acceptable carrier.

Another embodiment of this invention provides a method of treating a patient having cancer comprising administering to said patient a therapeutically effective amount of a compound of Formula I, and optionally a pharmaceutically acceptable salt thereof:

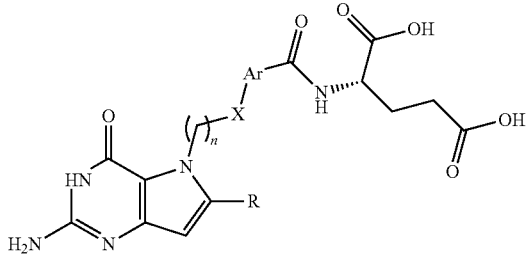

Formula I, wherein, R is selected from the group consisting of H and $CH_3$; n is an integer ranging from 1 to 4; X is selected from the group of —$CH_2$—, O, S, —NH—, —NHCHO—, —NHCOCH$_3$—, and —NHCOCF$_3$—; and Ar is selected from the group of (a) 1,4-phenyl, (b) 2'-fluoro-1,4-phenyl, and (c) 2,5-thienyl. A preferred embodiment of this invention provides a method of treating a patient having cancer comprising administering a therapeutically effective amount of at least one compound of Formula I selected from the group of AGF 291, AGF 299, AGF300, AGF307, AGF312, AGF318, AGF320, AGF323, AGF331, AGF 347, AGF 355, and AGF 359, and optionally a pharmaceutically acceptable salt thereof, to said patient.

Another embodiment of this invention provides a method of treating a patient having cancer comprising administering a therapeutically effective amount of a compound of Formula II, and optionally a pharmaceutically acceptable salt thereof:

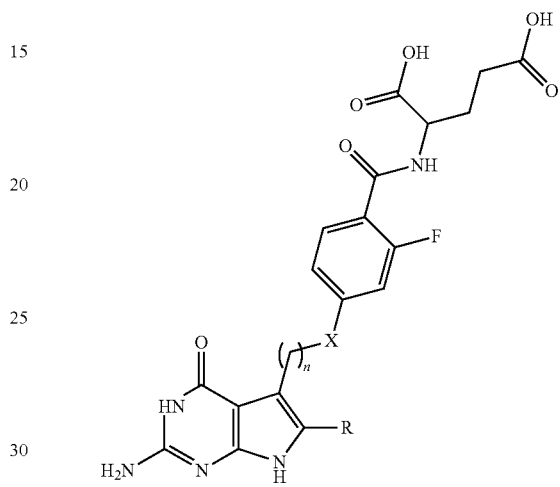

Formula II, wherein, R is selected from the group consisting of H and $CH_3$; n is an integer ranging from 1 to 4; and X is selected from the group of —$CH_2$—, O, S, —NH—, —NHCHO—, —NHCOCH$_3$—, and —NHCOCF$_3$—. A preferred embodiment of this invention provides a method of treating a patient having cancer comprising administering a therapeutically effective amount of a compound of Formula II that is AGF287, and optionally a pharmaceutically acceptable salt thereof, to said patient.

Another embodiment of this invention provides a method of treating a patient having cancer comprising administering a therapeutically effective amount of a compound of Formula III, and optionally a pharmaceutically acceptable salt thereof:

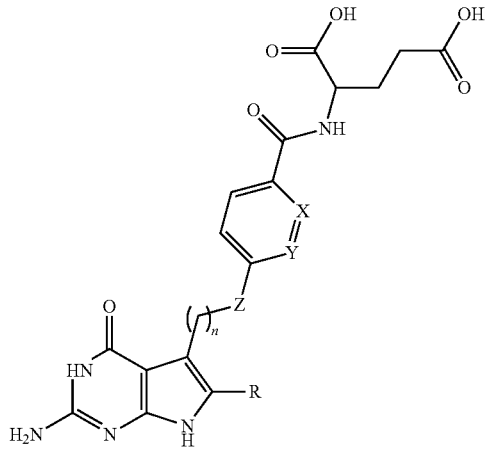

Formula III, wherein, R is selected from the group consisting of H and CH₃; n is an integer ranging from 1 to 4; X is selected from the group of CH and N; Y is selected from the group of CH and N; and Z is selected from the group of —CH₂—, O, S, —NH—, —NHCHO—, —NHCOCH₃—, and —NHCOCF₃—. A preferred embodiment of this invention provides a method of treating a patient having cancer comprising administering a therapeutically effective amount of at least one compound of Formula III selected from the group of AGF 315 and AGF 317, and optionally a pharmaceutically acceptable salt thereof, to said patient.

Another embodiment of this invention provides a method of targeting mitochondrial metabolism comprising administering to a cancer patient an effective amount of at least one compound selected from the group of Formula I, and optionally a pharmaceutically acceptable salt thereof, of Formula II, and optionally a pharmaceutically acceptable salt thereof, and of Formula III, and optionally a pharmaceutically acceptable salt thereof:

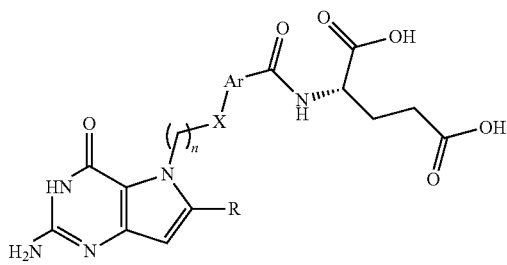

Formula I, wherein, R is selected from the group consisting of H and CH₃; n is an integer ranging from 1 to 4; X is selected from the group of —CH₂—, O, S, —NH—, —NHCHO—, —NHCOCH₃—, and —NHCOCF₃—; and Ar is selected from the group of (a) 1,4-phenyl, (b) 2'-fluoro-1,4-phenyl, and (c) 2,5-thienyl; and

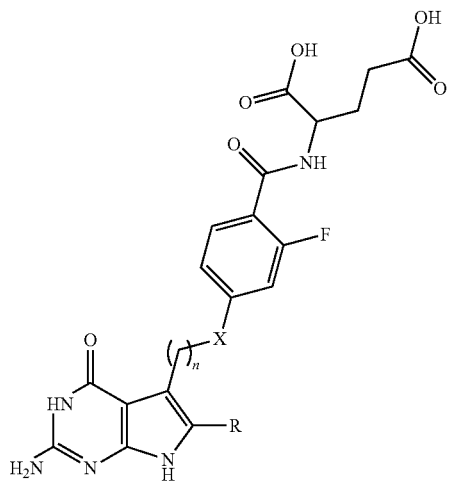

Formula II, wherein, R is selected from the group consisting of H and CH₃; n is an integer ranging from 1 to 4; and X is selected from the group of —CH₂—, O, S, —NH—, —NHCHO—, —NHCOCH₃—, and —NHCOCF₃—; and

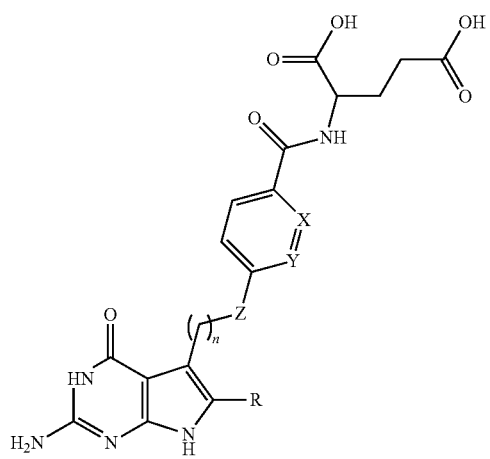

Formula III, wherein R is selected from the group consisting of H and CH₃; n is an integer ranging from 1 to 4; X is selected from the group of CH and N; Y is selected from the group of CH and N; and Z is selected from the group of —CH₂—, O, S, —NH—, —NHCHO—, —NHCOCH₃—, and —NHCOCF₃—.

Another embodiment of this invention provides a method of targeting SHMT2 and MTHFD2 comprising administering to a cancer patient an effective amount of at least one compound selected from the group of Formula I, and optionally a pharmaceutically acceptable salt thereof, of Formula II, and optionally a pharmaceutically acceptable salt thereof, and of Formula III, and optionally a pharmaceutically acceptable salt thereof:

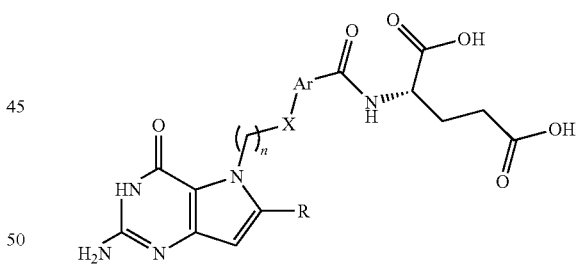

Formula I, wherein, R is selected from the group consisting of H and CH₃; n is an integer ranging from 1 to 4; X is selected from the group of —CH₂—, O, S, —NH—, —NHCHO—, —NHCOCH₃—, and —NHCOCF₃—; and Ar is selected from one of the group of (a) 1,4-phenyl, (b) 2'-fluoro-1,4-phenyl, and (c) 2,5-thienyl; and

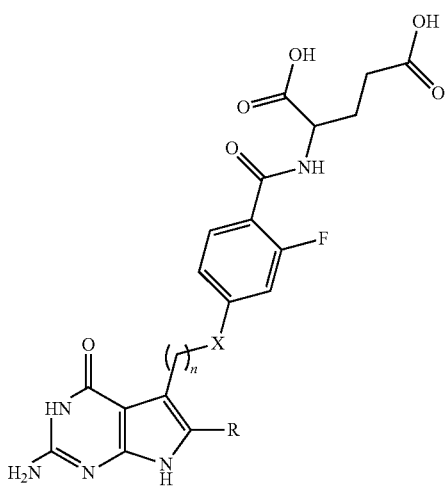

Formula II, wherein, R is selected from the group consisting of H and $CH_3$; n is an integer ranging from 1 to 4; and X is selected from the group of —$CH_2$—, O, S, —NH—, —NHCHO—, —NHCOCH$_3$—, and —NHCOCF$_3$—; and

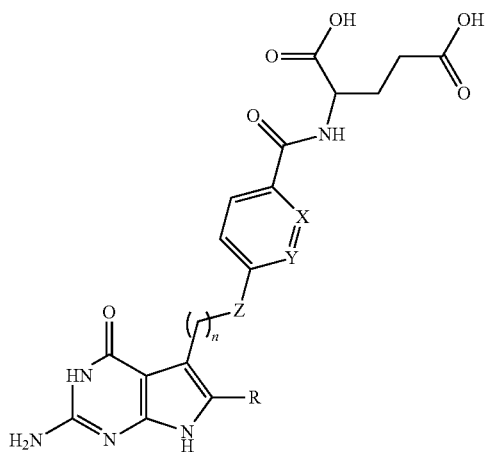

Formula III, wherein R is selected from the group consisting of H and $CH_3$; n is an integer ranging from 1 to 4; X is selected from the group of CH and N; Y is selected from the group of CH and N; and Z is selected from the group of —$CH_2$—, O, S, —NH—, —NHCHO—, —NHCOCH$_3$—, and —NHCOCF$_3$—.

BRIEF DESCRIPTION OF THE DRAWINGS

A full description of the invention may be gained from the following description of the preferred embodiments of the invention when read in conjunction with the accompanying drawings:

FIG. 4A shows a schematic of serine isotope label scrambling and dTTP isotope analysis. Heavy ($^2$H) atoms are represented by filled in circles with lighter shading representing the flux through the cytosol including TS (forming M+2 dTMP and dTTP, as shown) and darker shading representing the flux through the mitochondria beginning with SHMT2 (forming M+1 dTTP). Most steps are reversible as indicated. Adapted from (20). FIG. 4B and FIG. 4C show total serine pools for HCT116 sublines including drug-treated WT cells (FIG. 4B) and the corresponding serine isotope distributions (FIG. 4C). FIG. 4D and FIG. 4E show total GAR (FIG. 4D) and AICAR (FIG. 4E) pools in H460 sublines including drug-treated WT cells with and without treatment with 1 mM formate. FIGS. 4F and 4G show relative dTTP pools (FIG. 4F) and dTTP isotope distributions (FIG. 4G) in H460 sublines including drug-treated WT cells with and without 1 mM formate. For FIG. 4D, FIG. 4E and FIG. 4F, results for drug-treated and SHMT2 KD cells were normalized to vehicle-treated WT±formate or NTC±formate samples, as appropriate. All data are mean values+/−standard deviations of three technical replicates. #, p<0.10; *, p<0.05; , p<0.01; *, p<0.001; ˆ or ᵛ are used in place of * to specify a significant increase or decrease, respectively. Statistical comparisons were with vehicle-treated WT±formate or NTC±formate samples, as appropriate. "ns" means not significant.

FIG. 7 shows several of the chemical structures of the compounds of this invention, namely, Formula I, Formula II, and Formula III.

FIG. 10A shows transcript levels for human PCFT, FIG. 10B shows transcript levels for RFC, and FIG. 10C shows transcript levels for FRα in 4 normal pancreas. 19 PaCspecimens (OriGene) and the TM00176 PaC PDX were measured by qPCR and normalized β-actin transcripts, and in comparison to KB tumor cells. FIGS. 10D and 10E show immunohistochemistry (IHC) staining of PCFT that was performed with 99 primary PaC specimens and 4 normal pancreas tissues from a commercial TMA (US Biomax, Inc.). The TMA was incubated with affinity-purified PCFT-specific antibody or rabbit IgG, the slides developed, counterstained and mounted. The slides were scanned at 20× by an Aperio Image Scanner (Aperio Technologies, Inc.) for microarray images. The total intensity of antibody positive staining of each tissue core was computed and plotted as relative values. Median values are shown as cross bars. Representative images are shown in panel FIG. 10D.

FIG. 11 shows the results of growth inhibition of KB human tumor cells by the compounds of the present invention and the results of protection experiments with nucleosides, 5-aminoimidazole-4-carboxamide and glycine. Growth inhibition was measured by a fluorescence-based assay (Cell TiterBlue™). Cells were cultured in folate-free (FF) RPMI 1640/10% dialyzedfetal bovine serum, and antibiotics, with 2 nM leucovorin. Results are expressed as nM IC50s (n=3-10; mean+SEM in parenthesis) relative to untreated control cells. For KB cells, results are summarized for the protective effects of nucleoside additions including adenosine (Ade) (60 μM) or thymidine (Thd) (10 or 5-aminoimidazole-4-carboxamide (AICA) (320 μM) or glycine (Gly) (120 μM).

The 2-fluorophenyl ring is sandwiched between Tyr176 and Tyr105. The 2-fluro substitution makes steric clash with the carbonyl oxygen of amide group forcing the amide group perpendicular to the phenyl ring, which further forces the H-bond with the Tyr176 and Tyr105 hydroxyl groups. The α- and γ-COOH groups of the glutamyl side chain make salt bridge (blue color dotted line) with Lys181 and Lys103. These ionic interactions are maintained by AGF291 and AGF320, along with the aromatic side chains phenyl and thienoyl, respectively, resulting in pi-pi interaction (dark color dotted line) with Tyr176. Panels E-H. AGF320 shows the highest docking score among all the proposed analogs for SHMT1 (Table 1s). The pyrrolo[3,2-d]pyrimidine scaffold for AGF320 (panel G) sits in the pocket occupied by Leu121, Leu127, Gly125, His203, Arg363, Lys346, and Asn347. The 2-NH$_2$ group makes H-bonds (faded color line) with the backbone CO of Leu121 and Gly125. The 4-oxo make water mediated H-bond with Tyr65 and His203. The α-COOH makes H-bond with backbone of Leu357 and γ-COOH makes salt-bridge (dark dotted line) with Lys134B.

Figure 13:
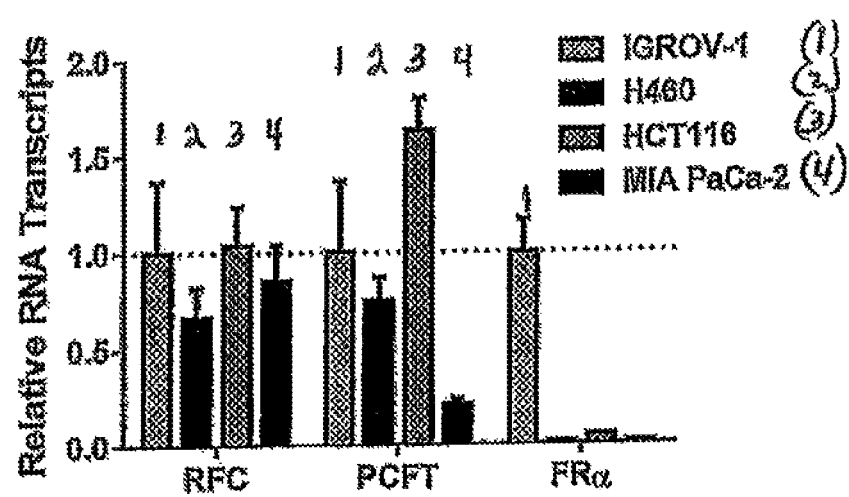

FIG. 13 shows folate transporter transcript expression of human tumor cell lines by RT-PCR. Transcript levels for reduced folate carrier (RFC), proton-coupled folate transporter (PCFT) and folate receptor (FR) a in H460, HCT116 and MIA PaCa-2, and IGROV1 cells were measured by real-time RT-PCR with results normalized to those of β-actin and GAPDH. The results represent three experimental replicates with individual transporter expression within each replicate normalized to the average of the corresponding transporter expression across all IGROV-1 replicates. The results are presented as mean values+/−standard deviations. Although H460, HCT116 and MIA PaCa-2 cells all express abundant RFC and PCFT, FRα expression is negligible.

Figure 14:
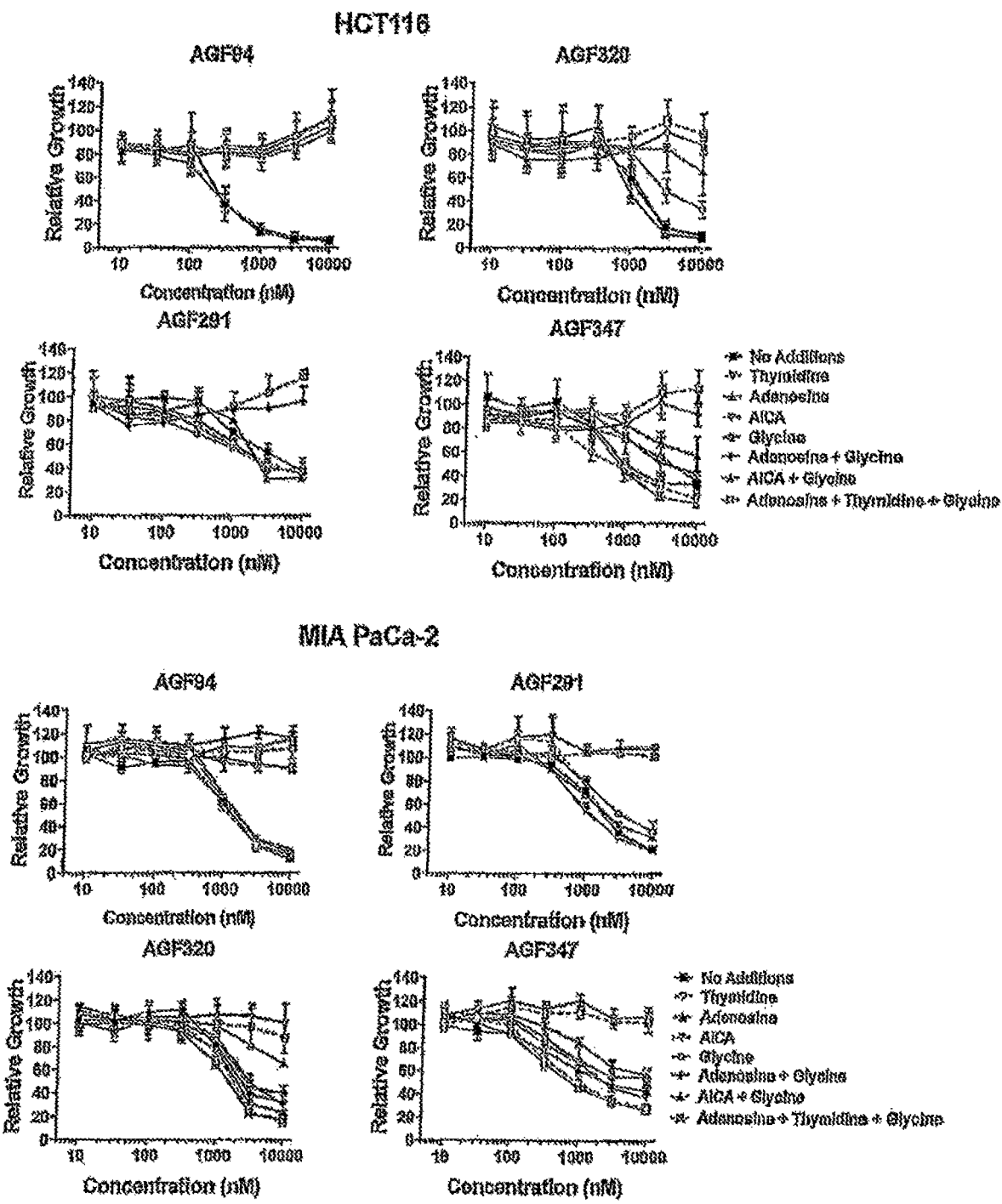

FIG. 14 shows in vitro antitumor efficacy and identification of targeted pathways and enzymes by novel 5-substituted pyrrolo[3,2-d]pyrimidine benzoyl and thienoyl compounds of this invention in HCT116 and MIA PaCa-2 tumor cells. Dose-response curves are shown for AGF94, an established glycinamide ribonucleotide formyltransferase (GARFTase) inhibitor (46) and the 5-substituted pyrrolo[3,2-d] pyrimidine compounds AGF291, AGF320, and AGF347 of this invention without additions, or in the presence of adenosine (60 μM), 5-aminoimidazole-4-carboxamide (AICA) (320 μM), thymidine (10 μM) and/or glycine (120 μM). The experiments were performed in complete folate-free RPMI1640, supplemented with 25 nM leucovorin without added glycine (see methods as described herein). The results are presented as mean values±standard deviations for at least three biological replicates, with growth of cells treated with drug±metabolite normalized to the growth of cells treated with vehicle (i.e., DMSO)±metabolite.

Figures 15A, 15B, 15C, 15D, 15E, 15F, 15G, 15H, 15I, 15J, 15K, 15L:
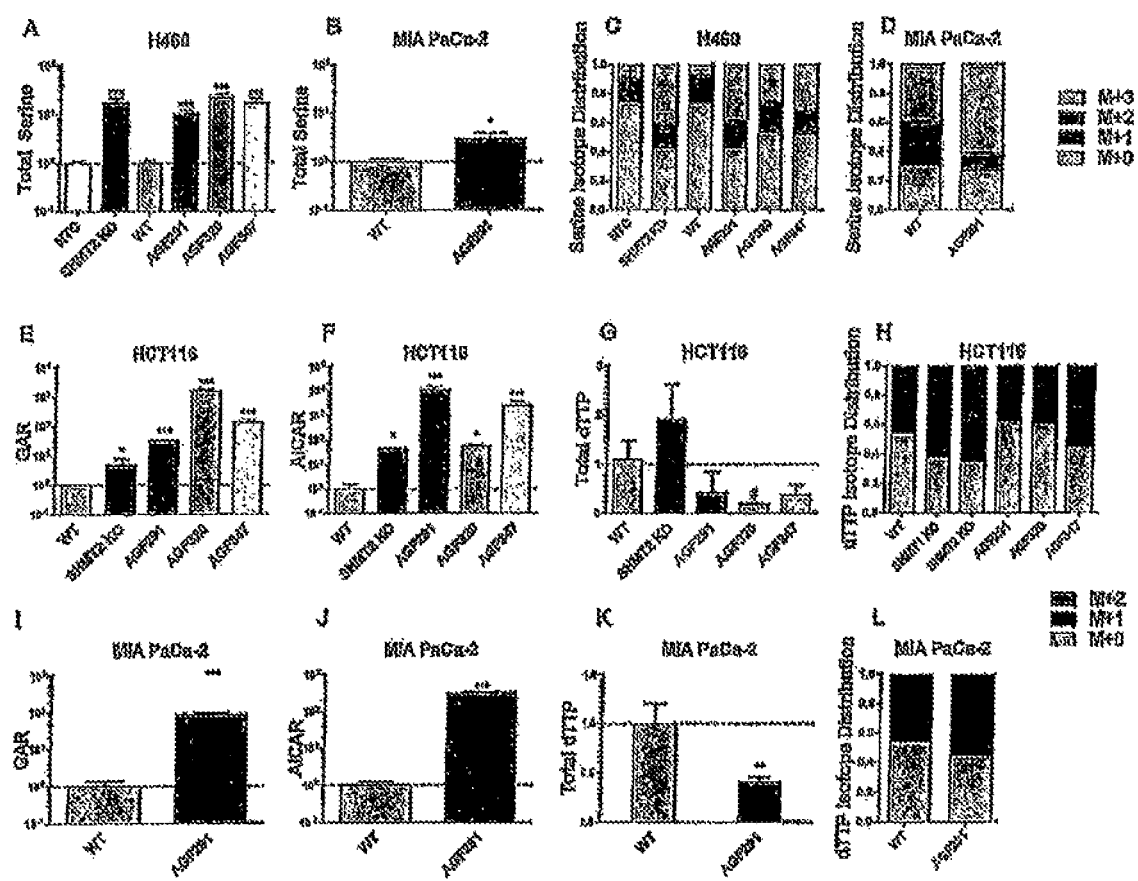

FIGS. 15A-15L show targeted metabolomics analysis to identify intracellular enzyme targets of compounds of this invention AGF291, AGF320, and AGF347 in HCT116, H460, and MIA PaCa-2 cells. Cells were incubated with drug or vehicle for 16 hours in glycine-replete, folate-free complete RPMI 1640, supplemented with 25 nM leucovorin (included unlabeled serine). The medium was replaced with media (including drug or vehicle) including 250 μM [2,3,3-$^2$H]serine for another 24 hours, after which metabolites were extracted for LC-MS analysis. FIG. 15A and FIG. 15C, respectively, show total serine pools and serine isotope distributions for H460 cells. FIG. 15B and 15D, respectively, show MIA PaCa-2 cells. FIG. 15E and FIG. 15F, respectively, show GAR and AICAR accumulations in HCT116 cells, and FIGS. 15I and 15J, respectively, show MIA PaCa-2 cells. FIGS. 15G and 15H, respectively, show total dTTP pools and dTTP serine isotope distributions for HCT116. FIGS. 15K and 15L, respectively, show MIA PaCa-2 cells. Results reflect three technical replicates. #, $p<0.10$; *, $p<0.05$; , $p<0.01$; *, $p<0.001$; ^ or $^v$ are used in place of * to specify a significant increase or decrease respectively; ns=not significant. All statistical comparisons were made between drug-treated/knockout/knockdown samples and DMSO-treated WT/NTC samples.

Figure 16:
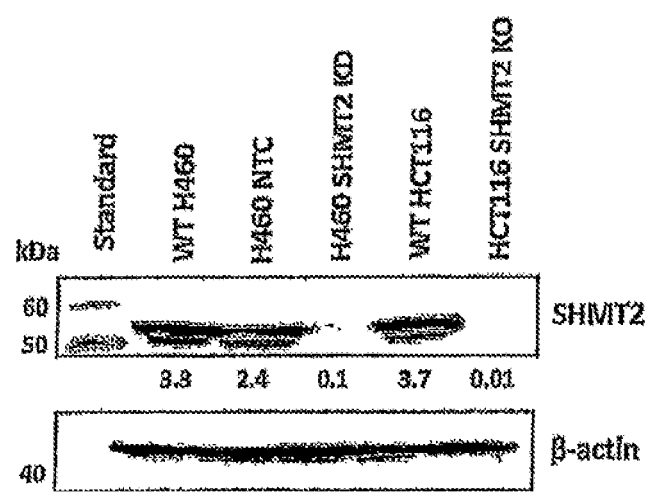

FIG. 16 shows the Western blot confirming H460 SHMT2 knockdown and HCT116 SHMT2 knockout. Whole-cell lysates of wild-type (WT), non-targeted control shRNA-transduced (NTC), and clonal SHMT2 knockdown (SHMT2 KD) H460 cells, along with HCT116 WT and SHMT2 CRISPR/Cas9 knockout (KO) cells were resolved on 10% polyacrylamide gel with SDS and probed with monoclonal rabbit anti-SHMT2 antibody (#12762; Cell Signaling Technology, Danvers, Mass.). The blot was stripped and reprobed with mouse anti-β-actin antibody (Sigma-Aldrich) as a loading control. Experimental details are described herein. The blots were scanned with an Odyssey infrared imaging system (LICOR Biosciences). Densitometry analysis (values given are SHMT2 band intensities normalized to (3-actin band intensities) revealed SHMT2 protein expression of H460 SHMT2 KD to be 5.3% of that of H460 NTC, and HCT116 SHMT2 KO expression to be <1% of that of HCT116 WT.

DESCRIPTION OF THE PREFERRED EMBODIMENTS

As used herein, the term "patient" means members of the animal kingdom, including but not limited to, human beings.

As used herein, the term "effective amount" or "therapeutically effective amount" refers to that amount of any of the present compounds, salts thereof, and/or compositions required to bring about a desired effect in a patient. The desired effect will vary depending upon the illness or disease state being treated. For example, the desired effect may be reducing the tumor size, destroying cancerous cells, and/or preventing metastasis, any one of which may be the desired therapeutic response. On its most basic level, a therapeutically effective amount is that amount of a substance needed to inhibit mitosis of a cancerous cell. As used herein, "tumor" refers to an abnormal growth of cells or tissues of the malignant type, unless otherwise specifically indicated and does not include a benign type tissue. The "tumor" may be comprised of at least one cell and/or tissue. The term "inhibits or inhibiting" as used herein means reducing growth/replication. As used herein, the term "cancer" refers to any type of cancer, including but not limited to lung cancer, pancreatic cancer, and the like.

As used herein, the term "glutamate" will be understood as representing both the ester form (glutamate) and the acid form (glutamic acid).

The novel compounds and pharmaceutically acceptable salts thereof provide for treatment of tumors, or other cancer cells, in cancer patients. The types of cancer can vary widely and in certain embodiments, the novel compounds and pharmaceutically acceptable salts thereof are particularly useful for example, in treating lung cancer and pancreatic cancer.

The present invention is further directed to methods of synthesizing the novel compounds.

The present invention further relates to methods of using the above-described novel compounds, and pharmaceutically acceptable salts thereof, in therapeutically treating patients with cancer according to a method, such as, including the steps of:

a) employing the above-described compound, or pharmaceutically acceptable salt thereof;

b) incorporating said compound in a suitable pharmaceutical carrier; and c) administering a therapeutically effective amount of said compound incorporated in said carrier to a patient.

As used herein, the term "therapeutically effective carrier" refers to any pharmaceutical carrier known in the art, absent compatibility problems with the novel compounds of the invention. Generally, carriers include for example but not limited to, physiologic saline and 5% dextrose in water.

As will be understood by one skilled in the art, a therapeutically effective amount of said compound can be administered by any means known in the art, including but not limited to, injection, parenterally, intravenously, intraperitoneally, orally or, where appropriate, topically.

It is well within the skill of one practicing in the art to determine what dosage, and the frequency of this dosage, which will constitute a therapeutically effective amount for each individual patient, depending on the severity or progression of cancer or cancer cells and/or the type of cancer. It is also within the skill of one practicing in the art to select the most appropriate method of administering the compounds based upon the needs of each patient.

The compounds disclosed in the present invention all can be generally described as antifolates.

The novel compounds have been discovered, unexpectedly, to potently inhibit human tumor cells including lung cancer and pancreatic cancer cells. More particularly, the compounds and the pharmaceutically acceptable salts thereof used to treat pancreatic cancer are completely unprecedented, as no other known antifolate compound that inhibits pancreatic cancer cells has been described in the background art.

Protection studies of metabolic end products, e.g., nucleosides and amino acids, with tumor cells indicate that these analogs unexpectedly target a novel oncodriver, serine hydroxymethyltransferase (SHMT2) and/or methylene tetrahydrofolate dehydrogenase 2 (MTHFD2) from the mitochondria. Typically, the inhibitory effects of antifolate compounds are protected by adenosine or thymidine, required for DNA synthesis. However, these novel analogs, unexpectedly, require glycine along with adenosine for complete protection, clearly establishing that mitochondrion one-carbon metabolism is being targeted.

It has been shown that metabolism of serine (the substrate for SHMT2) and biosynthesis using a one carbon unit derived from serine is potently inhibited in tumor cells treated with the novel compounds of the present invention, which provides further evidence that mitochondrial metabolism, in general, and SHMT2 and/or MTHFD2, in particular, are being targeted.

Thus, the novel compounds of the invention, e.g., 5-substituted pyrrolo[2,3-d]- and pyrrolo[3,2-d]pyrimidines, are first-in-class inhibitors of SHMT2 and/or MTHFD2, and are anticancer agents against cancer, such as, but not limited to, lung cancer and pancreatic cancer.

One embodiment of this invention provides a compound of Formula I, and optionally a pharmaceutically acceptable salt thereof:

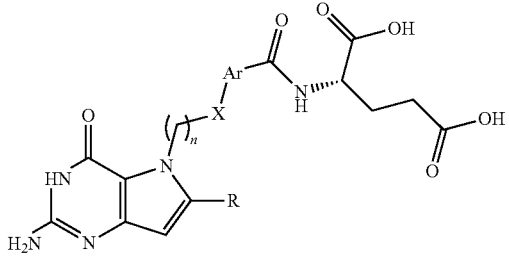

Formula I, wherein, R is one selected from the group consisting of H and $CH_3$; n is an integer ranging from 1 to 4; X is selected from one of the group consisting of —$CH_2$—, O, S, —NH—, —NHCHO—, —$NHCOCH_3$—, and —$NHCOCF_3$—; and Ar is selected from one of the group consisting of (a) 1,4-phenyl, (b) 2'-fluoro-1,4-phenyl, and (c) 2,5-thienyl. Those persons skilled in the art will appreciate that any of the combination(s) of the moieties identified for the groups of R, X, and Ar, and integers identified for n, are embodiments of the present invention for any of the formula(ae) presented for Formula I.

In a preferred embodiment of this invention, a compound of Formula I, and optionally a pharmaceutically acceptable salt thereof, is provided wherein n=2, Ar is 1,4-phenyl, R is H, and X is $CH_2$. This compound is further identified herein as AGF291.

In a preferred embodiment of this invention, a compound of Formula I, and optionally a pharmaceutically acceptable salt thereof, is provided wherein n=3, Ar is 1,4-phenyl, R is H, and X is $CH_2$. This compound is further identified herein as AGF300.

In a preferred embodiment of this invention, a compound of Formula I, and optionally a pharmaceutically acceptable salt thereof, is provided wherein n=4, Ar is 1,4-phenyl, R is $CH_3$, and X is $CH_2$. This compound is further identified herein as AGF307.

In a preferred embodiment of this invention, a compound of Formula I, and optionally a pharmaceutically acceptable salt thereof, is provided wherein n=3, Ar is 1,4-phenyl, R is $CH_3$, and X is $CH_2$. This compound is further identified herein as AGF312.

In a preferred embodiment of this invention, a compound of Formula I, and optionally a pharmaceutically acceptable salt thereof, is provided wherein n=3, Ar is 2,5-thienyl, R is H, and X is $CH_2$. This compound is further identified herein as AGF318.

In a preferred embodiment of this invention, a compound of Formula I, and optionally a pharmaceutically acceptable salt thereof, is provided wherein n=4, Ar is 2,5-thienyl, R is H, and X is $CH_2$. This compound is further identified herein as AGF320.

In a preferred embodiment of this invention, a compound of Formula I, and optionally a pharmaceutically acceptable salt thereof, is provided wherein n=3, Ar is 1,4-phenyl, R is H, and X is O. This compound is further identified herein as AGF323.

In a preferred embodiment of this invention, a compound of Formula I, and optionally a pharmaceutically acceptable salt thereof, is provided wherein n=2, Ar is 2,5-thienyl, R is H, and X is $CH_2$. This compound is further identified herein as AGF331.

In a preferred embodiment of this invention, a compound of Formula I, and optionally a pharmaceutically acceptable salt thereof, is provided wherein n=4, Ar is 1,4-phenyl, R is H, and X is $CH_2$. This compound is further identified herein as AGF299.

In a preferred embodiment of this invention, a compound of Formula I, and optionally a pharmaceutically acceptable salt thereof, is provided wherein n=2, Ar is 2'-fluoro-1,4-phenyl, R is H, and X is $CH_2$. This compound is further identified herein as AGF359.

In a preferred embodiment of this invention, a compound of Formula I, and optionally a pharmaceutically acceptable salt thereof, is provided wherein n=3, Ar is 2'-fluoro-1,4-phenyl, R is H, and X is $CH_2$. This compound is further identified herein as AGF347.

In a preferred embodiment of this invention, a compound of Formula I, and optionally a pharmaceutically acceptable salt thereof, is provided wherein n=4, Ar is 2'-fluoro-1,4-phenyl, R is H, and X is $CH_2$. This compound is further identified herein as AGF355.

In a preferred embodiment of this invention, a compound of Formula I, and optionally a pharmaceutically acceptable salt thereof, is provided wherein n is selected from one of the group of integers consisting of 1, 3, and 4, R is H, X is $CH_2$, and Ar is selected from one of the group consisting of (a) 1,4-phenyl, (b) 2'-fluoro-1,4-phenyl, and (c) 2,5-thienyl.

In a preferred embodiment of this invention, a compound of Formula I, and optionally a pharmaceutically acceptable salt thereof, is provided wherein n is selected from one of the group of integers consisting of 1, 2, 3, and 4, R is $CH_3$, X is $CH_2$, and Ar is selected from one of the group consisting of (a) 1,4-phenyl, (b) 2'-fluoro-1,4-phenyl, and (c) 2,5-thienyl.

In a preferred embodiment of this invention, a compound of Formula I, and optionally a pharmaceutically acceptable salt thereof, is provided wherein n is selected from one of the group of integers consisting of 2, 3, and 4, R is H, X is selected from one of the group consisting of O, S, NH, NHCHO, $NHCOCH_3$, and $NHCOCF_3$, and Ar is selected from one of the group consisting of (a) 1,4-phenyl, (b) 2'-fluoro-1,4-phenyl, and (c) 2,5-thienyl.

Another embodiment of this invention provides a pharmaceutical composition comprising a therapeutically effective amount of a compound of Formula I, and optionally a pharmaceutically acceptable salt thereof:

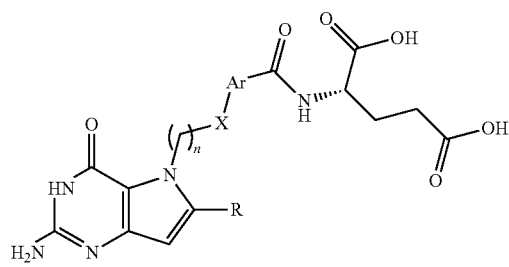

Formula I, wherein, R is selected from one of the group consisting of H and CH$_3$; n is an integer ranging from 1 to 4; X is selected from one of the group consisting of —CH$_2$—, O, S, —NH—, —NHCHO—, —NHCOCH$_3$—, and —NHCOCF$_3$—; and Ar is selected from one of the group consisting of (a) 1,4-phenyl, (b) 2'-fluoro-1,4-phenyl, and (c) 2,5-thienyl. Another embodiment of this invention provides the pharmaceutical composition having the compound of Formula I, as described herein, including a pharmaceutically acceptable carrier.

In another embodiment of this invention, a compound is provided of Formula II, and optionally a pharmaceutically acceptable salt thereof:

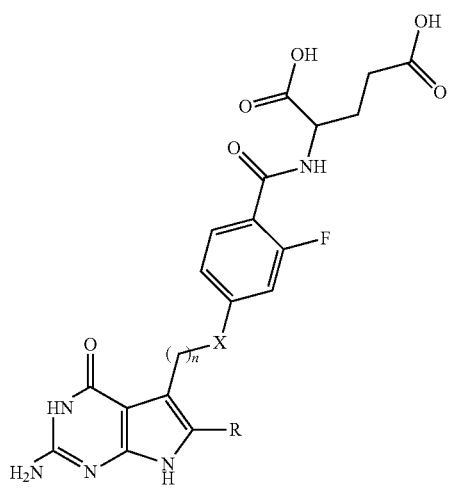

Formula II, wherein, R is selected from one of the group consisting of H and CH$_3$;

n is an integer ranging from 1 to 4; X is selected from one of the group consisting of —CH$_2$—, O, S, —NH—, —NHCHO—, —NHCOCH$_3$—, and —NHCOCF$_3$—. Those persons skilled in the art will appreciate that any of the combination(s) of the moieties identified for the groups of R, and X, and the integers identified for n, are embodiments of the present invention for any of the formula(ae) presented for Formula II.

In a preferred embodiment of this invention, a compound of Formula II, and optionally a pharmaceutically acceptable salt thereof, is provided wherein n is 3, R is H, X is CH$_2$. This compound is identified herein as AGF287.

In a preferred embodiment of this invention, a compound of Formula II, and optionally a pharmaceutically acceptable salt thereof, is provided wherein n is selected from one of the group of integers of 1, 2, and 4, R is H, and X is CH$_2$.

In a preferred embodiment of this invention, a compound of Formula II, and optionally a pharmaceutically acceptable salt thereof, is provided wherein n is selected from one of the group of integers of 1, 2, 3, and 4, R is CH$_3$, and X is CH$_2$.

In a preferred embodiment of this invention, a compound of Formula II, and optionally a pharmaceutically acceptable salt thereof, is provided wherein n is selected from one of the group of integers of 1, 2, 3, and 4, R is H, and X is selected from one of the group consisting of O, S, NH, NHCHO, NHCOCH$_3$, and NHCOCF$_3$.

Another embodiment of this invention provides a pharmaceutical composition comprising a therapeutically effective amount of a compound of Formula II, and optionally a pharmaceutically acceptable salt thereof:

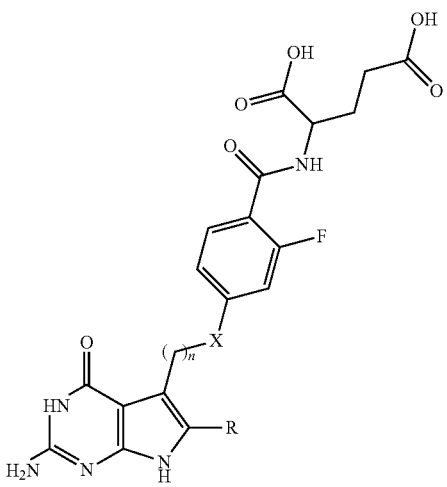

Formula II, wherein, R is selected from one of the group consisting of H and CH$_3$; n is an integer ranging from 1 to 4; X is selected from one of the group consisting of —CH$_2$—, O, S, —NH—, —NHCHO—, —NHCOCH$_3$—, and —NHCOCF$_3$—. A further embodiment of this invention provides a pharmaceutical composition having a compound of Formula II, as described herein, and including a pharmaceutically acceptable carrier.

Another embodiment of this invention provides a compound of Formula III, and optionally a pharmaceutically acceptable salt thereof:

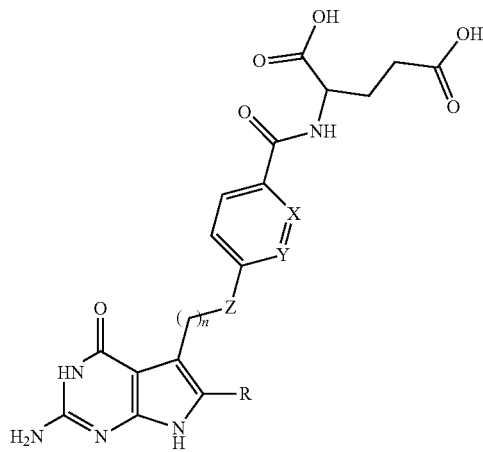

Formula III, wherein, R is selected from one of the group consisting of H and CH$_3$; n is an integer ranging from 1 to 4; X is selected from one of the group consisting of CH and N; Y is selected from one of the group consisting of CH and N; and Z is selected from one of the group consisting of —CH$_2$—, O, S, —NH—, —NHCHO—, —NHCOCH$_3$—, and —NHCOCF$_3$—. Those persons skilled in the art will appreciate that any of the combination(s) of the moieties identified for the groups of R, X, Y, and Z, and the integers identified for n, are embodiments of the present invention for any of the formula(ae) presented for Formula III.

In a preferred embodiment of this invention, a compound of Formula III, and optionally a pharmaceutically acceptable salt thereof, is provided wherein n is 2, and R is H, and X is either CH or N, Y is either CH or N, and Z is selected from one of the group consisting of $CH_2$, O, S, NH, NHCHO, $NHCOCH_3$, and $NHCOCF_3$. An example of this compound is identified herein as AGF315.

In a preferred embodiment of this invention, a compound of Formula III, and optionally a pharmaceutically acceptable salt thereof, is provided wherein n is 3, and R is H, and X is either CH or N, Y is either CH or N, and Z is selected from one of the group consisting of $CH_2$, O, S, NH, NHCHO, $NHCOCH_3$, and $NHCOCF_3$. An example of this compound is identified herein as AGF317.

In a preferred embodiment of this invention, a compound of Formula III, and optionally a pharmaceutically acceptable salt thereof, is provided wherein n is an integer selected from the group of 1, 2, 3, and 4, and R is H, and X is N, Y is CH, and Z is selected from one of the group consisting of $CH_2$, O, S, NH, NHCHO, $NHCOCH_3$, and $NHCOCF_3$.

In a preferred embodiment of this invention, a compound of Formula III, and optionally a pharmaceutically acceptable salt thereof, is provided wherein n is an integer selected from the group of 1, 2, 3, and 4, and R is H, and X is CH, Y is N, and Z is selected from one of the group consisting of $CH_2$, O, S, NH, NHCHO, $NHCOCH_3$, and $NHCOCF_3$.

In a preferred embodiment of this invention, a compound of Formula III, and optionally a pharmaceutically acceptable salt thereof, is provided wherein n is an integer selected from the group of 1, 2, 3, and 4, and R is $CH_3$, and X is N, Y is CH, and Z is selected from one of the group consisting of $CH_2$, O, S, NH, NHCHO, $NHCOCH_3$, and $NHCOCF_3$.

In a preferred embodiment of this invention, a compound of Formula III, and optionally a pharmaceutically acceptable salt thereof, is provided wherein n is an integer selected from the group of 1, 2, 3, and 4, and R is $CH_3$, and X is N, Y is CH, and Z is selected from one of the group consisting of $CH_2$, O, S, NH, NHCHO, $NHCOCH_3$, and $NHCOCF_3$.

Another embodiment of this invention provides a pharmaceutical composition comprising a therapeutically effective amount of a compound of Formula III, and optionally a pharmaceutically acceptable salt thereof:

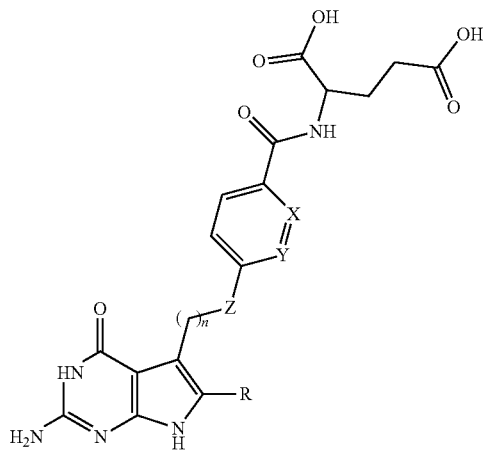

Formula III, wherein, R is selected from one of the group consisting of H and $CH_3$; n is an integer ranging from 1 to 4; X is selected from one of the group consisting of CH and N; Y is selected from one of the group consisting of CH and N; and Z is selected from one of the group consisting of $-CH_2-$, O, S, $-NH-$, $-NHCHO-$, $-NHCOCH_3-$, and $-NHCOCF_3-$. A further embodiment of this invention provides the pharmaceutical composition having the compound of Formula III, as described herein, and a pharmaceutically acceptable carrier.

Another embodiment of this invention provides a method of treating a patient having cancer comprising administering to said patient a therapeutically effective amount of a compound of Formula I, and optionally a pharmaceutically acceptable salt thereof:

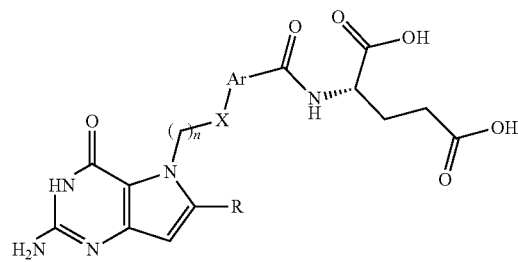

Formula I, wherein, R is selected from the group consisting of H and $CH_3$; n is an integer ranging from 1 to 4; X is selected from one of the group consisting of $-CH_2-$, O, S, $-NH-$, $-NHCHO-$, $-NHCOCH_3-$, and $-NHCOCF_3-$; and Ar is selected from one of the group consisting of (a) 1,4-phenyl, (b) 2'-fluoro-1,4-phenyl, and (c) 2,5-thienyl. A preferred embodiment of this invention provides a method of treating a patient having cancer comprising administering a therapeutically effective amount of at least one compound of Formula I selected from the group of AGF 291, AGF 299, AGF300, AGF307, AGF312, AGF318, AGF320, AGF323, AGF331, AGF 347, AGF 355, and AGF 359, and optionally a pharmaceutically acceptable salt thereof, to said patient.

Another embodiment of this invention provides a method of treating a patient having cancer comprising administering a therapeutically effective amount of a compound of Formula II, and optionally a pharmaceutically acceptable salt thereof:

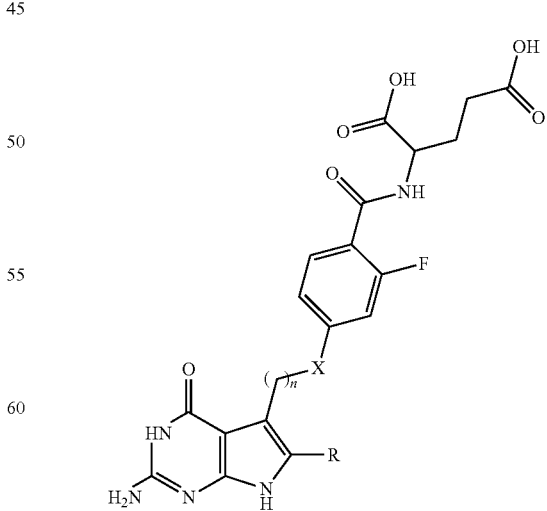

Formula II, wherein, R is selected from one of the group consisting of H and $CH_3$; n is an integer ranging from 1 to 4; and X is selected from one of the group consisting of —CH$_2$—, O, S, —NH—, —NHCHO—, —NHCOCH$_3$—, and —NHCOCF$_3$—. A preferred embodiment of this invention provides a method of treating a patient having cancer comprising administering a therapeutically effective amount of a compound of Formula II that is AGF287, and optionally a pharmaceutically acceptable salt thereof, to said patient.

Another embodiment of this invention provides a method of treating a patient having cancer comprising administering a therapeutically effective amount of a compound of Formula III, and optionally a pharmaceutically acceptable salt thereof:

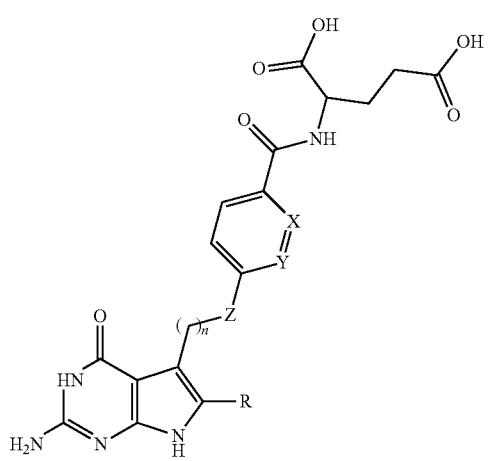

Formula III, wherein, R is selected from one of the group consisting of H and CH$_3$; n is an integer ranging from 1 to 4; X is selected from one of the group consisting of CH and N; Y is selected from one of the group consisting of CH and N; and Z is selected from one of the group consisting of —CH$_2$—, O, S, —NH—, —NHCHO—, —NHCOCH$_3$—, and —NHCOCF$_3$—. A preferred embodiment of this invention provides a method of treating a patient having cancer comprising administering a therapeutically effective amount of at least one compound of Formula III selected from the group of AGF 315 and AGF 317, and optionally a pharmaceutically acceptable salt thereof, to said patient.

Another embodiment of this invention provides a method of targeting mitochondrial metabolism comprising administering to a cancer patient an effective amount of at least one compound selected from the group of Formula I, and optionally a pharmaceutically acceptable salt thereof, of Formula II, and optionally a pharmaceutically acceptable salt thereof, and of Formula III, and optionally a pharmaceutically acceptable salt thereof:

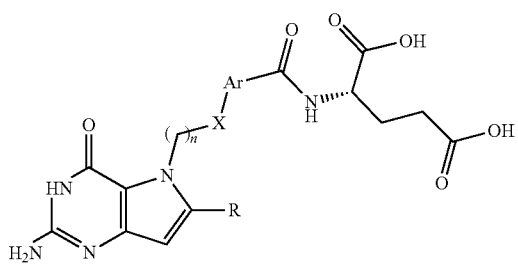

Formula I, wherein, R is selected from one of the group consisting of H and CH$_3$; n is an integer ranging from 1 to 4; X is selected from one of the group consisting of —CH$_2$—, O, S, —NH—, —NHCHO—, —NHCOCH$_3$—, and —NHCOCF$_3$—; and Ar is selected from one of the group consisting of (a) 1,4-phenyl, (b) 2'-fluoro-1,4-phenyl, and (c) 2,5-thienyl; and

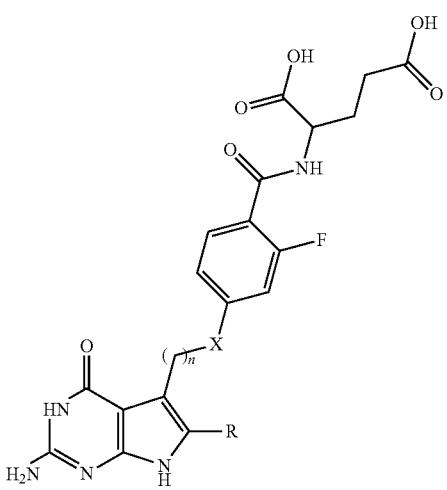

Formula II, wherein, R is selected from one of the group consisting of H and CH$_3$; n is an integer ranging from 1 to 4; and X is selected from one of the group consisting of —CH$_2$—, O, S, —NH—, —NHCHO—, —NHCOCH$_3$—, and —NHCOCF$_3$—; and

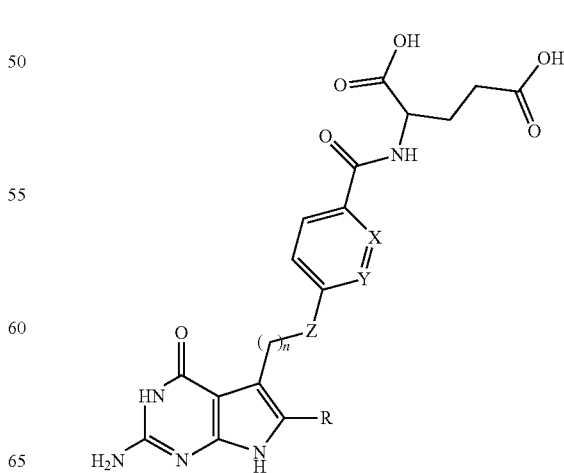

Formula III, wherein R is selected from one of the group consisting of H and CH₃; n is an integer ranging from 1 to 4; X is selected from one of the group of CH and N; Y is selected from one of the group of CH and N; and Z is selected from one of the group consisting of —CH₂—, O, S, —NH—, —NHCHO—, —NHCOCH₃—, and —NHCOCF₃—.

Another embodiment of this invention provides a method of targeting SHMT2 and MTHFD2 comprising administering to a cancer patient an effective amount of at least one compound selected from the group of Formula I, and optionally a pharmaceutically acceptable salt thereof, of Formula II, and optionally a pharmaceutically acceptable salt thereof, and of Formula III, and optionally a pharmaceutically acceptable salt thereof:

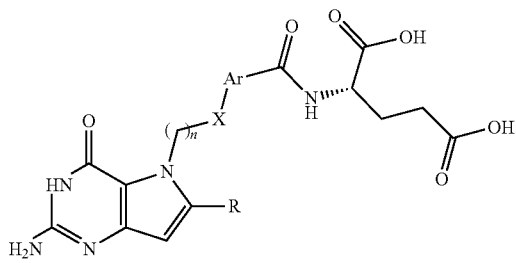

Formula I, wherein, R is selected from one of the group consisting of H and CH₃; n is an integer ranging from 1 to 4; X is selected from one of the group consisting of —CH₂—, O, S, —NH—, —NHCHO—, —NHCOCH₃—, and —NHCOCF₃—; and Ar is selected from one of the group consisting of (a) 1,4-phenyl, (b) 2'-fluoro-1,4-phenyl, and (c) 2,5-thienyl; and

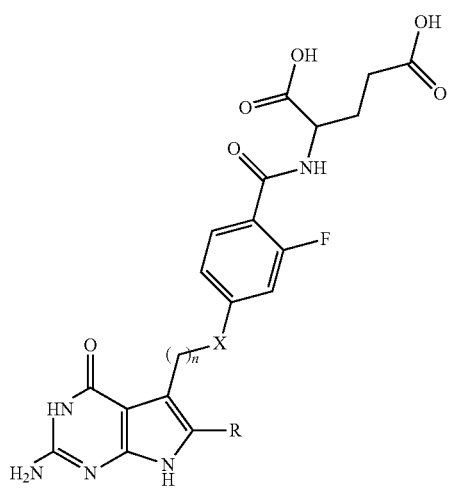

Formula II, wherein, R is selected from one of the group consisting of H and CH₃; n is an integer ranging from 1 to 4; and X is selected from one of the group consisting of —CH₂—, O, S, —NH—, —NHCHO—, —NHCOCH₃—, and —NHCOCF₃—; and

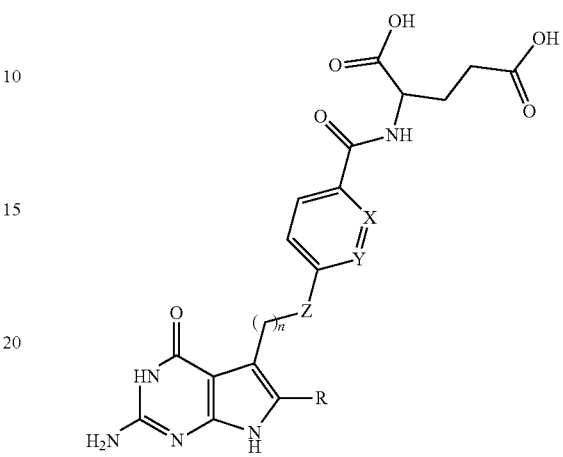

Formula III, wherein R is selected from the group consisting of H and CH₃; n is an integer ranging from 1 to 4; X is selected from one of the group consisting of CH and N; Y is selected from one of the group consisting of CH and N; and Z is selected from one of the group consisting of —CH₂—, O, S, —NH—, —NHCHO—, —NHCOCH₃—, and —NHCOCF₃—.

Those skilled in the art shall understand that chemical structures of Formulae I, II, and III, are preferred examples of the compounds of this invention and that tautomers of Formulae I, II, and III are also embodiments of compounds of Formula I, Formula II, and Formula III, respectively. Those skilled in the art understand that chemical structures are often drawn as one tautomeric form over another. This invention provides for several tautomeric forms of the oxygen attached at the fourth carbon of the pyrimidine six membered ring of the compounds of this invention. The tautomeric forms (i.e. oxygen with double bond, or —OH) provide additional structural embodiments that will be appreciated by those skilled in the art.

In certain embodiments of the invention, the novel compounds include Formula I, Formula II, and Formula III, as described herein, and include pharmaceutically acceptable salts of these compounds, and include for example but not limited to, hydrochloride chloride (HCl) salts (or other acids) of these compounds.

It is especially advantageous to formulate parenteral compositions in dosage unit form for ease of administration and uniformity of dosage. Dosage unit form as used herein refers to physically discrete units suited as unitary dosages for the patients being treated, each unit containing a predetermined quantity or effective amount of a compound of the present invention to produce the desired effect in association with a pharmaceutical carrier. The specification for the dosage unit forms of the invention are dictated by and directly dependent on the particular compound and the particular effect, or therapeutic response, that is desired to be achieved.

Compounds of Formula I, II, or III, or pharmaceutically acceptable salts, or hydrates thereof, can be administered to a patient (an animal or human) via various routes including parenterally, orally or intraperitoneally. Parenteral administration includes the following routes that are outside the alimentary canal (digestive tract): intravenous; intramuscular; interstitial, intraarterial; subcutaneous; intraocular; intracranial; intraventricular; intrasynovial; transepithelial, including transdermal, pulmonary via inhalation, ophthalmic, sublingual and buccal; topical, including dermal, ocular, rectal, or nasal inhalation via insufflation or nebulization. Specific modes of administration shall depend on the indication. The selection of the specific route of administration and the dose regimen is to be adjusted or titrated by the clinician according to methods known to the clinician in order to obtain the optimal clinical response. The amount of compound to be administered is that amount which is therapeutically effective. The dosage to be administered to a patient shall depend on the characteristics of the patient being treated, including for example, but not limited to, the patient's age, weight, health, and types and frequency of concurrent treatment, if any, of any other chemotherapeutic agent(s), all of which is determined by the clinician as one skilled in the art.

Compounds of Formula I, II, or III, or a pharmaceutically acceptable salt, or hydrate thereof, that are orally administered can be enclosed in hard or soft shell gelatin capsules, or compressed into tablets. Compounds also can be incorporated with an excipient and used in the form of ingestible tablets, buccal tablets, troches, capsules, sachets, lozenges, elixirs, suspensions, syrups, wafers and the like. Compounds of Formula I, II, or III can be in the form of a powder or granule, a solution or suspension in an aqueous liquid or non-aqueous liquid, or in an oil-in-water emulsion.

The tablets, troches, pills, capsules and the like also can contain, for example, a binder, such as gum tragacanth, acacia, corn starch; gelating excipients, such as dicalcium phosphate; a disintegrating agent, such as corn starch, potato starch, alginic acid and the like; a lubricant, such as magnesium stearate; a sweetening agent, such as sucrose, lactose or saccharin; or a flavoring agent. When the dosage unit form is a capsule, it can contain, in addition to the materials described above, a liquid carrier. Various other materials can be present as coatings or to otherwise modify the physical form of the dosage unit. For example, tablets, pills, or capsules can be coated with shellac, sugar or both. A syrup or elixir can contain the active compound, and sucrose as a sweetening agent, methyl and propylparabens as preservatives, a dye and flavoring, for example. Any material used in preparing any dosage unit form should be pharmaceutically pure and substantially non-toxic. Additionally, the compounds of Formulae I, II, and III, or a pharmaceutically acceptable salt, or hydrate of the compounds of Formulae I, II, and III, can be incorporated into sustained-release preparations and formulations.

The compounds of Formula I, Formula II, or Formula III, or a pharmaceutically acceptable salt, or hydrate thereof, can be administered to the central nervous system, parenterally or intraperitoneally. Solutions of the compound as a free base or a pharmaceutically acceptable salt can be prepared in water mixed with a suitable surfactant, such as for example, but not limited to, hydroxypropylcellulose. Dispersions also can be prepared in glycerol, liquid polyethylene glycols and mixtures thereof, and in oils. Under ordinary conditions of storage and use, these preparations can contain a preservative and/or antioxidants to prevent the growth of microorganisms or chemical degeneration.

The pharmaceutical forms suitable for injectable use include, without limitation, sterile aqueous solutions or dispersions and sterile powders for the extemporaneous preparation of sterile injectable solutions or dispersions. In all cases, the form must be sterile and must be fluid to the extent that easy syringability exists. It can be stable under the conditions of manufacture and storage and must be preserved against the contaminating action of microorganisms, such as bacteria and fungi.

Compounds of the present invention may be contained within, mixed with, or associated with, a suitable (acceptable) pharmaceutical carrier for administration to a patient according to the particular route of administration desired. Suitable or acceptable pharmaceutical carriers refer to any pharmaceutical carrier that will solubilize the compounds of the present invention and that will not give rise to incompatability problems, and includes any and all solvents, dispersion media, coatings, antibacterial and antifungal agents, isotonic agents, absorption delaying agents, and the like. The use of such suitable or acceptable pharmaceutical carriers is well known by those skilled in the art. Preferred carriers include sterile water, physiologic saline, and five percent dextrose in water. Examples of other suitable or acceptable pharmaceutical carriers include, but are not limited to, ethanol, polyol (such as propylene glycol and liquid polyethylene glycol), suitable mixtures thereof, or vegetable oils. The proper fluidity can be maintained, for example, by the use of a coating, such as lecithin, by the maintenance of the required particle size (in the case of a dispersion) and by the use of surfactants. The prevention of the action of microorganisms can be brought about by various antibacterial and anti-fungal agents, for example, parabens, chlorobutanol, phenol, sorbic acid, thimerosal, and the like. In many cases, it will be preferable to include isotonic agents, for example, sugars or sodium chloride.

Sterile injectable solutions are prepared by incorporating a compound of Formula I, II, or III, in the required amount in the appropriate solvent with various of the other ingredients enumerated above, as required, followed by filtered sterilization. Generally, dispersions are prepared by incorporating the sterilized compound of Formula I, II, or III, into a sterile vehicle that contains the basic dispersion medium and any of the other ingredients from those enumerated above. In the case of sterile powders for the preparation of sterile injectable solutions, the preferred methods of preparation are vacuum drying and freeze drying.

Pharmaceutical compositions which are suitable for administration to the nose and buccal cavity include, without limitation, self-propelling and spray formulations, such as aerosol, atomizers and nebulizers.

The therapeutic compounds of Formula I, II, or III, as described herein, can be administered to a patient alone or in combination with pharmaceutically acceptable carriers or as pharmaceutically acceptable salts, or hydrates thereof, the proportion of which is determined by the solubility and chemical nature of the compound, chosen route of administration to the patient and standard pharmaceutical practice.

The present invention is more particularly described in the following non-limiting examples, which are intended to be illustrative only, as numerous modifications and variations therein will be apparent to those skilled in the art.

EXAMPLES

Figure 6:
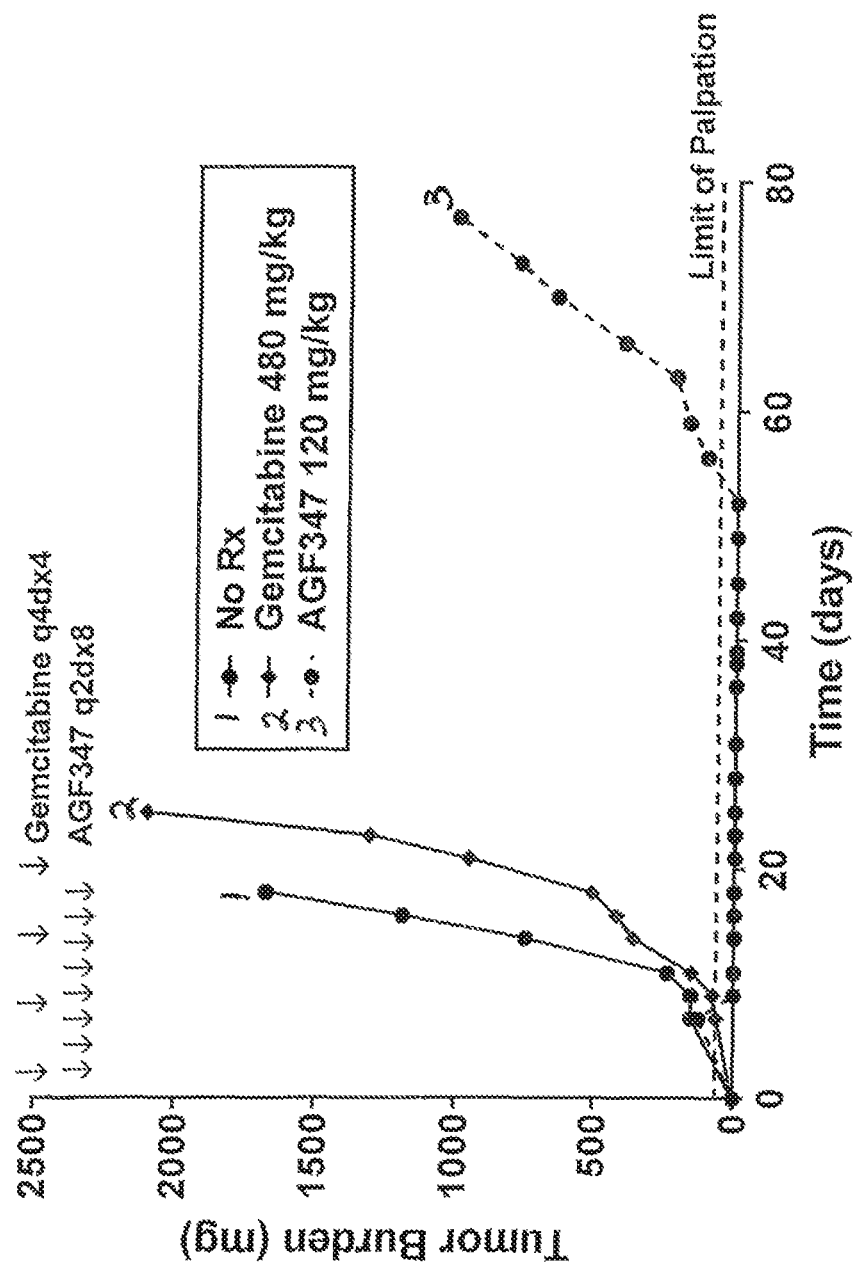
FIG. 6 shows in vivo efficacies of the compound of this invention AGF347 and GEM (background art compound) toward the MIA PaCa-2 PaC xenografts. Female ICR SCID mice (10 weeks old; 19 g average body weight) were implanted bilaterally with human MIA PaCa-2 PaC tumors. Beginning on day 3 following subcutaneous implantation, the mice were dosed as follows: AGF347, Q2d×8 at 15 mg/kg/inj, total dose 120 mg/kg; and GEM, Q4d×4 at 120 mg/kg/inj, total dose 480 mg/kg). T/C values were 19% for AGF291 and 26% for GEM. For AGF347, the T−C (1000 mg) was 54 days and 1/5 mice was disease-free at 122 days.
Figure 8:
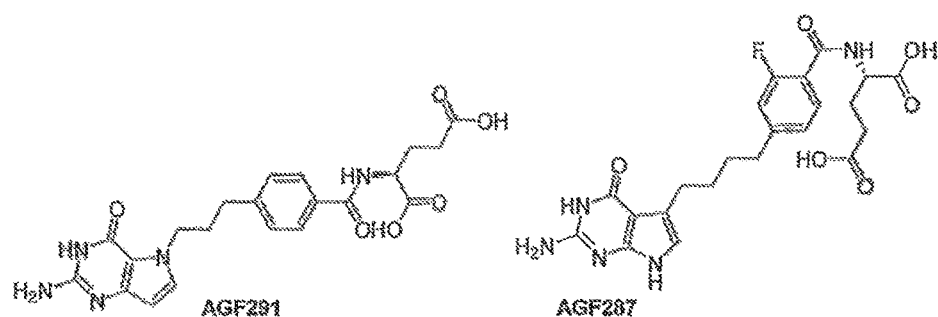
FIG. 8 shows resulting data for 5N-substituted pyrrolo[3,2-d]pyrimidine compounds, namely AGF291 and AGF287, of the present invention.

Animal studies indicate in-vivo potent antitumor activity against pancreatic cancer in mice for compound of the present invention identified by AGF291. The preliminary results provided herein include pancreatic cancer data for AGF287 and AGF291. FIG. 6 shows data for growth inhibitions by 5- and 6-substituted pyrrolo[2,3-d]- and pyrrolo[3,2-d]pyrimidine compounds of this invention, compared to gemcitabine (GEM) toward pancreatic cancer cell lines expressing the major facilitative folate transporters. Additional results and data are shown in FIGS. 5, 6, 8, and 11.

Other embodiments of the invention will be apparent to those skilled in the art from consideration of the specification and practice of the invention disclosed herein. It is intended that the specification be considered as exemplary only. Furthermore, the examples are meant to be illustrative of certain embodiments of the invention and are not intended to be limiting as to the scope of the invention.

Genes encoding one-carbon (C1) metabolism enzymes in the mitochondria and cytosol are consistently upregulated across multiple cancer types. Whereas multi-targeted cytosolic C1 metabolism inhibitors such as pemetrexed are used clinically, there are no current anti-cancer drugs that target upstream mitochondrial C1 metabolism. The present invention provides novel, multi-targeted small molecule inhibitors of mitochondrial C1 metabolism at serine hydroxymethyltransferase (SHMT) 2, and cytosolic C1-dependent purine biosynthesis (5-aminoimidazole-4-carboxamide ribonucleotide formyltransferase and glycinamide ribonucleotide formyltransferase) and SHMT1 as broad-spectrum antitumor agents toward lung, colon and pancreatic tumors. In vivo anti-tumor efficacy is demonstrated in a pancreas cancer model. The compounds and pharmaceutically acceptable salts thereof are dual-targeting mitochondrial and cytosolic C1 metabolism for cancer. The compounds and pharmaceutically acceptable salts there of the present invention overcome resistance to current anticancer therapies.

Folate-dependent one-carbon (C1) metabolism is compartmentalized in the mitochondria and cytosol and supports cell growth through nucleotide and amino acid biosynthesis. Mitochondrial C1 metabolism including serine hydroxymethyltransferase (SHMT) 2 provides glycine, NAD(P)H, and C1 units for cytosolic biosynthetic reactions, and is implicated in the oncogenic phenotype across a wide range of cancers. Whereas multi-targeted inhibitors of cytosolic C1 metabolism such as pemetrexed are used clinically, there are currently no anticancer drugs that specifically target upstream mitochondrial C1 metabolism. We used molecular modeling to design novel small-molecule pyrrolo[3,2-d]pyrimidine inhibitors targeting mitochondrial C1 metabolism at SHMT2 as potential broad-spectrum antitumor agents. In vitro antitumor efficacy was established with the lead compounds of the present invention, namely, AGF291, AGF320, AGF347, toward lung, colon, and pancreatic cancer models. Intracellular targets were identified by glycine/nucleoside protection and targeted metabolomics with an isotope tracer, with confirmation by in vitro assays with purified enzymes. In addition to targeting SHMT2, inhibition of the purine biosynthetic enzymes, 5-aminoimidazole-4-carboxamide ribonucleotide formyltransferase and/or glycinamide ribonucleotide formyltransferase, and SHMT1 in the cytosol was established. The compounds and pharmaceutically acceptable salts thereof of the present invention have first-in-class in vivo antitumor efficacy with compound AGF291 toward the MIA PaCa-2 pancreatic adenocarcinoma xenograft model in severe-combined immunodeficient mice, providing compelling proof-of-concept of the therapeutic potential of multi-targeting SHMT2 and cytosolic C1 enzymes by the series of compounds of the present invention. Our results provide structure-activity relationships and identify novel drug compounds for further development as multi-targeted anti-tumor agents with impressive potential to overcome resistance to current therapies.

The present invention provides a novel series of 5-substituted pyrrolo[3,2-d]pyrimidine antifolate analogs with primary inhibition of SHMT2, and secondary inhibition of AICARFTase and/or GARFTase, as well as of SHMT1. Direct inhibition of de novo purine biosynthesis downstream of SHMT2 is potentiated by loss of mitochondrial C1 metabolism, resulting from primary SHMT2 inhibition, reflecting the impact of limiting glycine and 10-formyl-THF. The present invention provides novel compounds, such as for example, AGF291, AGF320, and AGF347, with broad-spectrum in vitro anti-tumor efficacies including H460 non-small cell lung cancer (NSCLC), HCT116 colon cancer, and MIA PaCa-2 pancreatic cancer (PaC) cells. For AGF291, in vitro findings were extended in vivo to MIA PaCa-2 tumor xenografts in severe compromised immunodeficient (SCID) mice, providing compelling proof-of-concept of the therapeutic potential of multi-targeted SHMT2 therapeutics for cancer.

Table 1 shows the results of in vitro assays, N-terminally His-tagged proteins were purified including GARFTase (transformylase domain; residues 100-302), ATIC (AICAR-FTase/IMP cyclohydrolase), SHMT2 and MTHFD2. For SHMT2, a coupled SHMT2-MTHFD2 assay was used with an NADH readout. There was no inhibition of MTHFD2 by the analogs. AGF291 and AGF320 (as monoglutamates) inhibited SHMT2 ($K_i$s of 0.82 and 0.28 µM, respectively). (AGF347 and AGF359,

TABLE 1

$K_I$ values (µM) for in vitro inhibition of the indicated folate metabolic enzymes by pyrrolopyrimidine compounds.

| | $K_i$ (µM) | | | |
|---|---|---|---|---|
| Analog | SHMT2 | GARFTase | AICARFTase | MTHFD2 |
| AGF291 | 0.82 ± 0.49 | Not detected | 10.91 ± 6.07 | Not detected |
| AGF320 | 0.28* | 0.33 ± 0.22 | 6.96 ± 4.98 | Not detected |
| AGF347 | ND | 3.13 ± 0.66 | 3.72 ± 1.61 | Not detected |
| AGF94 | ND | 0.47 ± 0.11 | Not detected | ND |

"Not detected" means no inhibition was detected up to 100 µM.
"ND" means not determined.
*designates one experiment.

testing ongoing). We also assayed inhibition of GARFTase and AICARFTase by AGF291, AGF320, and AGF347 (76, 77). For GARFTase and AICARFTase, inhibition by AGF291, AGF320 and AGF347 paralleled that measured by metabolomics assays. These results confirm that SHMT2 and the purine biosynthetic enzymes GARFTase and AICARFTase are direct targets of our lead pyrrolo[3,2-d]pyrimidine compounds.

Table 2 provides proliferation results for engineered CHO and human tumor cells. Proliferation assays were performed with engineered Chinese hamster ovary (CHO) cell lines R2 (transporter-null), PC43-10 (expresses RFC only), RT16 (FRα only), and R2/PCFT4 (PCFT only) cultured in folate-/glycine-free RPMI1640 supplemented with 25 nM leucovorin. Additional results are shown for HCT116 (colon tumor cells (CTC)), IGROV1 (epithelial ovarian cancer (EOC) cells), H460 (non-small cell lung cancer (NSCLC) cells), MIA PaCa-2 (pancreatic cancer (PaC) cells), and HPAC (PaC). Results are shown as mean IC50s (±standard deviation; n=4).

TABLE 2

Proliferation results for engineered CHO and human tumor cells.

Figure 2:
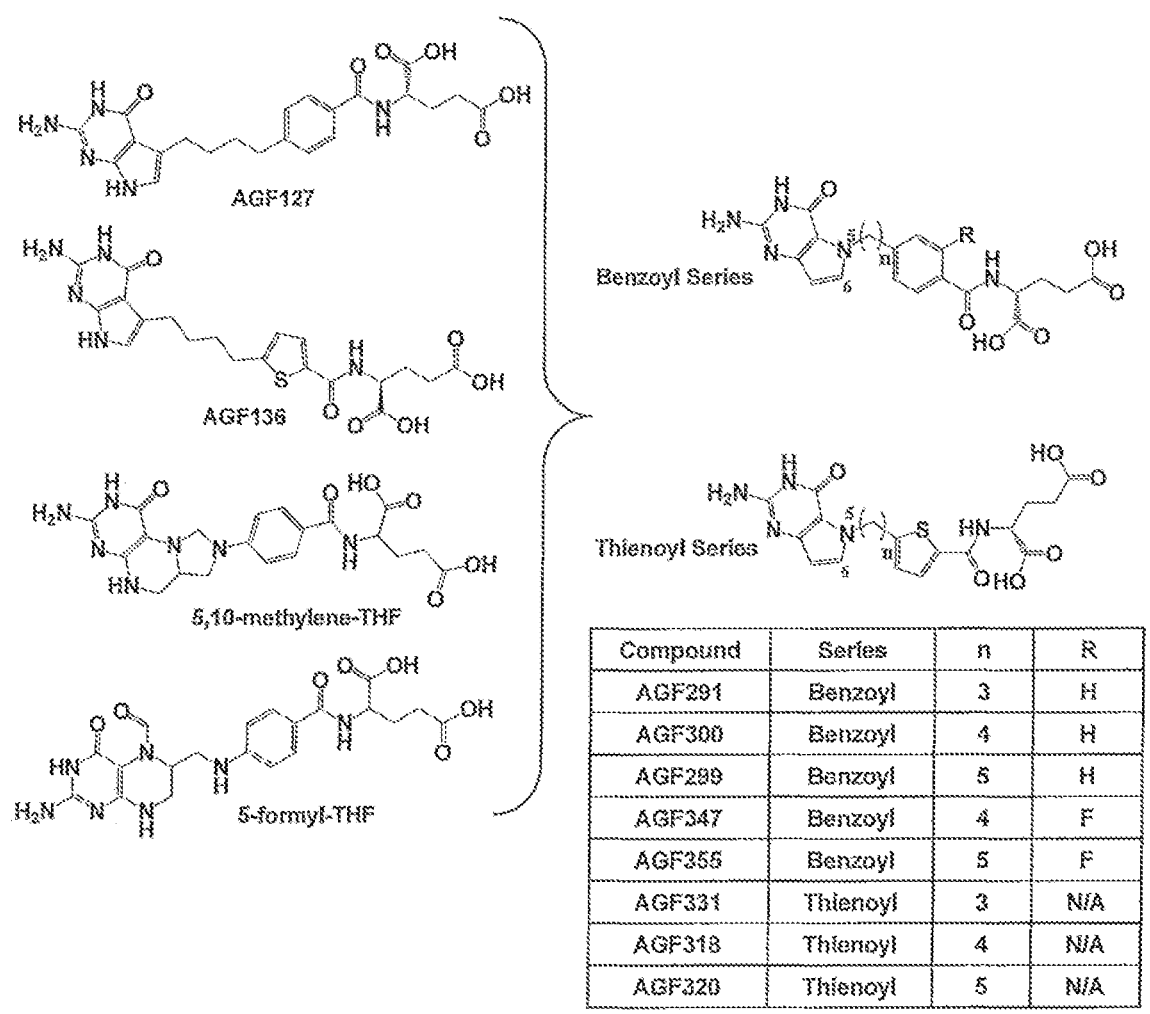
FIG. 2 shows the design of novel 5-substituted pyrrolo [3,2-d]pyrimidine benzoyl and thienoyl compounds of this invention, namely, identified as compounds AGF 291, AGF 300, AGF 299, AGF347, AGF 355, AGF 331, AGF 318, and AGF 320. In the table are summarized key structural features for the various compounds of the present invention, including the bridge lengths identified by "n" in FIG. 2 (3, 4, or 5 carbons), thienoyl or benzoyl side-chains, and for the latter, the 2' ring substituent (F or H). N/A is an abbreviation for and means not applicable.

| | | | | IC50s (SE) (nMolar) | | | |
|---|---|---|---|---|---|---|---|
| Compound | Series FIG. 2 | n | R | R2 (null) (CHO) | PC43-10 (RFC) (CHO) | RT16 (FR alpha) (CHO) | R2/PCFT4 (CHO) |
| AGF291 | Benzoyl | 3 | H | >1000 | 454 (87) | 117 (10) | 282 (23) |
| AGF320 | Thienoyl | 5 | NA | >1000 | >1000 | 156 (18) | 694 (56) |
| AGF347 | Benzoyl | 4 | F | >1000 | 224 (17) | 9.4 (0.1) | 479 (64) |
| AGF359 | Benzoyl | 3 | F | >1000 | 233 (25) | 525 (229) | 98 (17) |

| | IC50s (SE) (nMolar) | | | | |
|---|---|---|---|---|---|
| Compound | HCT116 (CTC) | IGROV1 (EOC) | H460 (NSCLC) | MIA PaCa-2 (PaC) | HPAC (PaC) |
| AGF291 | 2266 (450) | 443 (88) | 461 (163) | 3664 (721) | 301 (22) |
| AGF320 | 737 (195) | 401 (140) | 573 (145) | 2266 (400) | 190 (21) |
| AGF347 | 437 (180) | 62 (43) | 214 (88) | 1381 (182) | 764 (73) |
| AGF359 | ND | 229 (37) | ND | >1000 | 167.45 (20.45) |

Abbreviations:
CHO, Chinese hamster ovary;
EOC, epithelial ovarian cancer;
NSCLC, non-small cell lung cancer;
PaC, pancreatic cancer Design of 5-substituted pyrrolo[3,2-d]pyrimidine antifolates of the present invention targeting mitochondrial C1 metabolism at SHMT2 is provided herein. Given the association of mitochondrial C1 metabolism with malignancy (14-17), including reports of SHMT2 as a potential "onco-driver" (15, 22), it was of interest to develop inhibitors of SHMT2 as potential antitumor agents. We initially looked for potential SHMT2 inhibitors among the known arsenal of classic antifolates (including methotrexate, pemetrexed, raltitrexed and lometrexol) (6-8) and previous GARFTase and AICARFTase inhibitors from published studies (23-29). We tested these compounds for inhibition of proliferation of Chinese hamster ovary (CHO) cells engineered from a folate transporter-null (MTXRIIOua$^R$2-4) CHO subline (hereafter, R2) (30) to express human PCFT (R2/PCFT4) (24), as we reasoned that tumor-selective uptake of a putative SHMT2 inhibitor by PCFT (31) would be desirable. Since inhibition of mitochondrial C1 metabolism (at SHMT2) would be expected to induce glycine auxotrophy, as seen in SHMT2 KO (KO) cells (20), and mitochondrial C1 metabolism generates C1 units (i.e., formate) critical for downstream nucleotide biosynthesis, these experiments were performed in glycine- and nucleoside-free media, and the protective effects of added glycine (130 µM), adenosine (60 µM), and/or thymidine (10 µM) were determined. All these compounds inhibited cell proliferation and nucleotide biosynthesis (reflected in adenosine and/or thymidine protection), however, glycine was not protective with or without nucleoside additions. Thus, the known compounds of the background art were not useful. We are aware of the structural features of our previous 5-substituted pyrrolo[2,3-d]pyrimidine benzoyl and thienoyl compounds (28, 32) and with those of 5,10-methylene-THF (SHMT2 product) and 5-formyl-THF (SHMT inhibitor) (33), see FIG. 2. The present invention provides 5-substituted pyrrolo[3,2-d]pyrimidine compounds and includes 3-5 bridge carbons linked to benzoyl, namely compounds of the present invention identified herein as AGF291, AGF300, and AGF299, or thienoyl, namely the compounds of the present invention identified herein as AGF331, AGF318, and AGF320. Further, the present invention provides compounds having a 2' fluorine substitution for increasing the inhibitory potencies of pyrrolo[2,3-d]pyrimidine compounds, such as for example, the 2'-fluorinated compounds of the present invention identified as AGF300 and AGF299, as well as AGF347 and AGF355. All compounds, described, were docked into human SHMT2 (see FIGS. 12A-12D) and docking scores (see Table S1) were better than for the previously reported pyrazolopyran inhibitor SHIN1 (21) (−5.58 kcal/mol) upon re-docking.

TABLE S1

Docking scores of antifolates for intracellular drug targets (kcal/mol)

| Compound | SHMT2 | SHMT1 |
|---|---|---|
| AGF291 | −7.69 | −10.45 |
| AGF300 | −7.58 | −7.17 |
| AGF299 | −7.42 | −7.48 |
| AGF347 | −10.06 | −8.90 |
| AGF355 | −6.55 | −6.45 |
| AGF331 | −6.93 | −7.19 |
| AGF318 | −6.43 | −7.03 |
| AGF320 | −8.32 | −11.14 |

Molecular modeling was performed for all analogs with the structure of human SHMT2 (PDB: 5V7I) (1) and for rabbit SHMT1 (PDB: 1LS3) (2), using the induced fit docking protocol of Maestro (44, 45).

Discovery of 5-substituted pyrrolo[3,2-d]pyrimidine antifolates of the present invention which target mitochondrial C1 metabolism. We synthesized the novel compounds (see below synthesis schemes) and screened these compounds for inhibition of cell proliferation. We initially assessed inhibition by these compounds (from 0 to 1000 nM) toward PCFT-expressing R2/PCFT4 CHO cells and an isogenic CHO subline engineered to express human RFC (PC43-10) (23). Results were compared to those for folate transporter-null R2 CHO cells as a negative control. IC$_{50}$ values for "active" compounds are shown in FIG. 6 for each of the compounds of the present invention, along with those for AGF94 (a "pure" GARFTase inhibitor) (27). Active compounds of the present invention toward R2/PCFT4 and PC43-10 cells included AGF291, AGF320, AGF331 and AGF347, with AGF291 showing selectivity (~1.6-fold) toward PCFT over RFC. These compounds were further tested with human tumor cell lines, including H460 NSCLC, HCT116 colon cancer, and MIA PaCa-2 PaC cells, characterized by expression of PCFT and RFC, but not FRα (34, 35) (see FIG. 13). $IC_{50}$ values for growth inhibition are in FIG. 6. Although there were notable differences in drug sensitivities among the assorted tumor models, the compounds identified by AGF291, AGF320 and AGF347 were consistently the most active.

Figure 1:
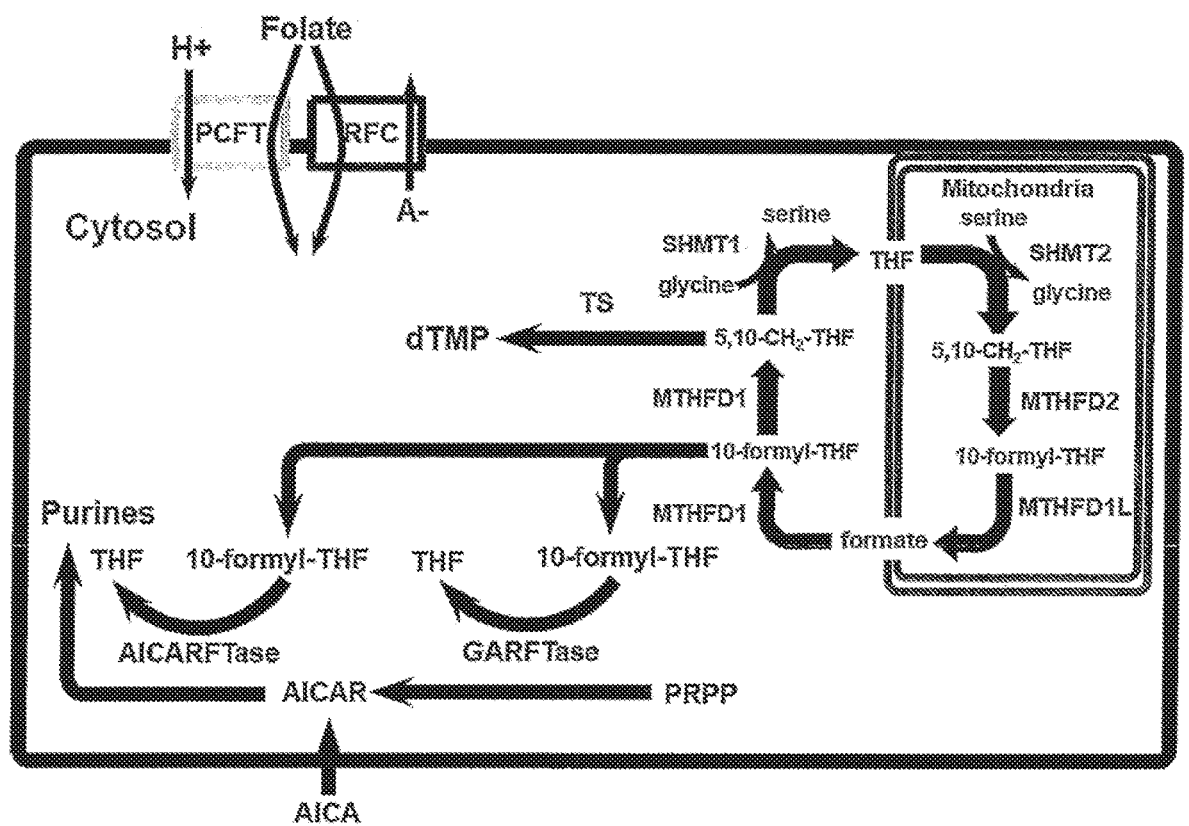
FIG. 1 shows C1 metabolism is compartmentalized in the cytosol and the mitochondria. Folates (and folate analogs) enter the cell through plasma membrane facilitated folate transporters, PCFT and RFC. Serine catabolism in the mitochondria beginning with SHMT2 generates glycine and formate, the latter of which is required for downstream cytosolic de novo purine nucleotide biosynthesis (by GARFTase and AICARFTase) in its 10-formyl-THF form and thymidylate biosynthesis following conversion to 5,10-methyene-THF (5,10-$CH_2$-THF) by MTHFD1. SHMT1 catalyzes the conversion of glycine to serine in the cytosol. AICA is metabolized to AICAR (ZMP), the AICARFTase substrate which circumvents GARFTase. The arrows in FIG. 1 denote the net flux of C1 metabolism, however, most reactions in the serine/glycine cycle are reversible.
Figure 3:
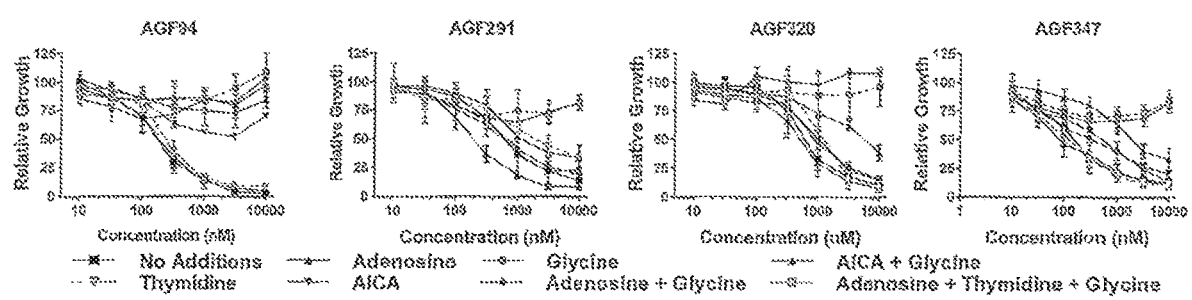
FIG. 3 shows the in vitro antitumor efficacy and identification of targeted pathways and enzymes by novel pyrrolopyrimidine compounds in H460 tumor cells. Dose-response curves are shown for AGF94, an established GARFTase inhibitor (27) and the novel compounds AGF291, AGF320, and AGF347 without additions, or in the presence of adenosine (60 AICA (320 thymidine (10 μM) and/or glycine (130 μM). The results are mean values+/− standard deviations for 3 biological replicates.

We again used glycine/nucleoside protection studies (above) in H460, HCT116, IGROV1 and MIA PaCa-2 cells treated with AGF291, AGF320, or AGF347 to identify the targeted pathways. The results were compared to those for AGF94 and are shown in FIG. 3 for H460 cells. Adenosine (60 μM) was fully protective up to 10 μM AGF94, whereas glycine (130 μM) had no effect. We also tested the protective effects of AICA (320 μM) which is metabolized to AICAR (ZMP) (AICARFTase substrate), thus circumventing the GARFTase step in de novo purine biosynthesis (27) (see FIG. 1). As AICA was completely protective, GARFTase must be the intracellular target for AGF94 (27). For AGF291, AGF347, and AGF320, neither glycine nor adenosine alone was fully protective. However, combined adenosine and glycine was substantially protective for all compounds (see FIG. 3). These results strongly suggest that these compounds of the present invention target both mitochondrial C1 metabolism and cytosolic de novo purine biosynthesis. Thymidine provided no protection from any of the compounds and did not increase the extent of protection by glycine and adenosine. For some of the compounds, notably AGF320, growth inhibition was modestly (and incompletely) reversed by AICA (with glycine) (see FIG. 3), suggesting a secondary intracellular target, most likely GARFTase. Analogous results were obtained with HCT116 and MIA PaCa-2 tumor cells (see FIG. 14).

Collectively, these results establish that the compounds of the present invention, namely, AGF291, AGF320, and AGF347 target both mitochondrial and cytosolic C1 metabolism.

Identification of the Mitochondrial Enzyme Target for AGF291, AGF320, and AGF347 by Targeted Metabolomics.

To further confirm the intracellular enzyme targets of the lead compounds of this invention, namely, AGF291, AGF320, and AGF347, we performed targeted metabolomics with liquid chromatography-mass spectrometry (LC-MS) and [2,3,3-$^2$H]serine tracer in HCT116, H460 and MIA PaCa-2 tumor cells. The cells were processed for LC-MS analyses of total serine, and of M+3, M+2, M+1, and M+0 (unlabeled) serine (where M+n represents species with n deuterium atoms). The results with the drug-treated cells were compared to those for untreated cells. For WT HCT116 cells, the results were compared to those for SHMT2 KO, MTHFD2 KO, and SHMT1 KO cells (KO of SHMT2, MTHFD2, and SHMT1, respectively (20)). For H460 cells, controls included non-targeted control (NTC) and SHMT2 shRNA knockdown (KD) cells.

Figures 4A, 4B, 4C, 4D, 4E, 4F, 4G:
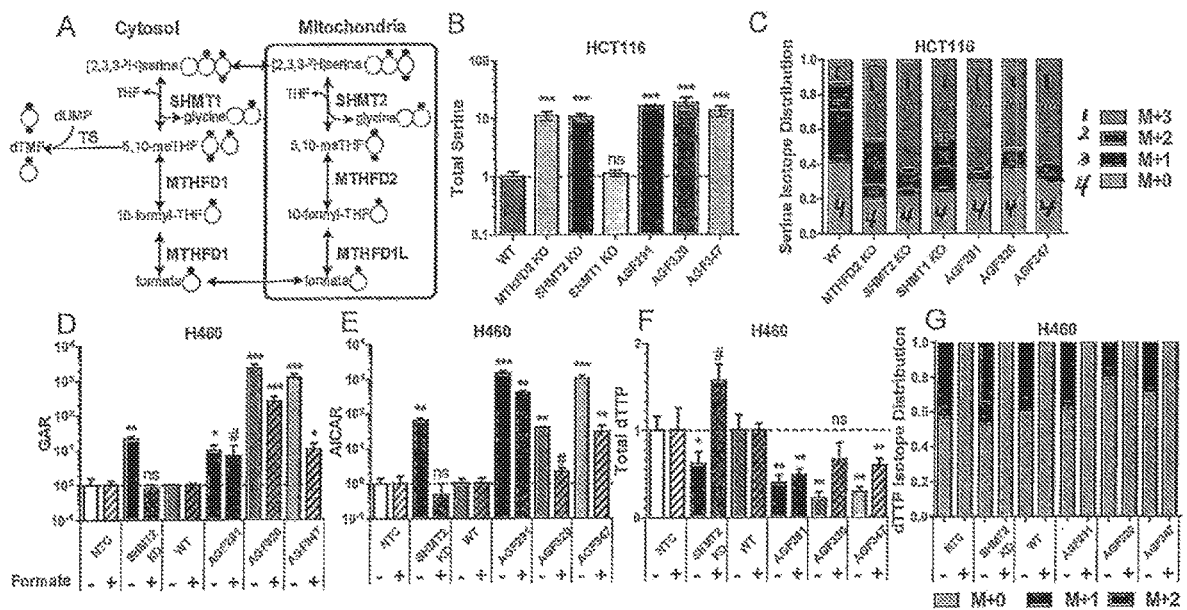
FIGS. 4A, 4B, 4C, 4D, 4E, 4F, and 4G show the targeted metabolomics analysis to identify intracellular enzyme targets of AGF291, AGF320, and AGF347.
Figure 5:
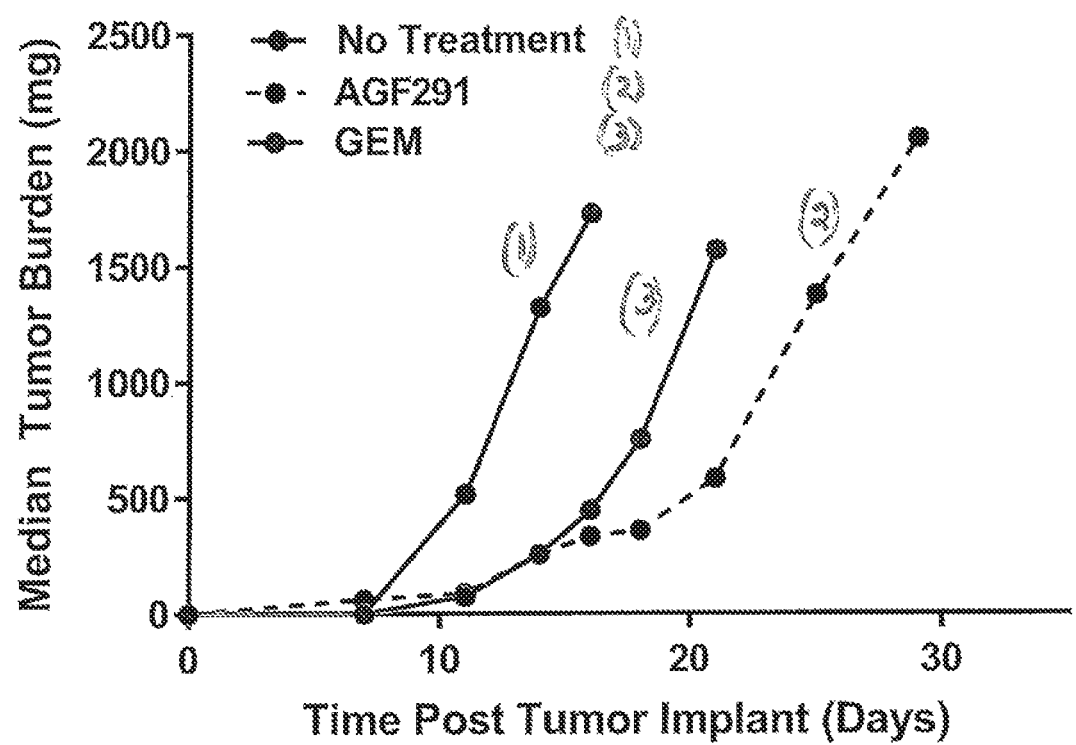
FIG. 5 shows in vivo efficacies of compound of this invention identified as AGF291 and GEM toward the MIA PaCa-2 PaC xenografts. Female ICR SCID mice (10 weeks old; 19 g average body weight) were implanted bilaterally with human MIA PaCa-2 PaC tumors. Beginning on day 3 following subcutaneous implantation, the mice were dosed as follows: AGF291, Q6d×3 at 7.75 mg/kg/inj, total dose 23.5 mg/kg; and GEM, Q4d×3 at 120 mg/kg/inj, total dose 480 mg/kg). T/C values were 19% for AGF291 and 26% for GEM.

Total serine pools were elevated ~10-fold in the HCT116 sublines with mitochondrial C1 KOs (SHMT2 KO and MTHFD2 KO) relative to WT controls (see FIG. 4B). KO of cytosolic SHMT1 (SHMT1 KO) had no impact on total serine pools. This establishes that SHMT2 rather than SHMT1 is the primary catabolic enzyme for serine in the tumor cells (20). In AGF291-, AGF320- and AGF347-treated HCT-116 cells, total serine also increased ~10-fold, indicating a profound loss of serine catabolism. Analogous results were seen with the H460 and MIA PaCa-2 cell lines, including the H460 SHMT2 KD cells (see FIGS. 15A and 15B).

The flux of [$^2$H]metabolites originating from [2,3,3-$^2$H] serine tracer is depicted in FIG. 4A. In tumor cells, C1 metabolism flows in a clockwise manner, with serine catabolized in mitochondria (starting with SHMT2) and regenerated in the cytosol (via SHMT1) (20). The reactions are reversible (e.g., serine can be resynthesized from formate in the mitochondria (20)). The compartmental metabolism of serine can be revealed by analyzing the isotope tracing ("scrambling") patterns from [2,3,3-$^2$H]serine in HCT116 cells (20, 21), including unmetabolized (i.e. M+3), and M+2 and M+1 serine resulting from 5,10-methylene-THF (M+2) and formate/10-formyl-THF (M+1), respectively (see FIG. 4A).

In WT HCT116 cells treated with [2,3,3-$^2$H]serine, most of the serine was catabolized (loss of M+3 serine was ~90%) (see FIG. 4C) and the label that remained was mostly incompletely labeled (scrambled) serine, reflecting resynthesized serine from labeled glycine (M+1 fraction; ~30% of total serine) (20). SHMT1 KO led to a drop (~60%) in the M+1 fraction without altering the M+2 serine fraction, consistent with SHMT1 in the cytosol being responsible for bulk synthesis of serine from glycine when SHMT2 is active (20). In SHMT2 KO cells, the M+3 fraction was >60% of the total serine (see FIG. 4C, consistent with a profound loss of serine catabolism. Reflecting this and the depletion of formate downstream of SHMT2, there was ~90% decreased M+1 serine (20). Further, the M+2 serine fraction also decreased (~25%) compared to WT cells, reflecting depleted 5,10-methylene-THF. Although similar results were seen for the M+1 and M+3 serine fractions with MTHFD2 KO cells (decreased ~75% and increased 3.5-fold, respectively, from WT levels), M+2 serine was increased (~1.7-fold) compared to that resulting from SHMT2 KO (see FIG. 4C). This reflects accumulation of 5,10-methylene-THF when MTHFD2 is lost (i.e., the M+2 serine isotopomer is generated through reversible activity of SHMT2 via proton abstraction). Thus, changes in serine isotope labeling from [2,3,3-$^2$H]serine are diagnostic for the specific perturbations in folate metabolism, and also inform upon the particular enzymatic step that is inhibited.

Treatment of WT HCT116 cells with compounds of the present invention, namely, AGF291, AGF320 or AGF347 closely recapitulated the effects of the SHMT2 KO, including a substantial M+3 serine fraction (~55-60% of total serine) and decreased M+2 serine (~2-3-fold) compared to WT cells, accompanied by nearly complete loss of M+1 serine (see FIG. 4E). Analogous results were obtained with SHMT2 KD and drug-treated WT H460 cells, and with MIA PaCa-2 cells treated with AGF291 (see FIG. 15C and FIG. 15D, respectively). Importantly, these results identify SHMT2 as the mitochondrial target for compounds of the present invention AGF291, AGF320 and AGF347.

Identification of cytosolic targets for compounds of the present invention AGF291, AGF320, and AGF347 by targeted metabolomics. Both GARFTase and AICARFTase require 10-formyl-THF derived from formate, most of which is generated via mitochondrial C1 metabolism from serine (20) (see FIGS. 1 and 4A). Consistent with this, loss of SHMT2 in H460 SHMT2 KD cells induced significant increases in purine intermediates which are dependent on C1 pools (i.e., 10-formyl-THF), including GAR (GARFTase substrate; 21-fold) (see FIG. 4D) and AICAR (AICARFTase substrate; 65-fold) (see FIG. 4E). Likewise, treatment with AGF291, AGF320, and AGF347 (10 μM) all increased GAR (10-2300-fold) and AICAR (40-1500-fold) relative to untreated controls (see FIGS. 4D and 4E). Similar increases in GAR and AICAR pools resulted in drug-treated HCT116 and MIA PaCa-2 cells (see FIGS. 15E, 15F, 15I, and 15J). For the HCT116 sublines, the increases in GAR and AICAR upon drug treatments generally exceeded those resulting from the SHMT2 KO.

To assess the possibility that the compounds of the present invention, namely, AGF291, AGF320 and AGF347 directly inhibit cytosolic enzyme targets in de novo purine biosynthesis (i.e., GARFTase and/or AICARFTase), we treated the H460 cells with 1 mM formate, to replenish the cytosolic C1 pool while circumventing the mitochondrial C1 pathway. We reasoned that formate treatment of the SHMT2 KD cell line should restore levels of GAR and AICAR to those seen in NTC (WT) cells. However, if the cytosolic enzymes were directly inhibited, formate should not effectively reverse accumulation of GAR and/or AICAR. Indeed, in H460 SHMT2 KD cells, treatment with formate completely reversed elevated GAR (see FIG. 4D) and AICAR (see FIG. 4E) accumulations to NTC levels. However, for drug-treated H460 cells, reversal by formate was incomplete, albeit to different extents for different compounds. With GAR, the extent of formate reversal was in the order, AGF291>AGF347>AGF320, whereas for AICAR, the rank order was AGF347>AGF320>AGF291. These results strongly implicate direct targeting of GARFTase and/or AICARFTase by these novel inhibitors in addition to SHMT2.

Targeted Metabolomics: Identification of SHMT1 as a target for pyrrolopyrimidine compounds of this invention. As SHMT2 (UniProtKB: P34897) maintains 66% sequence identity (36) to SHMT1 (UniProtKB: 34896), we considered the possibility that compounds of the present invention AGF291, AGF320 and AGF347 may also target SHMT1 in the cytosol, although this would be secondary to inhibition of SHMT2. By molecular modeling (see FIGS. 12F-12H), these compounds bound to rabbit SHMT1 (UniProtKB: 07511, 93% sequence homology with human SHMT1(37)) with docking scores from −8.9 to −11.14 kcal/mol (see Table S1).

To gauge potential SHMT1 inhibition by our compounds, we traced [2,3,3-$^2$H]serine into dTMP (dTTP), via C1 transfer from 5,10-methylene-THF to dUMP by TS (20) (see FIG. 4A). WT H460 cells incubated with [2,3,3-$^2$H]serine generated M+1 dTTP without M+2 dTTP (see FIG. 4G), confirming [2,3,3-$^2$H]serine metabolism through the mitochondrial C1 pathway to [$^2$H]formate into TTP (M+1) (20). Knockdown of SHMT2 (SHMT2 KD) induced a robust M+2 dTTP signal, reflecting the reverse-flux (serine glycine) through SHMT1 in the cytosol (20). In spite of compelling evidence for direct SHMT2 targeting (above), treatment with AGF291, AGF320, or AGF347 (10 µM) resulted in M+1 dTTP without M+2 dTTP (see FIG. 4G). This was accompanied by reduced (60-70%) dTTP pools (see FIG. 4F). Analogous results were obtained with both the HCT116 and MIA PaCa-2 sublines (see FIGS. 15G, 15H, 15K, and 15L). Treatment with 1 mM formate to elevate cytosolic C1 pools abolished $^2$H incorporation from [2,3,3-$^2$H]serine into dTTP (see FIG. 4G) for the drug-treated cells, this was accompanied by only partial restoration of dTTP (see FIG. 4F). For the SHMT2 KD cells, loss of SHMT2 resulted in suppressed dTTP (likely due to a decreased cytosolic C1 pool), and a dTTP "overshoot" when excess formate was provided.

As adenosine rather than thymidine (combined with glycine) was protective from growth inhibition by the compounds of the present invention, see FIGS. 3 and 14, the reduced dTTP pool (see FIG. 4F), combined with the absence of M+2 dTTP from [2,3,3-$^2$H]serine (see FIG. 4G), is most consistent with the direct targeting of SHMT1, in addition to SHMT2. Although our results are explained by targeting of both SHMT1 and SHMT2, the relative magnitudes of these inhibitions are difficult to assess by metabolomics assays alone.

Enzymology: To confirm the multiple enzyme targets (SHMT2, GARFTase, AICARFTase, and SHMT1) identified from our metabolomics experiments, we performed in vitro assays using purified recombinant enzymes. N-terminal His-tagged proteins were purified including GARFTase (formyltransferase domain; residues 100-302), ATIC (AICARFTase/IMP cyclohydrolase), SHMT2, SHMT1, and MTHFD2. GARFTase and AICARFTase assays were carried out as previously reported (38, 39) with slight modifications, whereas SHMT1/2 and MTHFD2 assays were developed for this study. For MTHFD2, using NADH as a readout, none of our lead molecules were inhibitory. For SHMT1 and SHMT2, a coupled enzyme assay with MTHFD2 was used. Our results demonstrate primary targeting of SHMT2 by "monoglutamyl" AGF291 and AGF320 ($K_i$s of 0.89 µM and 0.28 µM, respectively (Table 1). The relative $K_i$s for GARFTase and AICARFTase corroborate our metabolomics results (see FIGS. 4D and 4E), for which AGF320 was the most potent GARFTase inhibitor and AGF291 was the most potent AICARFTase inhibitor. These results confirm that SHMT2, and the purine biosynthetic enzymes GARFTase, and AICARFTase, are direct targets of our lead pyrrolo[3,2-d]pyrimidine compounds. As a control, AGF94 was tested and found to inhibit only GARFTase, with no inhibition for AICARFTase, SHMT2, or MTHFD2.

In vivo anti-tumor efficacy study with MIA PaCa-2 tumor xenografts. Based on in vitro efficacies with AGF291 toward various tumor cells (see FIG. 6), we performed an in vivo efficacy trial in comparison with the gemcitabine (GEM). Both AGF291 and GEM were efficacious, with median tumor burdens on day 14 of 256 mg (range 75-851 mg) and 255 mg (range 63-322 mg), respectively, compared to 1321 mg (range 685-1465 mg) for the control cohort. T/C values were 19% for AGF291 and 26% for GEM (see FIG. 5). Tumor growth delays (median T-C to reach 1000 mg) of 10.5 days for AGF291 and 7.5 days for GEM were recorded. AGF291 and GEM were well tolerated with modest weight losses (9% median nadir on day 17 and 12% median nadir on day 6, respectively) that were completely reversible after cessation of therapy. Thus, at equitoxic dose levels, AGF291 showed better anti-tumor efficacy than GEM, with a 20-fold decreased dose requirement and no acute or long-term toxicities other than reversible weight loss.

Table S2 shows in vivo efficacies of AGF291 and gemcitabine toward the MIA PaCa-2 xenografts. Female ICR SCID mice (10 weeks old; 19 g average body weight) were implanted bilaterally with human MIA PaCa-2 tumors. For the efficacy trial, the mice were maintained on either a folate-deficient diet from Harlan-Teklad (TD.00434) starting 14 days before subcutaneous tumor implant to ensure serum folate levels would approximate those of humans. Beginning on day 3 following subcutaneous implantation, the mice were dosed as follows: compound of this invention AGF291, every 6 days for three injections (Q6d×3) at 7.75 mg/kg/inj. (injection), total dose 23.5 mg/kg; and gemcitabine, every 4 days for three injections (Q4d×3) at 120 mg/kg/inj., total dose 480 mg/kg). The mice were weighed and tumors were measured with a caliper two-to-three times weekly; mice were sacrificed when the cumulative tumor burden reached 1500 mg. Tumor weights were estimated from two-dimensional measurements, where tumor mass (in mg)=$(a \times b^2)/2$, and a and b are the tumor length and width in mm, respectively. The tumor masses from both tumors on each mouse were added together, and the total mass per mouse was used for calculations of anti-tumor activity. Quantitative end-points include: (i) tumor growth delay [T-C, where T is the median time in days required for the treatment group tumors to reach a predetermined size (e.g., 1000 mg), and C is the median time in days for the control group tumors to reach the same size; tumor-free survivors are excluded from these calculations]; and (ii) T/C (in percent) when treatment (T) and control (C) groups for the control groups reached 700 mg in size (exponential growth phase). The median value of each group was determined (including zeros). Mouse weights were monitored as a gauge of drug toxicity.

Molecular Modeling and Computational Studies.

Molecular modeling was performed for all analogs with the human SHMT2 crystal structure (PDB: 5V7I) (47) using the induced fit docking protocol of Maestro (48, 49). The ligands were prepared using the Ligprep (50) application of Maestro. The docking protocol was validated by re-docking the co-crystallized pyranopyrazole ligand (47) into the crystal structure with a RMSD of 0.15 Å. The centroid around the pyranopyrazole inhibitor in Chain B was defined as the binding site for the compounds. The OPLS 2005 force field was used and amino acid residues within 3 Å from docked poses were allowed to be optimized using prime refinement (51). The compounds were also docked into rabbit SHMT1 (PDB: 1LS3) (52) binding sites. The docking scores of the analogs are reported in Table S1.

TABLE S2

Antitumor Efficacy Evaluation of AGF-291 and Gemcitabine Against Early Stage Human MIA PaCa-2 Pancreatic Adenocarcinoma xenografts in Female NCR SCID Mice

| Treatment | Drug Route | Schedule | Total Dosage mg/kg | Mean Body Weight Loss (g/mouse) | Percent Body Weight Loss | Median Tumor Burden in mg on d 16 (range) | T/C % | Tumor Free on d 52 | Time to 1000 mg in days (range) | Tumor Growth Delay (T − C) (days) |
|---|---|---|---|---|---|---|---|---|---|---|
| No treatment | — | — | — | −0.2 | −1.0 | 1726 (1213-2038) | — | 0/5 | 12.5 (12.5-15.0) | — |
| AGF291 | IV | Q6dx3 Start d3 | 23.5 | −1.8 | −8.9 | 334 (0-1221) | 19 | 0/5 | 23.0 (15.0-51) | 10.5 |
| Gemcitabine | IV | Q4dx4 Start d3 | 480 | −2.4 | −12.2 | 445 (150-527) | 26 | 0/5 | 20 (19-21) | 7.5 |

Most recently, we performed an in vivo study of MIA PaCa-2 xenografts with AGF347 (FIG. 6). In vivo efficacies of AGF347 and GEM toward the MIA PaCa-2 PaC xenografts. Female ICR SCID mice (10 weeks old; 19 g average body weight) were implanted bilaterally with human MIA PaCa-2 PaC tumors. Beginning on day 3 following subcutaneous implantation, the mice were dosed as follows: AGF347, Q2dx8 at 15 mg/kg/inj, total dose 120 mg/kg; and GEM, Q4dx4 at 120 mg/kg/inj, total dose 480 mg/kg). T/C values were 19% for AGF291 and 26% for GEM. For AGF347, the T-C (1000 mg) was 54 days and 1/5 mice was disease-free at 122 days.

Methods:

Chemicals.

[$^{14}$C]Formate (50-60 mCi/mmol) was purchased from Moravek Biochemicals (Brea, Calif.). [2,3,3-$^2$H, 98%]L-Serine was purchased from Cambridge Isotope Laboratories, Inc. (Andover, Mass.). Leucovorin [(6R,S) 5-formyl tetrahydrofolate (THF)] was provided by the Drug Development Branch, National Cancer Institute (Bethesda, Md.). Pemetrexed (Alimta) (PMX) was purchased from LC Laboratories (Woburn, Mass.). Lometrexol (5,10-dideaza-5,6,7,8-tetrahydrofolate) was obtained from Eli Lilly and Co. (Indianapolis, Ind.). Raltitrexed was obtained from AstraZeneca Pharmaceuticals (Maccesfield, Cheshire, England). Gemcitabine (Gemzar) was purchased from Pfizer (New York City, N.Y.). Serine-, glycine- and folate-free RPMI 1640 media was custom-ordered from ThermoFisher (Waltham, Mass.) and supplemented with tissue-culture grade glycine (ThermoFisher) or serine (Sigma-Aldrich), as needed. Other chemicals were obtained from commercial sources in the highest available purities.

Cell Culture and Proliferation/Protection Assays.

The HCT116 cell lines including the serine hydroxymethyltransferase (SHMT) 1, SHMT2, and methylene THF dehydrogenase 2 (MTHFD2) knockout (KO) cells were previously described (47,53). The H460 cell line was obtained from the American Type Culture Collection (Manassas, Va.), whereas the MIA PaCa-2 cells were provided by Dr. Yubin Ge (Karmanos Cancer Institute). Cell lines were verified by STR analysis by Genetica DNA Laboratories (Burlington, N.C.). MTXR1IOua$^R$2-4 (i.e. R2) Chinese hamster ovary (CHO) cells were generously provided by Dr. Wayne Flintoff (University of Western Ontario) (54). From this parental R2 cell line, human RFC and PCFT were individually transfected to generate the isogenic CHO cell lines designated PC43-10 (RFC) and R2/PCFT4 (PCFT) (55-57). Human tumor cell lines were cultured in folate-free RPMI supplemented with 10% dialyzed fetal bovine serum (Sigma-Aldrich), 1% penicillin/streptomycin solution, 2 mM L-glutamine, and 25 nM leucovorin in a humidified atmosphere at 37° C. in the presence of 5% $CO_2$ and 95% air. The CHO cell lines were cultured in alpha-minimal essential medium (alpha-MEM) supplemented with 10% bovine calf serum, 1% penicillin/streptomycin solution, and 2 mM L-glutamine. Additionally, the transfected CHO cell lines (i.e. R2/PCFT4 and PC43-10) were maintained under continuous selection with 1 mg/ml of G418.

For proliferation assays with the CHO cell lines, the cells were treated with drugs (0-1 µM) in a 96-well plate (2000 cells/well) in glycine-free, nucleoside free folate-free RPMI supplemented with 10% dialyzed fetal bovine serum, 1% penicillin/streptomycin, 2 mM L-glutamine, and 25 nM leucovorin (final volume 200 µL) over a 96 h incubation period at 37° C. with 5% $CO_2$. The drugs were dissolved in DMSO; an equivalent amount of DMSO was added to the control (no addition) samples. To quantify viable cells, the media was removed and plates were washed once with 100

μL Dulbecco's Phosphate-Buffered Saline (PBS), after which 100 μL PBS and 20 μL Cell Titer-blue (Promega) were added. Relative cell numbers were proportional to the fluorescence measured with a fluorescence plate reader (590 nm emission, 560 nm excitation). Background fluorescence (cell-free wells treated with Cell Titer-blue) was subtracted and these corrected values were normalized to results for cells treated in an identical manner without drugs. $IC_{50}$ values, corresponding to the drug concentrations that inhibit growth by 50% relative to untreated controls, were generated by fitting a 4-parameter logistic regression in Excel.

For proliferation assays of the HCT116, H460, and MIA PaCa2 tumor cell lines, the cells were plated in 96-well plates in an identical manner to the CHO experiments, except that the maximal drug concentration was increased to 10 μM. Glycine/nucleoside protection experiments in CHO and tumor cell lines were performed in folate- and glycine-free RPMI 1640/10% dialyzed fetal bovine serum supplemented with 25 nM leucovorin without additions, or in the presence of adenosine (60 μM), thymidine (10 glycine (130 μM) and/or 5-aminoimidazole-4-carboxamide (AICA) (320 μM). Growth of metabolite-treated cells was normalized to controls treated with metabolites and vehicle (i.e., DMSO) both singly and in combination. Treatments with all metabolites were performed in parallel on the same plate for a given drug.

Generation of H460 SHMT2 Knockdown (H460 SHMT2 KD) Cell Line.

H460 cells were seeded ($2\times10^5$ cells/well) in 24 well plates containing 1 ml of culture media (i.e. folate-free RPMI 1640 supplemented with 10% dialyzed fetal bovine serum, 1% penicillin/streptomycin, 2 mM L-glutamine, and 25 nM leucovorin). Cells were treated with 4 μg/ml polybrene and $10^5$ transducing units of MISSION Lentiviral particles (Sigma-Aldrich) containing shRNA targeting SHMT2 (TRCN0000034805). An additional well contained H460 cells without shRNA particles. After 24 hours, the media was replaced with fresh culture media including 2 μg/ml puromycin (58) as a selection marker. Once cells were confluent (and non-transduced cells had died), cells were harvested, passaged 3-4 times, then assayed by RT-PCR for SHMT2 knockdown (KD) relative to non-targeted control (NTC) particle-transduced H460 cells (58). To isolate single clones, cells were plated in 100 mm dishes (200 cells/dish) in the presence of 2 μg/ml puromycin. Colonies were isolated, and expanded and clonal cultures were assayed for SHMT2 KD via RT-PCR. SHMT2 KD was confirmed via Western blotting (FIG. 16).

Real-Time PCR.

Cells were harvested from either 60 mm dishes or T25 flasks at ~80% confluence and RNAs extracted using TRIzol reagent (Invitrogen, Carlsbad, Calif.). cDNAs were synthesized with random hexamers, MuLV reverse transcriptase, and RNase inhibitor (Applied Biosystems, Waltham, Mass.) and purified with a QIAquick PCR Purification Kit (QIAGEN, Valencia, Calif.). Quantitative real-time RT-PCR was performed using a Roche LightCycler 480 (Roche Diagnostics, Indianapolis, Ind.) with gene-specific primers and Universal Probe Library probes (SHMT2-#83, RFC-#32, PCFT-#89, FRα-#65 (Roche Diagnostics)) and transcript levels were normalized to transcript levels of β-actin and GAPDH. Primer sequences are available upon request.

Gel Electrophoresis and Western Blots.

H460 wild-type (WT), H460 NTC, H460 SHMT2 KD, HCT116 WT, and HCT116 SHMT2 KO cell lines were cultured, as described above. Cells were plated ($1\times10^6$ cells/dish) in 60 mm dishes and harvested when the cells were ~80% confluent. Cells were disrupted by sonication with cell debris removed by centrifugation (1800 rpm, 5 min, 4° C.). The soluble cell fraction was assayed for protein concentration (59) and equal amounts of protein (37 μg) from each sample were electrophoresed on 10% polyacrylamide gels with SDS (60) and transferred to polyvinylidene difluoride membranes (ThermoFisher) (61). To detect SHMT2, membranes were incubated for 72 h with rabbit anti-SHMT2 primary antibody (#12762 (53); Cell Signaling Technology, Danvers, Mass.). The blots were developed by incubating in IRDye800CW-conjugated goat anti-rabbit IgG secondary antibody (LICOR Biosciences, Omaha, Nebr.) for 90 min and scanning with an Odyssey infrared imaging system (LICOR Biosciences). Protein loading was normalized to β-actin using anti-β-actin mouse antibody (Sigma-Aldrich).

Targeted Metabolomics.

Targeted metabolomics were performed essentially as previously described (47, 53). Briefly, cells (H460, HCT116, MIA PaCa-2) (1 million cells/dish for vehicle-treated samples, 1.5 million cells/dish for drug-treated samples) were seeded in triplicate 60 mm dishes in 5 ml of folate-free RPMI (contains glycine and unlabeled serine) supplemented with 10% dialyzed fetal bovine serum, 1% penicillin/streptomycin, 2 mM L-glutamine, and 25 nM leucovorin. Cells were allowed to adhere for 24 h. The media was aspirated and replaced with culture media (contains 25 nM leucovorin, glycine, and unlabeled serine) and 10 μM AGF291, AGF320 or AGF347, or a comparable volume of vehicle (DMSO) (with or without 1 mM formate (final concentration)). After 16 h, the cells were washed with PBS (3x), the media was replaced with folate- and serine-free culture media (containing glycine) supplemented with 10% dialyzed fetal bovine serine, 25 nM leucovorin, and [2,3,3-$^2$H] serine (250 including 10 μM drug or DMSO vehicle. The cells were incubated for 24 h. All incubations were at 37° C. with 5% $CO_2$. The media was aspirated, and cells were washed (3x) rapidly (<30 s) with 5 mL ice-cold PBS; metabolism was quickly quenched with methanol:water (80:20) at −80° C. Cells were allowed to rock on dry ice for 10 min to cover the entire dish with 80:20 methanol:water (at −80° C.), then harvested by scraping and pipetting into 1.5 mL Eppendorf tubes. The tubes were centrifuged (4° C., 14000 RPM, 10 min) to fully extract metabolites into the methanol:water supernatant. The protein pellet was used for normalization. The supernatants were collected and analyzed by reversed-phase ion-pairing chromatography coupled with negative-mode electrospray-ionization high-resolution mass spectrometry on a stand-alone Orbitrap (ThermoFisher Exactive). Raw metabolite values were adjusted to correct for normal ion distributions and normalized to total proteins from the post-extraction pellet by solubilizing with 0.5 N NaOH and using the Folin-phenol protein method (13). Values below the limit of detection were assigned a value of 100 for normalization. Results for drug-treated and SHMT2 KD cells were normalized to vehicle-treated WT±formate or NTC±formate samples, as appropriate.

Enzymology:

In Vivo Efficacy Trial with MIA PaCa-2 Pancreatic Cancer Xenografts.

Methods for in vivo maintenance of MIA PaCa-2 tumor xenografts and drug efficacy evaluations are analogous to those previously described (58, 62-67). MIA PaCa-2 human pancreatic cancer cells ($5\times10^6$ cells/flank) were bilaterally implanted subcutaneously with tumor fragments (30-60 mg) with a 12-gauge trocar in female NCR SCID mice (NCI Animal Production Program). The mice were 10 weeks old on day 0 (tumor implant) with an average body weight of 19 g. For the efficacy trial, the mice were maintained on either a folate-deficient diet from Harlan-Teklad (TD.00434) starting 14 days before subcutaneous tumor implant to ensure serum folate levels would approximate those of humans. A separate cohort of mice was fed a folate-replete control diet from Lab Diet (5021). Mice were supplied with food and water ad libitum. Serum folate concentrations were monitored prior to tumor implant and post study by *Lactobacillus casei* bioassay (68). The mice in each group (folate-deficient and standard diet) were pooled before unselective distribution to the treatment and control groups. Chemotherapy was begun 3 days post-tumor implantation with AGF291 (7.75 mg/kg/injection every 6 days; total dose of 23.25 mg/kg) or gemcitabine (120 mg/kg/injection every 4 days; total dose of 480 mg/kg). The drugs were dissolved in 5% ethanol (v/v), 1% Tween-80 (v/v), and 0.5% $NaHCO_3$ and were administered intravenously (0.2 ml/injection). The mice were weighed and tumors were measured with a caliper two-to-three times weekly; mice were sacrificed when the cumulative tumor burden reached 1500 mg. Tumor weights were estimated from two-dimensional measurements, where tumor mass (in mg)=$(a \times b^2)/2$, and a and b are the tumor length and width in mm, respectively. The tumor masses from both tumors on each mouse were added together, and the total mass per mouse was used for calculations of anti-tumor activity. Quantitative end-points include: (i) tumor growth delay [T-C, where T is the median time in days required for the treatment group tumors to reach a predetermined size (e.g., 1000 mg), and C is the median time in days for the control group tumors to reach the same size; tumor-free survivors are excluded from these calculations]; and (ii) T/C (in percent) when treatment (T) and control (C) groups for the control groups reached 700 mg in size (exponential growth phase). The median value of each group was determined (including zeros). Mouse weights were monitored as a gauge of drug toxicity.

Statistics: All data shown reflects at least three biological replicates unless noted otherwise (e.g. targeted metabolomics data, which reflects three technical triplicates measured in single experiments). All statistical analyses were performed by the Karmanos Cancer Institute Biostatistics Core. The expression levels were assessed for the normality assumption. The $\log_2$ transformation was used as all values were positive. The statistical tests were carried out using an unpaired t-test. P values were not adjusted for multiple comparisons.

Synthesis of AGF94 and 5-substituted pyrrolo[3,2-d]pyrimidine Compounds

All evaporations were carried out in reduced pressure with a rotary evaporator. Analytical samples were dried in vacuo in a CHEM-DRY drying apparatus over $P_2O_5$ at 50° C. Melting points were determined either using a MEL-TEMP, II melting point apparatus with FLUKE 51 K/J electronic thermometer or using an MPA100 OptiMelt automated melting point system and are uncorrected. Nuclear magnetic resonance spectra for proton ($^1$H NMR) were recorded on the Bruker Avance II 400 (400 MHz) or Bruker Avance II 500 (500 MHz) NMR systems with TopSpin processing software. The chemical shift values (δ) are expressed in parts per million relative to tetramethylsilane as an internal standard. Thin-layer chromatography (TLC) was performed on Whatman® PE SIL G/UV254 flexible silica gel plates and the spots were visualized under 254 and 365 nm ultraviolet illumination. Proportions of solvents used for TLC are by volume. All analytical samples were homogeneous on TLC in at least two different solvent systems. Column chromatography was performed on the silica gel (70 to 230 meshes, Fisher Scientific) column. Flash chromatography was carried out on the CombiFlash® Rf systems, model COMBIFLASH RF. Pre-packed RediSep® Rf normal-phase flash columns (230 to 400 meshes) of diverse sizes were used. The amount (weight) of silica gel for column chromatography was in the range of 50-100 times the amount (weight) of the crude compounds being separated. Elemental analyses were performed by Atlantic Microlab, Inc., Norcross, Ga. Elemental compositions are within ±0.4% of the calculated values. Fractional moles of water or organic solvents frequently found in some analytical samples could not be prevented despite 24 to 48 h of drying in vacuo and were confirmed where possible by their presence in the $^1$H NMR spectra. The HPLC measurement was performed using UltiMate 3000 UHPLC+ system. Reverse phase HPLC was carried out with a XSelect CSH C18 XP, 130 Å, 2.5 μm, 3 mm×100 mm column. Solvent A: water with 0.1% TFA; Solvent B: acetonitrile. Mass spectrometry m/z determination was performed by an Advion Expression-S CMS (a single quadrupole compact MS) controlled by Advion Chems Express 4.0.13.8 software.

Figure 9:
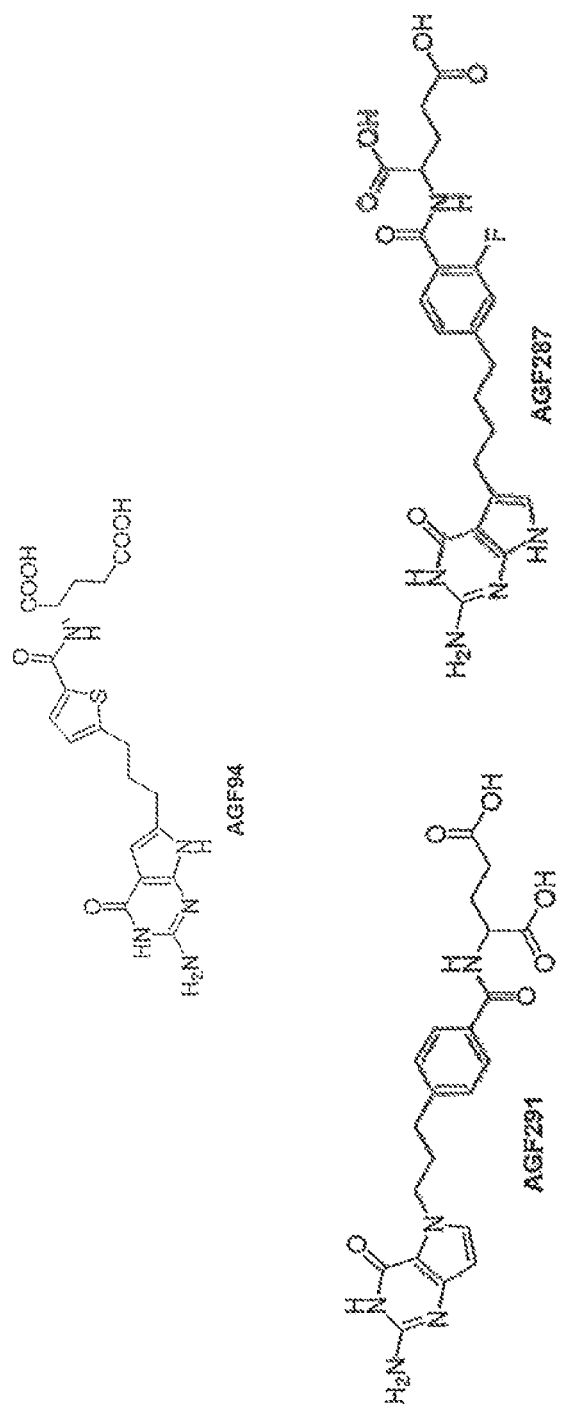
FIG. 9 shows the structures of the compounds of this invention namely AGF291 and AGF287, and reference compound AGF94.
Figures 10A, 10B, 10C, 10D, 10E:
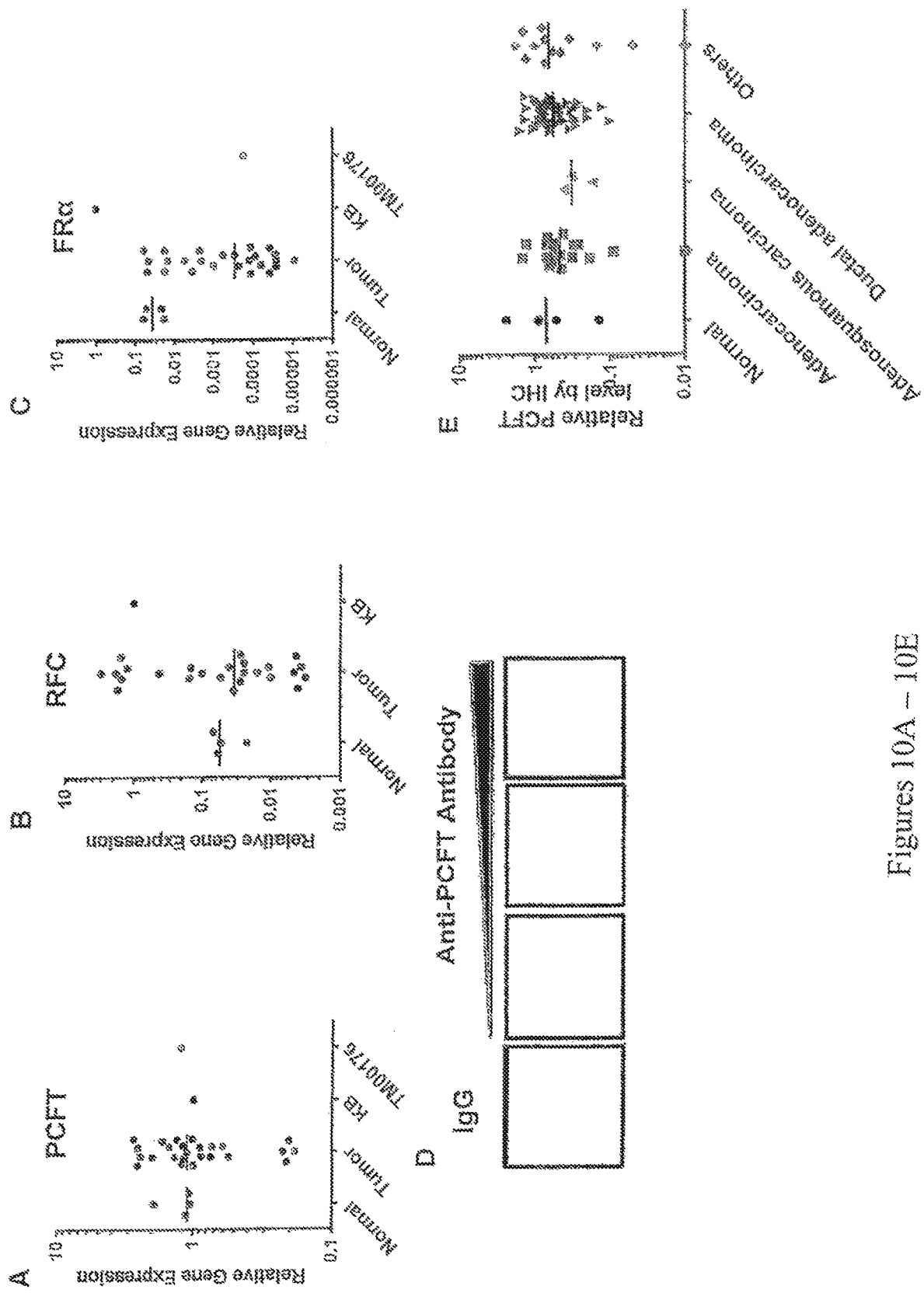
FIGS. 10A, 10B, 10C, 10D, and 10E show expression of PCFT in primary PaC specimens.
Figures 12A, 12B, 12C, 12D, 12E, 12F, 12G, 12H:
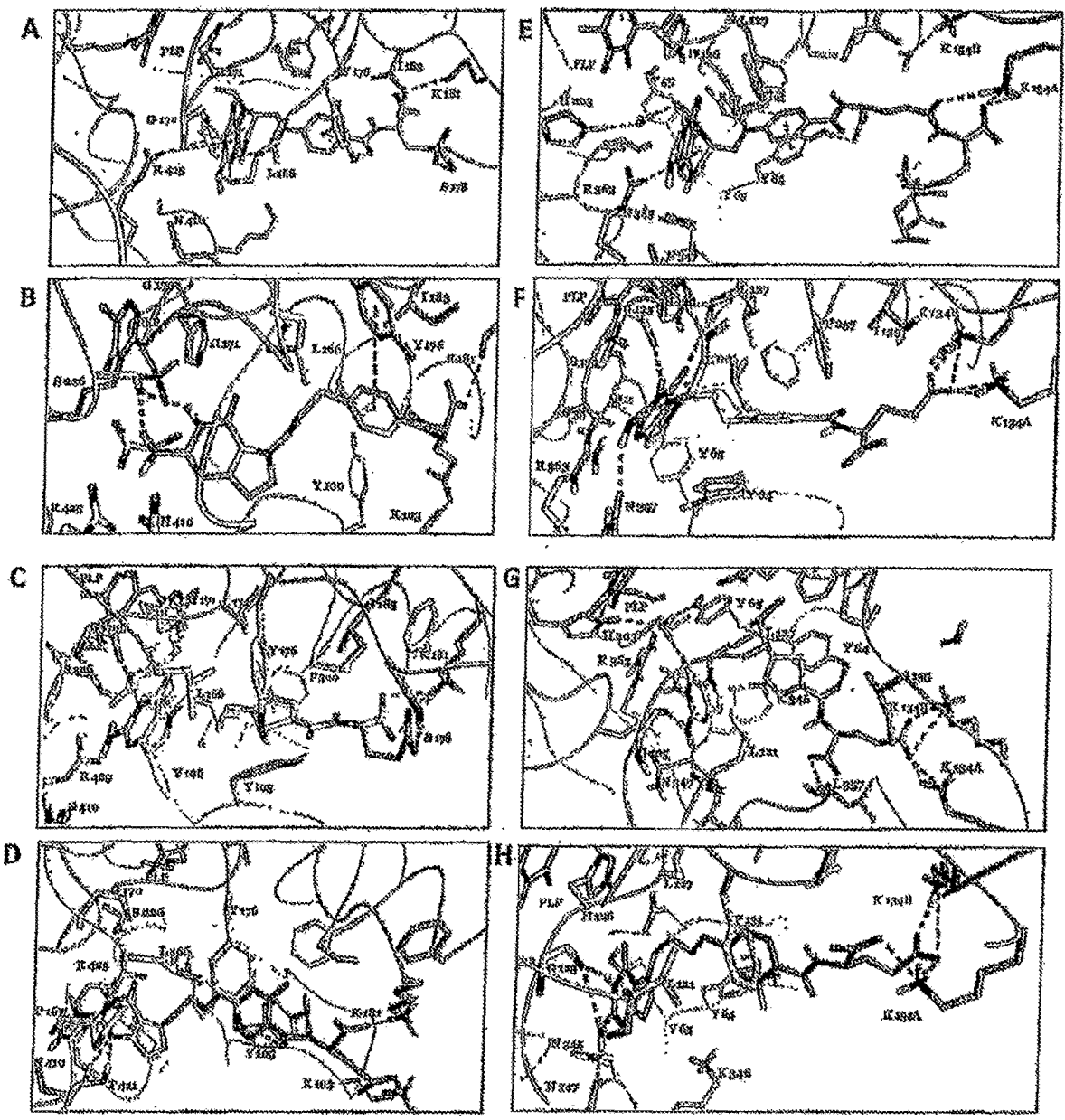
FIGS. 12A-12H show docked poses of 5-formyl-THF (A), AGF291 (B), AGF320 (C), and AGF347 (D) in the human dimeric SHMT2 crystal structure (PDB: 5V71) (42); crystal structure of 5-formyl THF triglutamate (E) in rabbit SHMT1 (PDB: 1L53) (43) and docked poses of AGF291 (F), AGF320 (G), and AGF347 (H) in the rabbit SHMT1 structure. Molecular modeling was performed using the induced fit docking protocol of Maestro (44, 45). The docking scores for all the proposed analogs in SHMT2 and SHMT1 are in Table 1S. Panels A-D: For AGF347 (panel D; best SHMT2 docking score of the series (Table 1S), the pyrrolo[3,2-d]pyrimidine scaffold occupies the pocket lined by Leu166, Asn410, Gly170, and Arg425. The 2-NH$_2$ group makes H-bond (faded plum color) with the backbone CO of Pro167 and N1 makes H-bond with Thr411 hydroxyl group and backbone NH. The four carbon alkyl chain linker substitution orients in the similar way as the linker at C6 position of 5-formylTHF in SHMT1 crystal structure (E).

AGF 94 (FIG. 9) was synthesized as previously described (66).

Synthesis of the target compounds AG291, AGF299, AGF300, AGF318, AGF320, AGF331, AGF347, AGF355 and AGF359 started with a palladium-catalyzed Sonogashira coupling of 4-iodobenzoate methyl ester (1a) or 4-bromo-thiophene-2-carboxylic acid ethyl ester (1b) or methyl 4-bromo-2-fluorobenzoate (1c) with the appropriate alkyne alcohols to afford the appropriate 4-substituted alcohol benzoates 2-i. Catalytic hydrogenation afforded the saturated alcohols 3a-i.(21) The alcohols 3a-i were converted to the mesylate derivatives using mesyl chloride and triethylamine base at 0° C.(69) The mesylate derivatives were not purified and after workup were converted to their respective iodide 4a-i using the Finkelstein reaction. The N-alkylation of iodides, 4a-i using ethyl 3-amino-1H-pyrrole-2-carboxylate and sodium hydride under anhydrous conditions afforded the N-5 substituted pyrroles 5a-i.(70) This reaction was incomplete as observed on TLC. Longer reaction times resulted in decomposition of the product (TLC). The intermediates 5a-i could not be isolated due to presence of multiple spots, even after repeated column chromatography. The crude N-substituted pyrroles 5a-i were directly subjected to condensation with 1,3-bis(methoxycarbonyl)-2-methylthiopseudourea with 5 equivalents of acetic acid as catalyst and MeOH. The hydrolysis of the carbamate group formed was carried out in situ with aqueous sodium hydroxide at 55° C. to afforded the 2-amino-4-oxo-pyrrolo[3,2-d]pyrimidines 6a-i.(24) This hydrolysis required higher than room temperature. Performing the hydrolysis at room temperature causes the hydrolysis of the ester, but not the carbamate (as observed on the $^1$H-NMR). However, temperatures greater than 70° C. caused degradation of the starting material. The optimum temperature for hydrolysis of both ester and carbamate was found to be 55° C. Conversion of free acids 6a-i to the corresponding L-glutamic acid diethyl esters 7a-i involved conventional peptide coupling with L-glutamic acid diethyl ester hydrochloride using 2-chloro-4,6-dimethoxy-1,3,5-triazine followed by chromatographic purification to afford the coupled products.(70)

Hydrolysis of 7a-i with aqueous NaOH at room temperature, followed by acidification with 1 N HCl in the cold, afforded target compounds.

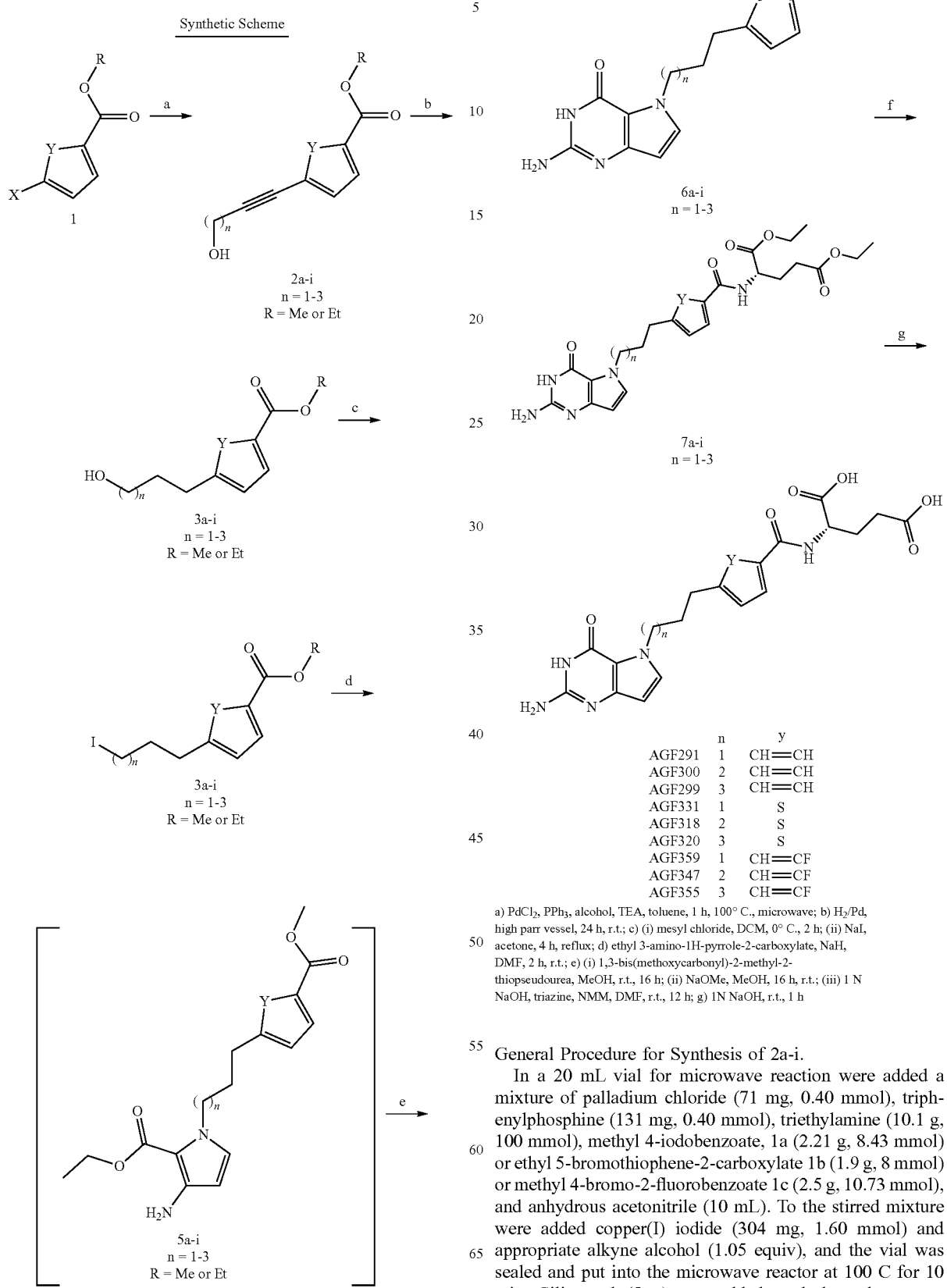

| | n | y |
|---|---|---|
| AGF291 | 1 | CH=CH |
| AGF300 | 2 | CH=CH |
| AGF299 | 3 | CH=CH |
| AGF331 | 1 | S |
| AGF318 | 2 | S |
| AGF320 | 3 | S |
| AGF359 | 1 | CH=CF |
| AGF347 | 2 | CH=CF |
| AGF355 | 3 | CH=CF | a) PdCl$_2$, PPh$_3$, alcohol, TEA, toluene, 1 h, 100° C., microwave; b) H$_2$/Pd, high parr vessel, 24 h, r.t.; c) (i) mesyl chloride, DCM, 0° C., 2 h; (ii) NaI, acetone, 4 h, reflux; d) ethyl 3-amino-1H-pyrrole-2-carboxylate, NaH, DMF, 2 h, r.t.; e) (i) 1,3-bis(methoxycarbonyl)-2-methyl-2-thiopseudourea, MeOH, r.t., 16 h; (ii) NaOMe, MeOH, 16 h, r.t.; (iii) 1 N NaOH, triazine, NMM, DMF, r.t., 12 h; g) 1N NaOH, r.t., 1 h General Procedure for Synthesis of 2a-i.

In a 20 mL vial for microwave reaction were added a mixture of palladium chloride (71 mg, 0.40 mmol), triphenylphosphine (131 mg, 0.40 mmol), triethylamine (10.1 g, 100 mmol), methyl 4-iodobenzoate, 1a (2.21 g, 8.43 mmol) or ethyl 5-bromothiophene-2-carboxylate 1b (1.9 g, 8 mmol) or methyl 4-bromo-2-fluorobenzoate 1c (2.5 g, 10.73 mmol), and anhydrous acetonitrile (10 mL). To the stirred mixture were added copper(I) iodide (304 mg, 1.60 mmol) and appropriate alkyne alcohol (1.05 equiv), and the vial was sealed and put into the microwave reactor at 100 C for 10 min. Silica gel (5 g) was added, and the solvent was evaporated under reduced pressure. The resulting plug was loaded on to a silica gel column (3.5 12 cm) and eluted with Hexane followed by 20% EtOAc in Hexane. The desired fraction (TLC) was collected, and the solvent was evaporated under reduced pressure to afford the target compounds.

Methyl 4-(3-hydroxyprop-1-yn-1-yl)benzoate (2a)

Compound 2a was synthesized using the general method described for the preparation of 2a-i using prop-2-yn-1-ol (0.5 ml, 8 mmol), to give 1.3 g of 2a as yellow solid (1.36 g, 85%); TLC Rf_0.16 (EtOAc:Hexane, 1:2); $^1$H-NMR (400 MHz) (Me$_2$SO-d$_6$) δ 8.06-7.87 (d, J=8.4 Hz, 2H, Ar), 7.55 (d, J=8.4 Hz, 2H, Ar), 4.30 (s, 1H, exch., —OH), 4.15 (s, 2H, —CH$_2$—), 3.81 (s, 3H, —OCH$_3$). The $^1$H-NMR matched the $^1$H-NMR reported in the literature (71).

Methyl 4-(4-hydroxybut-1-yn-1-yl)benzoate (2b)

Compound 2b was synthesized using the general method described for the preparation of 2a-i, using but-3-yn-1-ol (0.6 ml, 8 mmol), to give 1.2 g of 2b as yellow solid (1.53 g, 78%); TLC Rf=0.16 (EtOAc:Hexane, 1:2); mp, (72) 92.3-94.6° C.; $^1$H-NMR (400 MHz) (Me$_2$SO-d$_6$) δ 7.90 (d, J=8.7 Hz, 2H, Ar), 7.51 (d, J=8.7 Hz, 2H, Ar), 4.96 (s, 1H, exch., —OH), 3.84 (s, 3H, —OCH$_3$), 3.61 (m, 2H, —CH$_2$—), 2.60 (t, J=6.0 Hz, 2H, —CH$_2$—). The $^1$H-NMR matched the $^1$H-NMR reported in the literature (73).

Methyl 4-(5-hydroxypent-1-yn-1-yl)benzoate (2c)

Compound 2c was synthesized using the general method described for the preparation of 2a-i, using pent-4-yn-1-ol (0.67 ml, 8 mmol), to give 1.34 g of 2c as yellow semi-solid (1.62 g, 88%); TLC Rf 0.16 (EtOAc:Hexane, 1:2); $^1$H-NMR (400 MHz) (Me$_2$SO-d$_6$) δ 6.50 (d, J=8.4 Hz, 2H, Ar), 6.37 (d, J=8.4 Hz, 2H, Ar), 5.15 (s, 1H, exch., —OH), 3.61 (s, 3H, —OCH$_3$), 3.11 (t, J=4.9 Hz, 2H, —CH$_2$—), 2.64 (t, J=6.5 Hz, 2H, —CH$_2$—), 1.83-1.67 (m, 2H, —CH$_2$—). The $^1$H-NMR matched the $^1$H-NMR reported in the literature (74).

Ethyl 5-(3-hydroxyprop-1-yn-1-yl)thiophene-2-carboxylate (2d)

Compound 2d was synthesized using the general method described for the preparation of 2a-i, using prop-2-yn-1-ol (0.5 ml, 8 mmol), to give 1.2 g of 2d as yellow semi-solid (70%); TLC Rf=0.11 (EtOAc:Hexane, 1:2); $^1$H-NMR (400 MHz) (Me$_2$SO-d$_6$) δ 7.73 (d, J=4.0 Hz, 1H, Ar), 7.36 (d, J=3.9 Hz, 1H, Ar), 5.49 (t, J=6.0 Hz, 1H, —OH, exch.), 4.37-4.28 (m, 4H, —OCH$_2$ and —CH$_2$—), 1.29 (t, J=7.1 Hz, 3H, —CH$_3$). This compound was used for the next reaction without further characterization.

Ethyl 5-(4-hydroxybut-1-yn-1-yl)thiophene-2-carboxylate (2e)

Compound 388 was synthesized using the general method described for the preparation of 2a-i, using but-3-yn-1-ol (0.6 ml, 8 mmol), to give 1.1 g of 2e as yellow semi-solid (61%); TLC Rf=0.11 (EtOAc:Hexane, 1:2); $^1$H-NMR (400 MHz) (Me$_2$SO-d$_6$) δ 7.70 (d, J=4.0 Hz, 1H, Ar), 7.28 (d, J=4.0 Hz, 1H, Ar), 4.96 (t, J=5.6 Hz, 1H, OH, exch.), 3.91-3.81 (m, 2H, —OCH$_2$), 3.57 (t, J=6.4 Hz, 2H, —CH$_2$), 2.61 (t, J=6.4 Hz, 2H, —CH$_2$), 1.30 (t, J=7.1 Hz, 3H, —CH$_3$). The $^1$H-NMR matches the $^1$H-NMR reported previously (75).

Ethyl 5-(5-hydroxypent-1-yn-1-yl)thiophene-2-carboxylate (2f)

Compound 2f was synthesized using the general method described for the preparation 2a-i, using pent-4-yn-1-ol (0.67 ml, 8 mmol), to give 1.3 g of 2f as yellow semi-solid (68%); TLC Rf=0.11 (EtOAc:Hexane, 1:2); $^1$H-NMR (400 MHz) (Me$_2$SO-d$_6$) δ 7.63 (d, J=3.8 Hz, 1H, Ar), 6.95 (d, J=3.8 Hz, 1H, Ar), 4.44 (t, J=7.5 Hz, exch., —OH), 4.26 (q, J=7.0 Hz, 2H, —OCH$_2$), 2.83 (t, J=7.6 Hz, 2H, —CH$_2$—), 1.66 (p, J=6.5 Hz, 2H, —CH$_2$—), 1.46 (p, J=6.5 Hz, 2H, —CH$_2$—), 1.29-1.24 (m, 3H, —CH$_3$). This compound was used for the next reaction without further characterization.

Methyl 2-fluoro-4-(3-hydroxyprop-1-yn-1-yl)benzoate (2g)

Compound 2g was synthesized using the general method described for the preparation of 2a-i using prop-2-yn-1-ol (1.2 ml, 16.09 mmol), to give 2.02 g of 2g as yellow semi solid (2.02 g, 85%); TLC Rf=0.3 (EtOAc:Hexane, 1:1); $^1$H NMR (400 MHz, Me$_2$SO-d$_6$) δ 7.88 (t, J=7.9 Hz, 1H, Ar), 7.47-7.35 (m, 2H, Ar), 5.46 (s, 1H, exch., —OH), 4.34 (s, 2H, —CH$_2$—), 3.86 (s, 3H, —OCH$_3$). This compound was used for the next reaction without further characterization.

Methyl 2-fluoro-4-(4-hydroxybut-1-yn-1-yl)benzoate (2h)

Compound 2h was synthesized using the general method described for the preparation of 2a-i, using but-3-yn-1-ol (0.6 ml, 8 mmol), to give 1.86 g of 2h as yellow solid (1.86 g, 78%); TLC Rf=0.3 (EtOAc:Hexane, 1:1); mp, (26); $^1$H NMR (400 MHz, DMSO-d$_6$) δ 7.85 (t, J=8.0 Hz, 1H, Ar), 7.42-7.30 (m, 2H, Ar), 4.98 (t, J=5.6 Hz, 1H, exch., —OH), 3.85 (s, 3H, —OCH$_3$), 3.60 (td, J=6.7, 5.6 Hz, 2H, —CH$_2$—), 2.60 (t, J=6.7 Hz, 2H, —CH$_2$—). This compound was used for the next reaction without further characterization.

Methyl 2-fluoro-4-(5-hydroxypent-1-yn-1-yl)benzoate (2i)

Compound 2i was synthesized using the general method described for the preparation of 2a-i, using pent-4-yn-1-ol (1.5 ml, 16.01 mmol), to give 2.23 g of 2i as yellow semi solid (2.23 g, 88%); TLC Rf 0.3 (EtOAc:Hexane, 1:1), $^1$H-NMR (400 MHz) (Me$_2$SO-d$_6$) δ 7.85 (t, J=7.9 Hz, 1H, Ar), 7.38 (d, J=11.6 Hz, 1H, Ar), 7.33 (d, J=8.1 Hz, 1H, Ar), 6.67 (t, J=3.0 Hz, OH), 4.57 (t, J=10.4 Hz, 1H, exch., —OH), 3.85 (s, 3H, —OCH$_3$), 3.52 (q, J=5.8 Hz, 2H, —CH$_2$—), 1.69 (q, J=6.7 Hz, 2H, —CH$_2$—). This compound was used for the next reaction without further characterization.

General Procedure for Synthesis of 3a-i.

To a Parr flask was added 2a-i, 10% palladium on activated carbon (50% w/w), and MeOH (100 mL). Hydrogenation was carried out at 55 psi of H$_2$ for 4 h. The reaction mixture was filtered through Celite, washed with MeOH (100 mL), and concentrated under reduced pressure to give crude mixture containing 3a-i. Without chromatographic separation, these compounds were used for the next reaction.

Methyl 4-(3-hydroxypropyl)benzoate (3a)

Compound 371 was prepared using the general method described for the preparation of 3a-i, from 2a (1.45 g, 7.4 mmol) to give 1.2 g (98%) of 3a as a clear oil; TLC Rf=0.16 (EtOAc:Hexane, 1:2); $^1$H-NMR (400 MHz) (Me$_2$SO-d$_6$) 7.93 (d, J=8.0 Hz, 2H, Ar), 7.55 (d, J=7.9 Hz, 2H, Ar), 5.43 (s, 1H, exch., —OH), 3.85 (s, 3H, —OCH$_3$), 3.29 (t, J=7.8 Hz, 2H, —CH$_2$—), 2.67 (t, J=7.8 Hz, 2H, —CH$_2$—), 1.72 (dt, J=41.3, 7.4 Hz, 2H, —CH$_2$—). This compound was used for the next reaction without further characterization.

Methyl 4-(4-hydroxybutyl)benzoate (3b)

Compound 3b was prepared using the general method described for the preparation of 3a-i, from 3a (1.45 g, 7.4 mmol) to give 1.1 g (90%) of 3b as a clear oil; TLC Rf=0.16 (EtOAc:Hexane, 1:2); $^1$H-NMR (500 MHz) (Me$_2$SO-d$_6$) δ 7.88 (d, J=7.9 Hz, 2H, Ar), 7.34 (d, J=7.9 Hz, 2H, Ar), 4.43 (s, 1H, exch., —OH), 3.83 (s, 3H, —OCH$_3$), 3.35-3.25 (m, 2H, —CH$_2$—), 2.68 (q, J=10.4, 7.9 Hz, 2H, —CH$_2$—), 1.72 (dtd, J=49.7, 17.2, 15.4, 9.9 Hz, 4H, —CH$_2$—). This compound was used for the next reaction without further characterization.

Methyl 4-(5-hydroxypentyl)benzoate (3c)

Compound 3c was prepared using the general method described for the preparation of 3a-i, from 2c (1.45 g, 7.4 mmol) to give 1.2 g (98%) of 3c as a clear oil; TLC Rf=0.16 (EtOAc:Hexane, 1:2); $^1$H-NMR (400 MHz) (Me$_2$SO-d$_6$) 7.86 (d, J=7.9 Hz, 2H, Ar), 7.32 (d, J=7.9 Hz, 2H, Ar), 4.36 (s, 1H, exch., —OH), 3.82 (s, 3H, —OCH$_3$), 3.37 (t, J=6.4 Hz, 2H, —CH$_2$—), 2.62 (t, J=7.6 Hz, 2H, —CH$_2$—), 1.57 (p, J=7.7 Hz, 2H, —CH$_2$—), 1.43 (p, J=6.6 Hz, 2H, —CH$_2$—), 1.29 (ddt, J=8.6, 6.5, 3.9 Hz, 2H, —CH$_2$—). This compound was used for the next reaction without further characterization.

Ethyl 5-(3-hydroxypropyl)thiophene-2-carboxylate (3d)

Compound 3d was prepared using the general method described for the preparation of 3a-i, from 2d (1.1 g, 5.23 mmol) to give 1.0 g (89%) of 3d as a clear oil; TLC Rf 0.12 (EtOAc:Hexane, 1:2); $^1$H-NMR (400 MHz) (Me$_2$SO-d$_6$) δ 7.63 (t, J=6.1 Hz, 1H, Ar), 6.94 (d, J=6.1 Hz, 1H, Ar), 4.44 (t, J=5.1 Hz, 1H, exch., —OH), 4.26 (p, J=8.3, 7.1 Hz, 2H, —OCH$_2$—), 2.83 (t, J=7.6 Hz, 2H, —CH$_2$—), 1.66 (p, J=7.6 Hz, 2H, —CH$_2$—), 1.46 (p, J=6.8 Hz, 2H, —CH$_2$—), 1.27 (t, J=7.0 Hz, 3H, —CH$_3$). This compound was used for the next reaction without further characterization.

Ethyl 5-(4-hydroxybutyl)thiophene-2-carboxylate (3e)

Compound 3e was prepared using the general method described for the preparation of 3a-i, from 2e (1.2 g, 5.35 mmol) to give 1.0 g (82%) of 3e as a clear oil; TLC Rf=0.12 (EtOAc:Hexane, 1:2); $^1$H-NMR (400 MHz) (Me$_2$SO-d$_6$) δ 7.63 (d, J=3.7 Hz, 1H, Ar), 6.95 (d, J=3.8 Hz, 1H, Ar), 4.38 (s, 1H, exch., —OH), 4.23-4.20 (m, 2H, —OCH$_2$—), 2.84 (q, J=9.6, 7.5 Hz, 2H, —CH$_2$—), 1.63 (p, J=7.5 Hz, 3H, —CH$_3$), 1.56-1.39 (m, 2H, —CH$_2$—), 1.24-1.50 (m, 4H, —CH$_2$—). The $^1$H-NMR matches $^1$H-NMR of the reported compound (29).

Ethyl 5-(5-hydroxypentyl)thiophene-2-carboxylate (3f)

Compound 3f was prepared using the general method described for the preparation of 3a-i, from 2f (1.1 g, 4.62 mmol) to give 1.0 g (89%) of 3f as a clear oil; TLC Rf=0.12 (EtOAc:Hexane, 1:2); $^1$H-NMR (400 MHz) (Me$_2$SO-d$_6$) δ 7.63 (d, J=3.7 Hz, 1H, Ar), 6.95 (d, J=3.8 Hz, 1H, Ar), 4.36 (s, 1H, exch., —OH), 4.25 (q, J=7.0 Hz, 2H, —OCH$_2$—), 3.38 (t, J=6.3 Hz, 2H, —CH$_2$—), 2.83 (t, J=7.4 Hz, 2H, —CH$_2$—), 1.63 (p, J=7.5 Hz, 2H, —CH$_2$—), 1.44 (p, J=6.6 Hz, 2H, —CH$_2$—), 1.39-1.30 (m, 2H, —CH$_2$—), 1.28 (t, J=7.0 Hz, 3H, —CH$_3$). This compound was used for the next reaction without further characterization.

Methyl 2-fluoro-4-(3-hydroxypropyl)benzoate (3g)

Compound 3g was prepared using the general method described for the preparation of 3a-i, from 2g (2.02 g, 9.7 mmol) to give 1.98 g (98%) of 3g as a clear oil; TLC Rf=0.3 (EtOAc:Hexane, 1:1); $^1$H-NMR (400 MHz) (Me$_2$SO-d$_6$) δ 7.81 (t, J=7.8 Hz, 1H, Ar), 7.24-7.14 (m, 2H, Ar), 4.55 (s, 1H, exch., —OH), 3.84 (s, 3H, —OCH$_3$), 3.41 (d, J=6.3 Hz, 2H, —CH$_2$—), 2.73-2.64 (m, 2H, —CH$_2$—), 1.78-1.68 (m, 2H, —CH$_2$—). This compound was used for the next reaction without further characterization.

Methyl 2-fluoro-4-(4-hydroxybutyl)benzoate (3h)

Compound 3h was prepared using the general method described for the preparation of 3a-i, from 3h (1.86 g, 8.4 mmol) to give 1.68 g (90%) of 3b as a clear oil; TLC Rf=0.3 (EtOAc:Hexane, 1:1); $^1$H-NMR (500 MHz) (Me$_2$SO-d$_6$) δ 7.80 (t, J=7.9 Hz, 1H, Ar), 7.22-7.14 (m, 2H, Ar), 4.39 (s, 1H, exch., —OH), 3.84 (s, 3H, —OCH$_3$), 3.40 (d, J=11.7 Hz, 2H, —CH$_2$—), 2.65 (t, J=7.7 Hz, 2H, —CH$_2$—), 1.66-1.55 (m, 2H, —CH$_2$—), 1.42 (dt, J=13.4, 6.5 Hz, 2H, —CH$_2$—). This compound was used for the next reaction without further characterization.

Methyl 2-fluoro-4-(5-hydroxypentyl)benzoate (3i)

Compound 3i was prepared using the general method described for the preparation of 3a-i, from 2i (2.23 g, 9.44 mmol) to give 2.23 g (98%) of 3c as a clear oil; TLC Rf=0.3 (EtOAc:Hexane, 1:1); $^1$H-NMR (400 MHz) (Me$_2$SO-d$_6$) 1H NMR (400 MHz, DMSO-d6) δ 7.80 (t, J=7.9 Hz, 1H, Ar), 7.24-7.13 (m, 2H, Ar), 4.37 (s, 1H, exch., —OH), 3.84 (s, 3H, —OCH$_3$), 3.37 (t, J=6.4 Hz, 2H, —CH$_2$—), 2.69-2.60 (m, 2H, —CH$_2$—), 1.58 (p, J=7.6 Hz, 2H, —CH$_2$—), 1.44 (dd, J=14.2, 7.4 Hz, 2H, —CH$_2$—), 1.35-1.23 (m, 2H, —CH$_2$—). This compound was used for the next reaction without further characterization.

General Procedure for Synthesis of 4a-i.

To the alcohols 3a-i, was added triethylamine (1 equivalent) and dichloromethane (25 mL). The reaction was cooled to 0° C. and purged with nitrogen gas. Under anhydrous conditions, methanesulfonyl chloride (1.05 equivalent) was added dropwise over 30 minutes. The reaction was stirred at room temperature for 2 hours and the reaction was added into sodium bicarbonate solution (25 mL). The water layer was washed thrice with dichloromethane (100 mL). The dichloromethane was evaporated to obtain a semi-solid product. To the intermediate in acetone, sodium iodide (1 equivalent) was added and refluxed for 8 hours. The reaction mixture was filtered. The filtrate was evaporated to obtain 4a-i.

Methyl 4-(3-iodopropyl)benzoate (4a)

Compound 4a was prepared using the general method described for the preparation of 4a-i, from 3a (1 g, 4.5 mmol), methanesulfonyl chloride (0.35 mL, 4.5 mmol) and triethylamine (0.62 mL, 4.5 mmol) to form the intermediate. To this sodium iodide was added and the procedure was followed to give 0.9 g (72%) of 4a as a clear oil; TLC Rf=0.63 (EtOAc:Hexane, 1:2); $^1$H-NMR (400 MHz) (Me$_2$SO-d$_6$) δ 7.95-7.83 (d, J=8.0 Hz, 2H, Ar), 7.36 (d, J=8.0 Hz, 2H, Ar), 3.84 (s, 3H, —OCH$_3$), 3.24 (t, J=6.8 Hz, 2H, —CH$_2$—), 2.74 (t, J=7.5 Hz, 2H, —CH$_2$—), 2.07 (p, J=7.0 Hz, 2H, —CH$_2$—).

This compound was used for the next reaction without further characterization.

Methyl 4-(4-iodobutyl)benzoate (4b)

Compound 4b was prepared using the general method described for the preparation of 4a-i, from 3b (1 g, 4.5 mmol), methanesulfonyl chloride (0.35 mL, 4.5 mmol) and triethylamine (0.62 mL, 4.5 mmol) to form the intermediate. To this sodium iodide was added and the procedure was followed to give 1.0 g (80%) of 4b as a clear oil; TLC Rf=0.63 (EtOAc:Hexane, 1:2); $^1$H-NMR (500 MHz) (Me$_2$SO-d$_6$) δ 7.86 (d, J=8.2 Hz, 2H, Ar), 7.31 (d, J=8.3 Hz, 2H, Ar), 4.55 (t, J=5.1 Hz, 2H, —CH$_2$—), 3.82 (s, 3H, —OCH$_3$), 3.41 (t, J=6.4 Hz, 2H, —CH$_2$—), 2.65 (t, J=6.4 Hz, 2H, —CH$_2$—), 1.78-1.66 (m, 2H, —CH$_2$—), 1.47-1.40 (m, 2H, —CH$_2$). This compound was used for the next reaction without further characterization.

Methyl 4-(5-iodopentyl)benzoate (4c)

Compound 4c was prepared using the general method described for the preparation of 4a-i, from 3c (1 g, 4.5 mmol), methanesulfonyl chloride (0.35 mL, 4.5 mmol) and triethylamine (0.62 mL, 4.5 mmol) to form the intermediate. To this sodium iodide was added and the procedure was followed to give 1.05 g (85%) as 4c clear oil; TLC Rf=0.63 (EtOAc:Hexane, 1:2); $^1$H-NMR (400 MHz) (Me$_2$SO-d$_6$) δ 7.87 (d, J=8.2 Hz, 2H, Ar), 7.31 (d, J=8.3 Hz, 2H, Ar), 3.82 (s, 3H, —OCH$_3$), 3.23 (t, J=6.9 Hz, 2H, —CH$_2$—), 2.62 (t, J=7.7 Hz, 2H, —CH$_2$—), 1.76 (p, J=7.0 Hz, 2H, —CH$_2$—), 1.57 (tt, J=9.2, 6.9 Hz, 2H, —CH$_2$—), 1.40-1.29 (m, 2H, —CH$_2$—). This compound was used for the next reaction without further characterization.

Ethyl 5-(3-iodopropyl)thiophene-2-carboxylate (4d)

Compound 4d was prepared using the general method described for the preparation of 4a-i, from 3d (0.9 g, 4.5 mmol), methanesulfonyl chloride (0.35 mL, 4.5 mmol) and triethylamine (0.62 mL, 4.5 mmol) to form the intermediate. To this sodium iodide was added and the procedure was followed to give 0.85 g (61%) of 4d as a clear oil; TLC Rf=0.63 (EtOAc:Hexane, 1:2); $^1$H-NMR (400 MHz) (Me$_2$SO-d$_6$) δ 7.63 (t, J=4.6 Hz, 1H, Ar), 6.97 (d, J=3.7 Hz, 1H, Ar), 4.25 (q, J=7.1 Hz, 2H, —CH$_2$—), 3.26 (t, J=6.8 Hz, 2H, —CH$_2$—), 2.93 (q, J=9.0, 7.4 Hz, 2H, —CH$_2$—), 2.10 (p, J=6.9 Hz, 2H, —CH$_2$—), 1.28 (t, J=7.1 Hz, 3H, —CH$_3$). This compound was used for the next reaction without further characterization.

Ethyl 5-(4-iodobutyl)thiophene-2-carboxylate (4e)

Compound 4e was prepared using the general method described for the preparation of 4a-i, from 3e (0.95 g, 4.5 mmol), methanesulfonyl chloride (0.35 mL, 4.5 mmol) and triethylamine (0.62 mL, 4.5 mmol) to form the intermediate. To this sodium iodide was added and the procedure was followed to give 0.9 g (63%) of 4e as a clear oil; TLC Rf=0.63 (EtOAc:Hexane, 1:2); $^1$H-NMR (400 MHz) (Me$_2$SO-d$_6$) δ 7.64 (d, J=3.8 Hz, 1H, Ar), 6.97 (d, J=3.8 Hz, 1H, Ar), 4.26 (q, J=7.1 Hz, 2H, —CH$_2$—), 3.46-3.24 (m, 2H, —CH$_2$—), 2.87 (t, J=7.3 Hz, 2H, —CH$_2$—), 1.93-1.64 (m, 4H, —CH$_2$—), 1.28 (t, J=7.1 Hz, 3H, —OCH$_3$). This compound was used for the next reaction without further characterization.

Ethyl 5-(5-iodopentyl)thiophene-2-carboxylate (4f)

Compound 395 was prepared using the general method described for the preparation of 4a-i, from 3f (1 g, 4.38 mmol), methanesulfonyl chloride (0.35 mL, 4.5 mmol) and triethylamine (0.62 mL, 4.5 mmol) to form the intermediate. To this sodium iodide was added and the procedure was followed to give 0.95 g (64%) of 4f as a clear oil; TLC Rf=0.63 (EtOAc:Hexane, 1:2); $^1$H-NMR (400 MHz) (Me$_2$SO-d$_6$) δ 7.60 (t, J=4.6 Hz, 1H, Ar), 7.21 (d, J=3.7 Hz, 1H, Ar), 4.22 (q, J=7.1 Hz, 2H, —CH$_2$—), 3.35-3.27 (m, 2H, —CH$_2$—), 3.12 (tt, J=9.3, 5.2 Hz, 2H, —CH$_2$—), 2.57 (t, J=6.8 Hz, 2H, —CH$_2$—), 1.97 (q, J=7.1 Hz, 2H, —CH$_2$—), 1.29-1.12 (m, 5H, —CH$_2$— and —CH$_3$). This compound was used for the next reaction without further characterization.

Methyl 2-fluoro-4-(3-iodopropyl)benzoate (4g)

Compound 4g was prepared using the general method described for the preparation of 4a-i, from 3g (1.98 g, 9.33 mmol), methanesulfonyl chloride (0.96 mL, 12.4 mmol) and triethylamine (2 mL, 14 mmol) to form the intermediate. To this sodium iodide was added and the procedure was followed to give 2.17 g (72%) of 4a as a clear oil; TLC Rf=0.8 (EtOAc:Hexane, 1:1); $^1$H-NMR (400 MHz) (Me$_2$SO-d$_6$) δ 7.82 (t, J=7.9 Hz, 1H. Ar), 7.28-7.16 (m, 2H, Ar), 3.84 (s, 3H, —OCH$_3$), 3.24 (t, J=6.9 Hz, 2H, —CH$_2$—), 2.79-2.70 (m, 2H, —CH$_2$—), 2.13-2.04 (m, 2H, —CH$_2$—). This compound was used for the next reaction without further characterization.

Methyl 2-fluoro-4-(4-iodobutyl)benzoate (4h)

Compound 4h was prepared using the general method described for the preparation of 4a-i, from 3h (1.7 g, 7.51 mmol), methanesulfonyl chloride (0.77 mL, 9.99 mmol) and triethylamine (1.6 mL, 11.27 mmol) to form the intermediate. To this sodium iodide was added and the procedure was followed to give 2.02 g (80%) of 4b as a clear oil; TLC Rf=0.8 (EtOAc:Hexane, 1:1); $^1$H-NMR (500 MHz) (Me$_2$SO-d$_6$) δ 7.86-7.77 (m, 1H, Ar), 7.25-7.13 (m, 2H, Ar), 3.84 (s, 3H, Ar), 3.32-3.25 (m, 2H, —CH$_2$—), 2.67 (t, J=7.4 Hz, 2H, —CH$_2$—), 1.82-1.72 (m, 2H, —CH$_2$—), 1.70-1.6 (m, 2H, —CH$_2$—). This compound was used for the next reaction without further characterization.

Methyl 2-fluoro-4-(5-iodopentyl)benzoate (4i)

Compound 4i was prepared using the general method described for the preparation of 4a-i, from 3i (2.23 g, 9.28 mmol), methanesulfonyl chloride (0.96 mL, 12.34 mmol) and triethylamine (1.9 mL, 13.92 mmol) to form the intermediate. To this sodium iodide was added and the procedure was followed to give 2.75 g (85%) as 4c clear oil; TLC Rf=0.8 (EtOAc:Hexane, 1:1); $^1$H-NMR (400 MHz) (Me$_2$SO-d$_6$) δ 7.81 (t, J=7.9 Hz, 1H, Ar), 7.30-7.18 (m, 2H, Ar), 3.84 (s, 3H, —OCH$_3$), 3.28 (t, J=6.9 Hz, 2H, —CH$_2$—), 2.66 (t, J=7.6 Hz, 2H, —CH$_2$—), 1.83-1.73 (m, 2H, —CH$_2$—), 1.67-1.58 (m, 2H, —CH$_2$—), 1.37 (q, J=7.8 Hz, 2H, —CH$_2$—). This compound was used for the next reaction without further characterization.

General Procedure for Synthesis of 6a-i.

To a solution of ethyl 3-amino-1H-pyrrole-2-carboxylate hydrochloride (0.5 g, 3.24 mmol) in dry DMF (10 mL) was added slowly NaH (0.17 g, 7.1 mmol) under nitrogen at room temperature. The resulting mixture was stirred for about 15 min when there was no more gas produced, and then appropriate iodide (1 equivalent) was added. The reaction mixture was stirred at room temperature for 4 h, and DMF was evaporated at elevated temperature to offer a gummy residue, which was used for the next step without purification. The gummy residue was dissolved in MeOH (10 mL), and 1,3-bis(methoxycarbonyl)-2-methyl-2-thiopseudourea (0.7 g, 3.3 mmol) was added followed by AcOH (1.0 g, 15 mmol). The mixture was stirred at room temperature overnight and became a thick paste. NaOMe in MeOH (25%) (7 mL, 22 mmol) was added, and stirring was continued at room temperature overnight. The mixture was neutralized with AcOH, and the methanol was removed under reduced pressure. To the residue was added water (20 mL), and the pH value was adjusted to 10-11 by adding NH$_3$.H$_2$O. The solid was collected by filtration and washed well with water. The resulting solid was added to 1 N NaOH (2 mL), and the mixture was heated at 55° C. for 3 h. The mixture was cooled and acidified using 1 N hydrochloric acid. The precipitate was collected and dried under reduced pressure overnight to obtain 6a-i.

General Procedure for Synthesis of 7a-i.

To a solution of 6a-i in anhydrous DMF (10 mL) was added N-methylmorpholine (73 mg, 0.72 mmol) and 2-chloro-4,6-dimethoxy-1,3,5-triazine (127 mg, 0.72 mmol). The resulting mixture was stirred at room temperature for 2 h. To this mixture was added N-methylmorpholine (73 mg, 0.72 mmol) and L-glutamate diethyl ester hydrochloride (144 mg, 0.6 mmol). The reaction mixture was stirred for an additional 4 h at room temperature. Silica gel (400 mg) was then added, and the solvent was evaporated under reduced pressure. The resulting plug was loaded on to a silica gel column with 5% MeOH in CHCl$_3$ as the eluent. Fractions that showed the desired spot (TLC) were pooled and the solvent evaporated to dryness to afford compounds 7a-i.

General Method for Synthesis of Target Compounds.

To a solution of 7a-i, was added 4 mL methanol and 2 mL of 1 N sodium hydroxide solution. The reaction mixture was stirred for 1 hour at room temperature and the disappearance of the starting material was spotted with TLC. The mixture was acidified to pH 2-3 using 1 N hydrochloric acid to obtain target compounds as precipitate on filtration.

Diethyl (4-(3-(2-amino-4-oxo-3,4-dihydro-5H-pyrrolo[3,2-d]pyrimidin-5-yl)propyl) benzoyl-L-glutamate (7a)

Using the general method for synthesis of compounds 6a-i, 5a (1.1 g, 3.62 mmol) was used to obtain 6a (0.3 g, 30%) as a white solid. Using the general method for synthesis of compounds 7a-i, 6a (0.15 g, 0.48 mmol) was used to obtain 7a (0.18 g, 75%) as a greyish brown solid; TLC Rf=0.23 (MeOH:CHCl$_3$:NH$_4$OH, 1:10:0.5); $^1$H-NMR (400 MHz) (Me$_2$SO-d$_6$) δ 10.49 (s, 1H, exch., —NH), 8.67 (d, J=7.4 Hz, 1H, exch., —NH), 7.80 (d, J=8.0 Hz, 2H, Ar), 7.29 (d, J=8.0 Hz, 2H, Ar), 7.21 (d, J=2.6 Hz, 1H, Ar), 5.91 (d, J=2.7 Hz, 1H, Ar), 5.81 (s, 2H, exch., 2-NH$_2$), 4.42 (d, J=7.4 Hz, 1H, —CH), 4.30-4.20 (m, 2H, —CH$_2$—), 4.17-3.94 (m, 4H, —CH$_2$—), 2.65-2.54 (m, 2H, —CH$_2$—), 2.44 (t, J=7.4 Hz, 2H, —CH$_2$—), 2.22-1.86 (m, 4H, —CH$_2$—), 1.35-1.09 (m, 6H, —CH$_3$). Anal. Calcd. C$_{25}$H$_{31}$N$_5$O$_6$: C, 60.35; H, 6.28; N, 14.08; 0, 19.29. Found: C, 60.03; H, 6.17; N, 13.76.

Diethyl (4-(4-(2-amino-4-oxo-3,4-dihydro-5H-pyrrolo[3,2-d]pyrimidin-5-yl)butyl) benzoyl)-L-glutamate (7b)

Using the general method for synthesis of compounds 6a-i, 5b (1.1 g, 3.46 mmol) was used to obtain 6b (0.25 g, 25%) as a white solid; TLC Rf=0.0 (MeOH:CHCl$_3$:HCl, 1:5:0.5); $^1$H-NMR (400 MHz) (Me$_2$SO-d$_6$) δ 10.50 (s, br, exch., —COOH), 7.81 (d, J=7.9 Hz, 2H, Ar), 7.21 (d, J=8.0 Hz, 2H, Ar), 7.18 (d, J=2.9 Hz, 1H, Ar), 5.92 (s, 2H, exch., 2-NH$_2$), 5.87 (d, J=2.7 Hz, 1H, Ar), 4.25 (t, J=6.8 Hz, 2H, —CH$_2$—), 2.61 (t, J=7.7 Hz, 2H, —CH$_2$—), 1.73 (p, J=7.8 Hz, 2H, —CH$_2$—), 1.48 (p, J=7.8 Hz, 2H, —CH$_2$—). The melting point assessment suggested impurities and hence this compound was used for the next reaction without further characterization. Using the general method for synthesis of compounds 7a-i, 6b (0.15 g, 0.46 mmol) was used to obtain 7b (0.1 g, 43%) as a brown solid; TLC Rf=0.23 (MeOH:CHCl$_3$:NH$_4$OH, 1:10:0.5); $^1$H-NMR (400 MHz) (Me$_2$SO-d$_6$) δ 10.44 (s, 1H, exch., —NH), 8.64 (d, J=7.4 Hz, 1H, exch., —NH), 7.77 (d, J=8.2 Hz, 2H, Ar), 7.26 (d, J=8.2 Hz, 2H, Ar), 7.19 (d, J=2.9 Hz, 1H, Ar), 5.88 (s, J=2.9 Hz, 1H, Ar), 5.76 (s, 2H, exch., 2-NH$_2$), 4.45-4.41 (m, 1H, —CH), 4.25 (t, J=6.8 Hz, 2H, —CH$_2$—), 4.18-4.00 (m, 4H, —CH$_2$—), 2.62 (t, J=7.6 Hz, 2H, —CH$_2$—), 2.44 (t, J=7.5 Hz, 2H, —CH$_2$—), 2.28-1.89 (m, 2H, —CH$_2$—), 1.87-1.62 (m, 2H, —CH$_2$—), 1.60-1.40 (m, 2H, —CH$_2$—), 1.18 (dt, J=9.9, 7.0 Hz, 6H, —CH$_3$). Anal. Calcd. C$_{26}$H$_{33}$N$_5$O$_6$ 0.05 CHCl$_3$: C, 61.04; H, 6.50; N, 13.69; 0, 18.76. Found: C, 60.57; H, 6.44; N, 13.28.

Diethyl (4-(5-(2-amino-4-oxo-3,4-dihydro-5H-pyrrolo[3,2-d]pyrimidin-5-yl)pentyl) benzoyl)-L-glutamate (7c)

Using the general method for synthesis of compounds 6a-i, 5c (1.2 g, 3.61 mmol) was used to obtain 6c (0.32 g, 29%) as a white solid; TLC Rf=0.0 (MeOH:CHCl$_3$:HCl, 1:5:0.5); $^1$H-NMR (400 MHz) (Me$_2$SO-d$_6$) δ 12.74 (s, 1H, exch., —COOH), 8.14 (s, 2H, exch., 2-NH$_2$), 7.83 (d, J=7.9 Hz, 2H, Ar), 7.45 (d, J=2.9 Hz, 1H, Ar), 7.28 (d, J=8.0 Hz, 2H, Ar), 6.13 (d, J=2.9 Hz, 1H, Ar), 4.29 (t, J=6.9 Hz, 2H, —CH$_2$—), 3.37 (t, J=6.4 Hz, 2H, —CH$_2$—), 2.64 (t, J=7.8 Hz, 2H, —CH$_2$—), 1.79-1.70 (m, 2H, —CH$_2$—), 1.54-1.45 (m, 2H, —CH$_2$—). The melting point assessment suggested impurities and hence this compound was used for the next reaction without further characterization. Using the general method for synthesis of compounds 7a-i, 6c (0.15 g, 0.44 mmol) was used to obtain 7c (0.11 g, 47.50%) as a grey solid TLC Rf=0.23 (MeOH:CHCl$_3$:NH$_4$OH, 1:10:0.5); $^1$H-NMR (400 MHz) (Me$_2$SO-d$_6$) δ 10.45 (s, 1H, exch., —NH), 8.66 (d, J=7.6 Hz, 1H, exch., —NH), 7.77 (d, J=8.0 Hz, 2H, Ar), 7.27 (d, J=8.0 Hz, 2H, Ar), 7.16 (d, J=2.7 Hz, 1H, Ar), 5.87 (d, J=2.8 Hz, 1H, —Ar), 5.75 (s, 2H, exch., —NH$_2$), 4.41 (d, J=13.0 Hz, 1H, —CH), 4.19 (t, J=6.9 Hz, 2H, —CH$_2$—), 4.14-3.96 (m, 4H, —CH$_2$—), 2.59 (t, J=7.6 Hz, 2H, —CH$_2$—), 2.43 (t, J=7.4 Hz, 2H, —CH$_2$—), 2.20-1.92 (m, 2H, —CH$_2$—), 1.81-1.65 (m, 2H, —CH$_2$—), 1.63-1.51 (m, 2H, —CH$_2$—), 1.22-1.11 (m, 8H, —CH$_2$— and —CH$_3$). Anal. Calcd. for C$_{27}$H$_{35}$N$_5$O$_6$ 0.24 H$_2$O: C, 61.70; H, 6.71; N, 13.32. Found: C, 61.20; H, 6.763; N, 13.13.

Diethyl (5-(3-(2-amino-4-oxo-3,4-dihydro-5H-pyrrolo[3,2-d]pyrimidin-5-yl)propyl) thiophene-2-carbonyl)-L-glutamate (7d)

Using the general method for synthesis of compounds 6a-i, 5d (1.0 g, 2.97 mmol) was used to obtain 6d (0.18 g, 19%) as a white solid; TLC Rf=0.0 (MeOH:CHCl$_3$:HCl, 1:5:0.5); $^1$H-NMR (400 MHz) (Me$_2$SO-d$_6$) δ 11.22 (s, br, 1H, exch., —COOH), 7.49 (d, J=3.6 Hz, 1H, Ar), 7.19 (d, J=3.0 Hz, 1H, Ar), 6.87 (d, J=3.8 Hz, 1H, Ar), 6.00 (s, 2H, exch., 2-NH$_2$), 5.94 (d, J=3.0 Hz, 1H, Ar), 4.25 (t, J=6.8 Hz, 2H, —CH$_2$—), 2.70 (t, J=7.8 Hz, 2H, —CH$_2$—), 2.06 (t, J=7.6 Hz, 2H, —CH$_2$—). The melting point assessment suggested impurities and hence this compound was used for the next reaction without further characterization. Using the general method for synthesis of compounds 7a-i, 6d (0.15 g, 0.47 mmol) was used to obtain 7d (0.125 g, 53%) as a grey semi-solid; TLC Rf=0.23 (MeOH:CHCl$_3$:NH$_4$OH, 1:10: 0.5); $^1$H-NMR (400 MHz) (Me$_2$SO-d$_6$) δ 10.44 (s, 1H, exch., —NH), 8.62 (d, J=7.5 Hz, 1H, exch., —NH), 7.69 (d, J=3.8 Hz, 1H, Ar), 7.20 (d, J=2.9 Hz, 1H, Ar), 6.91 (d, J=3.8 Hz, 1H, Ar), 5.91 (d, J=2.9 Hz, 1H, Ar), 5.77 (s, 2H, exch., 2-NH$_2$), 4.38 (dt, J=9.4, 5.9 Hz, 1H, —CH), 4.27 (t, J=6.8 Hz, 2H, —CH$_2$—), 4.08 (dq, J=23.8, 7.0 Hz, 4H, —CH$_2$—), 2.72 (t, J=7.9 Hz, 2H, —CH$_2$—), 2.42 (t, J=7.5 Hz, 2H, —CH$_2$—),), 2.10 (q, J=7.2 Hz, 2H, —CH$_2$—), 1.97 (ddd, J=16.7, 14.0, 7.6 Hz, 2H, —CH$_2$—), 1.18 (dt, J=9.0, 7.1 Hz, 6H, —CH$_3$). This compound was used for the next reaction without further characterization.

Diethyl (5-(4-(2-amino-4-oxo-3,4-dihydro-5H-pyrrolo[3,2-d]pyrimidin-5-yl)butyl) thiophene-2-carbonyl)-L-glutamate (7e)

Using the general method for synthesis of compounds 6a-i, 5e (1.0 g, 2.97 mmol) was used to obtain 6e (0.20 g, 20%) as a white solid. Using the general method for synthesis of compounds 7a-i, 6e (0.18 g, 0.54 mmol) was used to obtain 7e (0.1 g, 37%) as a brown semi-solid; TLC Rf=0.23 (MeOH:CHCl$_3$:NH$_4$OH, 1:10:0.5); $^1$H-NMR (400 MHz) (Me$_2$SO-d$_6$) δ 10.45 (s, 1H, exch., —NH), 8.63 (d, J=7.7 Hz, 1H, exch., —NH), 7.67 (d, J=3.8 Hz, 1H, Ar), 7.20 (d, J=2.5 Hz, 1H, Ar), 6.85 (d, J=3.9 Hz, 1H, Ar), 5.88 (d, J=2.9 Hz, 1H, Ar), 5.76 (s, 2H, exch., 2-NH$_2$), 4.3-4.45 (m, 1H, —CH), 4.26 (t, J=6.8 Hz, 2H, —CH$_2$—), 4.07 (dq, J=22.7, 7.2 Hz, 4H, —CH$_2$—), 3.46-3.24 (m, 2H, —CH$_2$—), 2.79 (t, J=7.4 Hz, 2H, —CH$_2$—), 2.42 (t, J=7.4 Hz, 2H, —CH$_2$—), 1.76 (t, J=7.6 Hz, 2H, —CH$_2$—), 1.51 (t, J=7.6 Hz, 2 H, —CH$_2$—), 1.17 (dt, J=9.5, 7.1 Hz, 6H, —CH$_3$). This compound was used for the next reaction without further characterization.

Diethyl (5-(5-(2-amino-4-oxo-3,4-dihydro-5H-pyrrolo[3,2-d]pyrimidin-5-yl)pentyl) thiophene-2-carbonyl)-L-glutamate (7f)

Using the general method for synthesis of compounds 6a-i, 5f (2.0 g, 5.74 mmol) was used to obtain 6f (0.34 g, 30%) as a white solid. Using the general method for synthesis of compounds 7a-i, 6f (0.34 g, 1.03 mmol) was used to obtain 7f (0.11 g, 72%) as a grey semi-solid; TLC Rf=0.23 (MeOH:CHCl$_3$:NH$_4$OH, 1:10:0.5); $^1$H-NMR (400 MHz) (Me$_2$SO-d$_6$) δ 10.69 (s, 1H, exch., —NH—), 8.65 (d, J=7.5 Hz, 1H, exch., —NH), 7.69 (d, J=3.8 Hz, 1H, Ar), 7.16 (d, J=2.9 Hz, 1H, Ar), 6.85 (d, J=3.7 Hz, 1H, Ar), 6.12-5.71 (m, 3H, Ar (1H) and 2-NH$_2$ (2H, exch.)), 4.41 (d, J=5.6 Hz, 1H, —CH), 4.21 (t, J=6.8 Hz, 2H, —CH$_2$—), 4.11 (q, J=7.1 Hz, 2H, —CH$_2$—), 4.04 (q, J=7.1 Hz, 2H, —CH$_2$—), 2.75 (t, J=7.4 Hz, 2H, —CH$_2$—), 2.42 (d, J=7.5 Hz, 2H, —CH$_2$—), 2.21-1.89 (m, 2H, —CH$_2$—), 1.73 (t, J=7.4 Hz, 2H, —CH$_2$—), 1.60 (t, J=7.6 Hz, 2H, —CH$_2$—), 1.16 (m, 8H, —CH$_2$— and —CH$_3$). This compound was used for the next reaction without further characterization.

Diethyl (4-(3-(2-amino-4-oxo-3,4-dihydro-5H-pyrrolo[3,2-d]pyrimidin-5-yl)propyl)-2-fluorobenzoyl)-L-glutamate (7g)

Using the general method for synthesis of compounds 6a-i, 5g (1.1 g, 3.62 mmol) was used to obtain 6g (0.3 g, 30%) as a white solid; TLC Rf=0.0 (MeOH:CHCl$_3$:HCl, 1:5:0.5); mp, 121.8-156.3° C.; $^1$H-NMR (500 MHz) (Me$_2$SO-d$_6$) δ 7.77 (t, J=7.9 Hz, 1H, Ar), 7.24 (d, J=2.9 Hz, 1H, Ar), 7.16-7.10 (m, 2H, Ar), 6.09 (s, 2H, exch., 2-NH$_2$), 5.94 (d, J=2.8 Hz, 1H, Ar), 4.26 (t, J=7.0 Hz, 2H, —CH$_2$—), 2.59 (dd, J=8.9, 6.8 Hz, 2H, —CH$_2$—), 2.09-2.02 (m, 2H, —CH$_2$—). Using the general method for synthesis of compounds 7a-i, 6g (0.15 g, 0.48 mmol) was used to obtain 7g (0.2 g, 75%) as a brown solid; TLC Rf=0.3 (MeOH:CHCl$_3$: NH$_4$OH, 1:10:0.5); $^1$H-NMR (500 MHz) (Me$_2$SO-d$_6$) δ 11.06 (s, 1H, exch., —NH), 8.58 (dd, J=7.6, 2.0 Hz, 1H, Ar), 7.51 (t, J=7.8 Hz, 1H, Ar), 7.21 (d, J=2.9 Hz, 1H, Ar), 7.18-7.08 (m, 2H, Ar), 5.91 (d, J=2.8 Hz, 1H, Ar), 5.80 (s, 2H, exch., 2-NH$_2$), 4.45-4.37 (m, 1H, —CH), 4.25 (t, J=7.0 Hz, 2H, —CH$_2$—), 4.12 (qq, J=7.0, 3.7 Hz, 2H, —CH$_2$—), 4.05 (q, J=7.1 Hz, 2H, Ar), 3.86 (s, 2H, Ar), 2.58 (dt, J=15.2, 8.0 Hz, 2H), 2.46-2.40 (m, 2H), 2.07-1.95 (m, 4H, —CH$_2$—), 1.19 (dt, J=14.0, 7.1 Hz, 6H, —CH$_3$).

Diethyl (4-(4-(2-amino-4-oxo-3,4-dihydro-5H-pyrrolo[3,2-d]pyrimidin-5-yl)butyl)-2-fluorobenzoyl)-L-glutamate (7h)

Using the general method for synthesis of compounds 6a-i, 5h (1.1 g, 3.46 mmol) was used to obtain 6h (0.25 g, 25%) as a white solid; TLC Rf=0.0 (MeOH:CHCl$_3$:HCl, 1:5:0.5); $^1$H-NMR (400 MHz) (Me$_2$SO-d$_6$) δ 7.76 (t, J=8.1 Hz, 1H, Ar), 7.23 (d, J=2.9 Hz, 1H, Ar), 7.16-7.05 (m, 2H, Ar), 6.03 (s, 2H, exch., 2-NH$_2$), 5.91 (d, J=2.8 Hz, 1H, Ar), 4.25 (t, J=6.8 Hz, 2H, —CH$_2$—), 2.62 (t, J=7.7 Hz, 2H, —CH$_2$—), 1.72 (p, J=6.9 Hz, 2H, —CH$_2$—), 1.48 (qd, J=9.3, 8.8, 6.3 Hz, 2H, —CH$_2$—). The compound was used for the next reaction without further characterization. Using the general method for synthesis of compounds 7a-i, 6h (0.15 g, 0.46 mmol) was used to obtain 7h (0.1 g, 43%) as a brown solid; TLC Rf=0.23 (MeOH:CHCl$_3$:NH$_4$OH, 1:10: 0.5); $^1$H-NMR (400 MHz) (Me$_2$SO-d$_6$)$^1$H NMR (400 MHz, DMSO-d$_6$) δ 7.88 (s, 1H, exch., —NH), 7.55-7.45 (m, 2H, Ar), 7.17-7.06 (m, 2H, Ar), 6.15 (d, J=2.8 Hz, 1H, Ar), 4.42 (s, 1H, —CH), 4.29 (t, J=6.8 Hz, 2H, —CH$_2$—), 4.17-4.01 (m, 4H, —CH$_2$—), 4.05-3.93 (m, 2H, —CH$_2$—), 3.66 (t, J=12.4 Hz, 2H, —CH₂—), 2.64 (t, J=7.6 Hz, 2H, —CH₂—), 1.74 (m, 2H, —CH₂—), 1.51 (d, J=6.8 Hz, 2H, —CH₂—), 1.26-1.13 (m, 6H, —CH₃).

Diethyl (4-(5-(2-amino-4-oxo-3,4-dihydro-5H-pyrrolo[3,2-d]pyrimidin-5-yl)pentyl)-2-fluorobenzoyl)-L-glutamate (7i)

Using the general method for synthesis of compounds 6a-i, 5i (1.2 g, 3.61 mmol) was used to obtain 6i (0.32 g, 29%) as a white solid; TLC Rf=0.0 (MeOH:CHCl₃:HCl, 1:5:0.5); ¹H-NMR (400 MHz) (Me₂SO-d₆) δ 7.70 (td, J=8.2, 6.3 Hz, 1H, Ar), 7.16 (d, J=2.8 Hz, 1H, Ar), 7.10-7.00 (m, 2H, Ar), 5.94 (s, 2H, exch., —NH₂), 5.86 (d, J=2.8 Hz, 1H, Ar), 4.23-4.14 (m, 2H, —CH₂—), 2.60 (dt, J=21.4, 7.8 Hz, 2H, —CH₂—), 1.75-1.50 (m, 4H, —CH₂—), 1.25-1.15 (m, 2H). The melting point assessment suggested impurities and hence this compound was used for the next reaction without further characterization. Using the general method for synthesis of compounds 7a-i, 6i (0.15 g, 0.44 mmol) was used to obtain 7i (0.11 g, 47.50%) as a grey solid TLC Rf=0.23 (MeOH:CHCl₃:NH₄OH, 1:10:0.5); ¹H-NMR (400 MHz) (Me₂SO-d₆) δ 11.17 (s, 1H, exch., —NH), 8.57 (dd, J=7.5, 2.0 Hz, 1H, exch., —NH), 7.50 (t, J=7.8 Hz, 1H, Ar), 7.38 (d, J=2.9 Hz, 1H, Ar), 7.16-7.07 (m, 2H, Ar), 6.07 (d, J=2.8 Hz, 1H, Ar), 4.43 (ddd, J=9.5, 7.4, 5.1 Hz, 1H, —CH), 4.24 (t, J=7.1 Hz, 2H, —CH₂—), 4.12 (qq, J=7.0, 3.7 Hz, 2H, —CH₂—), 4.08-4.03 (m, 2H, —CH₂—), 2.61 (t, J=7.7 Hz, 2H, —CH₂—), 2.46-2.40 (m, 2H, —CH₂—), 2.09 (m, 2H, —CH₂—), 1.75 (p, J=7.3 Hz, 2H), 1.57 (q, J=7.6 Hz, 2H), 1.22-1.17 (m, 8H, —CH₂— and —CH₃).

(4-(3-(2-amino-4-oxo-3,4-dihydro-5H-pyrrolo[3,2-d]pyrimidin-5-yl)propyl)benzoyl)-L-glutamic acid (AGF291)

Using the general method for synthesis of target compounds, 7a (0.10 g, 0.2 mmol) was used to obtain AGF291 (0.06 g, 67%) as a white solid; TLC Rf=0.0 (MeOH:CHCl₃:HCl, 1:5:0.5); mp, 71.8-80.0° C.; ¹H-NMR (400 MHz) (Me₂SO-d₆) δ 12.10-11.20 (s, br, 3H, exch., —COOH and —NH), 8.59-8.25 (m, 1H, exch., —NH), 7.75 (d, J=7.9 Hz, 2H, Ar), 7.27 (d, J=7.7 Hz, 2H, Ar), 7.19 (d, J=2.6 Hz, 1H, Ar), 6.44 (s, 2H, exch., 2-NH₂), 5.89 (d, J=2.7 Hz, 1H, Ar), 4.32-4.19 (m, 3H, —CH and —CH₂), 2.57 (t, J=7.3 Hz, 2H, 2.34-2.11 (m, 2H, —CH₂—), 2.11-1.98 (m, 2H, —CH₂—), 2.01-1.83 (m, 2H, —CH₂—). Anal. Calcd. for C₂₁H₂₃N₅O₆ 0.9 CH₃OH 0.8 HCl: C, 52.67; H, 5.53; N, 14.02. Found: C, 52.53; H, 5.63; N, 14.07.

(4-(4-(2-amino-4-oxo-3,4-dihydro-5H-pyrrolo[3,2-d]pyrimidin-5-yl)butyl)benzoyl)-L-glutamic acid (AGF300)

Using the general method for synthesis of target compounds, 7b (0.10 g, 0.195 mmol) was used to obtain AGF300 (0.056 g, 63%) as a white solid; TLC Rf=0.0 (MeOH:CHC13:HCl, 1:5:0.5); mp, 82.3-87.0° C.; 1H-NMR (400 MHz) (Me₂SO-d6) δ 11.80-11.00 (s, br, exch., 3H, COOH and NH), 8.26 (s, 1H, exch., —NH), 7.71 (d, J=7.9 Hz, 2H, Ar), 7.33-7.09 (m, 3H, Ar), 6.14 (s, 2H, exch., 2-NH₂), 5.86 (d, J=2.2 Hz, 1H, Ar), 4.23 (m, 3H, —CH— and —CH₂—), 2.77-2.56 (m, 2H, —CH₂—), 2.37-2.09 (m, 2H, —CH₂—), 2.04-1.84 (m, 2H, —CH₂—), 1.71 (m, 2H, —CH₂—), 1.46 (d, J=7.4 Hz, 2H, —CH₂). Anal. Calcd. for C₂₂H₂₅N₅O₆ 0.77 HCl: C, 54.64; H, 5.37; N, 14.48. Found: C, 54.71; H, 5.34; N, 14.28.

(4-(5-(2-amino-4-oxo-3,4-dihydro-5H-pyrrolo[3,2-d]pyrimidin-5-yl)pentyl)benzoyl)-L-glutamic acid (AGF299)

Using the general method for synthesis of target compounds, 7c (0.10 g, 0.195 mmol) was used to obtain AGF299 (0.050 g, 56%) as a white solid; TLC Rf=0.0 (MeOH:CHCl₃:HCl, 1:5:0.5); mp, 82.3-84.8° C.; ¹H-NMR (400 MHz) (Me₂SO-d₆) δ 11.95 (s, 2H, exch., —COOH), 8.54 (d, J=7.7 Hz, exch., —NH), 7.79 (d, J=7.8 Hz, 2H, Ar), 7.40-7.00 (m, 3H, Ar), 6.37 (s, 2H, exch., 2-NH₂), 5.94 (d, J=2.9 Hz, 1H, Ar), 4.38 (d, J=8.2 Hz, 1H, —CH—), 4.21 (t, J=7.0 Hz, 2H, —CH₂—), 2.60 (t, J=7.7 Hz, 2H, —CH₂—), 2.36 (t, J=7.4 Hz, 2H, —CH₂—), 2.17-1.82 (m, 2H, 1.80-1.65 (m, 2H, 1.60-1.45 (m, 2H, —CH₂—), 1.26-1.00 (m, 2H, —CH₂—). Anal. Calcd. C₂₃H₂₇N₅O₆ 1.08 H₂O: C, 56.50; H, 6.01; N, 14.23. Found: C, 56.49; H, 5.83; N, 14.28.

(5-(3-(2-amino-4-oxo-3,4-dihydro-5H-pyrrolo[3,2-d]pyrimidin-5-yl)propyl) thiophene-2-carbonyl)-L-glutamic acid (AGF331)

Using the general method for synthesis of target compounds, 7d (0.10 g, 0.2 mmol) was used to obtain AGF331 (0.054 g, 61%) as a white solid; TLC Rf=0.0 (MeOH:CHCl₃:HCl, 1:5:0.5); mp, 150.3-154.3° C.; ¹H-NMR (400 MHz) (Me₂SO-d₆) δ 12.20-11.10 (s, br, exch., 3H, COOH and NH), 8.49 (d, J=7.8 Hz, 1H, exch., —NH), 7.68 (d, J=3.8 Hz, 1H, Ar), 7.20 (d, J=2.8 Hz, 1H, Ar), 6.90 (d, J=3.8 Hz, 1H, Ar), 5.91 (d, J=2.8 Hz, 1H, Ar), 5.80 (s, 2H, exch., 2-NH₂), 4.31 (dt, J=28.9, 8.4 Hz, 3H, —CH and —CH₂—), 2.72 (t, J=7.7 Hz, 2H, —CH₂—), 2.33 (t, J=7.5 Hz, 2H, —CH₂—), 2.08 (dq, J=12.7, 6.5, 5.7 Hz, 2H, —CH₂—), 1.91 (m, 2H, —CH₂—). Anal. Calcd. for C₁₉H₂₁N₅O₅S 0.8 H₂O: C, 49.41; H, 4.93; N, 15.16; S, 6.94. Found: C, 49.44; H, 4.84; N, 15.13; S, 6.84.

(5-(4-(2-amino-4-oxo-3,4-dihydro-5H-pyrrolo[3,2-d]pyrimidin-5-yl)butyl)thiophene-2-carbonyl)-L-glutamic acid (AGF318)

Using the general method for synthesis of target compounds, 7e (0.10 g, 0.193 mmol) was used to obtain AGF318 (0.045 g, 50%) as a white solid; mp, 148.3-150.2° C.; TLC Rf=0.0 (MeOH:CHCl₃:HCl, 1:5:0.5); ¹H-NMR (400 MHz) (Me₂SO-d₆) δ 11.94 (s, 3H, exch., —COOH and NH), 8.54 (d, J=7.8 Hz, 1H, exch., —NH), 7.69 (d, J=7.8 Hz, 1H, Ar), 7.33 (d, J=3.8 Hz, 1H, Ar), 6.96 (s, 2H, exch., 2-NH₂), 6.85 (d, J=3.8 Hz, 1H, Ar), 6.01 (d, J=2.8 Hz, 1H, Ar), 4.38-4.23 (m, 3H, —CH— and —CH₂—), 2.79 (t, J=7.6 Hz, 2H, —CH₂—), 2.34 (t, J=7.4 Hz, 2H, —CH₂—), 2.14-1.92 (m, 2H, —CH₂—), 1.76 (p, J=6.9 Hz, 2H, —CH₂—), 1.52 (p, J=7.6 Hz, 2H, —CH₂—). Anal. Calcd. for C₂₀H₂₃N₅O₆S 0.58 HCl: C, 49.77; H, 4.92; N, 14.51; S, 6.64. Found: C, 49.80; H, 5.08; N, 14.51; S, 6.74.

(5-(5-(2-amino-4-oxo-3,4-dihydro-5H-pyrrolo[3,2-d]pyrimidin-5-yl)pentyl)thiophene-2-carbonyl)-L-glutamic acid (AGF320)

Using the general method for synthesis of target compounds, 7f (0.10 g, 0.188 mmol) was used to obtain AGF320 (0.072 g, 81%) as a white solid; mp, 73.4-78.7° C.; TLC Rf=0.0 (MeOH:CHCl$_3$:HCl, 1:5:0.5); $^1$H-NMR (400 MHz) (Me$_2$SO-d$_6$) δ 12.32 (s, 2H, exch., —COOH), 8.53 (d, J=7.9 Hz, 1H, exch., —NH), 7.69 (d, J=3.8 Hz, 1H, Ar), 7.34 (d, J=7.9 Hz, 1H, Ar), 7.09 (s, 2H, exch., 2-NH$_2$), 6.87 (d, J=3.8 Hz, 1H, Ar), 6.03 (d, J=2.8 Hz, 1H, Ar), 4.34 (d, J=2.8 Hz, 1H, —CH), 4.23 (t, J=7.0 Hz, 2H, —CH$_2$—), 2.77 (t, J=7.5 Hz, 2H, —CH$_2$—), 2.34 (t, J=7.5 Hz, 2H, —CH$_2$—), 1.92 (d, J=11.9 Hz, 2H, —CH$_2$—), 1.74 (m, 2H, —CH$_2$—), 1.61 (m, 2H, —CH$_2$—), 1.25 (t, J=7.5 Hz, 2H, —CH$_2$—). Anal. Calcd. for C$_{21}$H$_{25}$N$_5$O$_6$S 0.94 HCl: C, 49.48; H, 5.13; N, 13.74; S, 6.29. Found: C, 49.51; H, 5.21; N, 13.53; S, 6.31.

(4-(3-(2-amino-4-oxo-3,4-dihydro-5H-pyrrolo[3,2-d]pyrimidin-5-yl)propyl)-2-fluorobenzoyl)-L-glutamic acid (AGF359)

Using the general method for synthesis of target compounds, 7g (0.03 g, 0.07 mmol) was used to obtain AGF359 (0.04 g, 67%) as a white solid; TLC Rf=0.0 (MeOH:CHCl$_3$:HCl, 1:5:0.5); mp, 175.8-183.1° C.; $^1$H-NMR (400 MHz) (Me$_2$SO-d$_6$) δ 12.10-11.20 (s, br, 3H, exch., —COOH and —NH), 8.41 (dd, J=7.6, 2.7 Hz, 1H Ar), 7.53 (t, J=7.8 Hz, 1H, Ar), 7.28 (d, J=2.8 Hz, 1H, Ar), 7.17-7.09 (m, 2H), 6.50 (s, 2H), 5.98 (d, J=2.8 Hz, 1H), 4.39 (ddd, J=9.6, 7.6, 4.8 Hz, 1H), 4.27 (t, J=7.0 Hz, 2H), 2.61-2.54 (m, 2H), 2.40-2.31 (m, 2H), 2.11-2.03 (m, 3H), 1.90 (dddd, J=14.0, 9.5, 7.9, 6.3 Hz, 1H). MS calculated for C$_{21}$H$_{22}$FN$_5$O$_6$[M+H]$^+$, 460.16. Found: 460.0. HPLC analysis: retention time, 14.42 min; peak area, 96.2%; eluent A, H$_2$O: eluent B, ACN; gradient elution (100% H$_2$O to 10% H$_2$O) over 45 min with flow rate of 0.3 mL/min and detection at 254 nm; column temperature, rt.

(4-(4-(2-amino-4-oxo-3,4-dihydro-5H-pyrrolo[3,2-d]pyrimidin-5-yl)butyl)-2-fluorobenzoyl)-L-glutamic acid (AGF347)

Using the general method for synthesis of target compounds, 7h (0.40 g, 0.845 mmol) was used to obtain AGF347 (0.056 g, 63%) as a white solid; TLC Rf=0.0 (MeOH:CHC13:HCl, 1:5:0.5); mp, 161.6-162.4° C.; 1H-NMR (500 MHz) (Me2SO-d6) δ 8.43 (dd, J=7.6, 2.6 Hz, 1H, exch., —NH), 7.51 (t, J=7.7 Hz, 1H, Ar), 7.23 (d, J=2.9 Hz, 1H, Ar), 7.13-7.05 (m, 2H, Ar), 6.2 (s, 2H, exch., —NH$_2$), 5.92 (d, J=2.8 Hz, 1H, Ar), 4.38 (ddd, J=9.5, 7.5, 4.8 Hz, 1H, —CH), 4.25 (t, J=6.8 Hz, 2H, —CH$_2$—), 2.61 (t, J=7.7 Hz, 2H, —CH$_2$—), 2.40-2.28 (m, 2H, —CH$_2$—), 2.08-1.84 (m, 2H, —CH$_2$—), 1.72 (p, J=7.1 Hz, 2H, —CH$_2$—), 1.48 (td, J=8.5, 4.1 Hz, 2H, —CH$_2$—). Anal. Calcd. for C$_{22}$H$_{24}$FN$_5$O$_6$ 0.58 HCl: C, 55.81; H, 5.11; N, 14.79; F, 4.01 Found: C, 53.30; H, 5.15; N, 14.18; F, 3.81.

(4-(5-(2-amino-4-oxo-3,4-dihydro-5H-pyrrolo[3,2-d]pyrimidin-5-yl)pentyl)-2-fluorobenzoyl)-L-glutamic acid (AGF355)

Using the general method for synthesis of target compounds, 7i (0.05 g, 0.07 mmol) was used to obtain AGF355 (0.050 g, 56%) as a grey solid; TLC Rf=0.0 (MeOH:CHCl$_3$:HCl, 1:5:0.5); mp, 138.5-145.7° C.; $^1$H-NMR (400 MHz) (Me$_2$SO-d$_6$) δ 8.42 (d, J=9.0 Hz, 1H, exch., —NH), 7.52 (d, J=15.6 Hz, 1H, Ar), 7.19 (d, J=2.8 Hz, 1 H, Ar), 7.11 (d, J=25.0 Hz, 2H, Ar), 5.94 (s, 2H, exch., —NH$_2$), 5.89 (d, J=2.8 Hz, 1H, Ar), 4.39 (d, J=21.9 Hz, 1H, —CH), 4.20 (d, J=14.1 Hz, 2H, —CH$_2$—), 2.60 (d, J=15.7 Hz, 2H, —CH$_2$—), 2.38-2.32 (m, 2H, —CH$_2$—), 2.12-1.91 (m, 2H, —CH$_2$—), 1.73 (p, J=7.2 Hz, 2H, 1.57 (p, J=7.7 Hz, 2H, —CH$_2$—), 1.23 (d, J=51.8 Hz, 2H, —CH$_2$—). MS calculated for C$_{21}$H$_{22}$FN$_5$O$_6$[M+H]$^+$, 488.19. Found: 487.9. HPLC analysis: retention time, 12.75 min; peak area, 95.23%; eluent A, H$_2$O: eluent B, ACN; gradient elution (100% H$_2$O to 10% H$_2$O) over 45 min with flow rate of 0.3 mL/min and detection at 254 nm; column temperature, rt.

Scheme 1

SYNTHESIS SCHEMES:
For Formula I, Synthesis of AGF 323

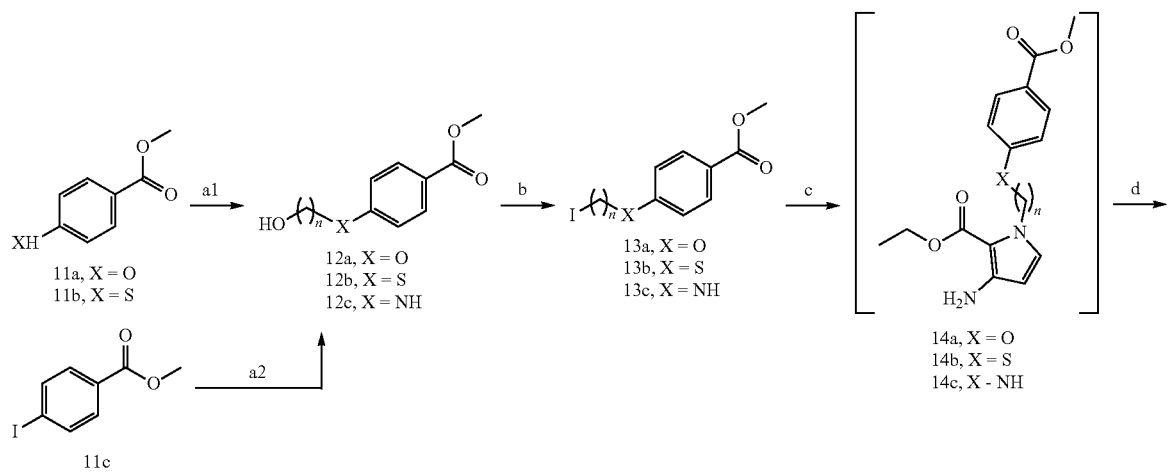

-continued

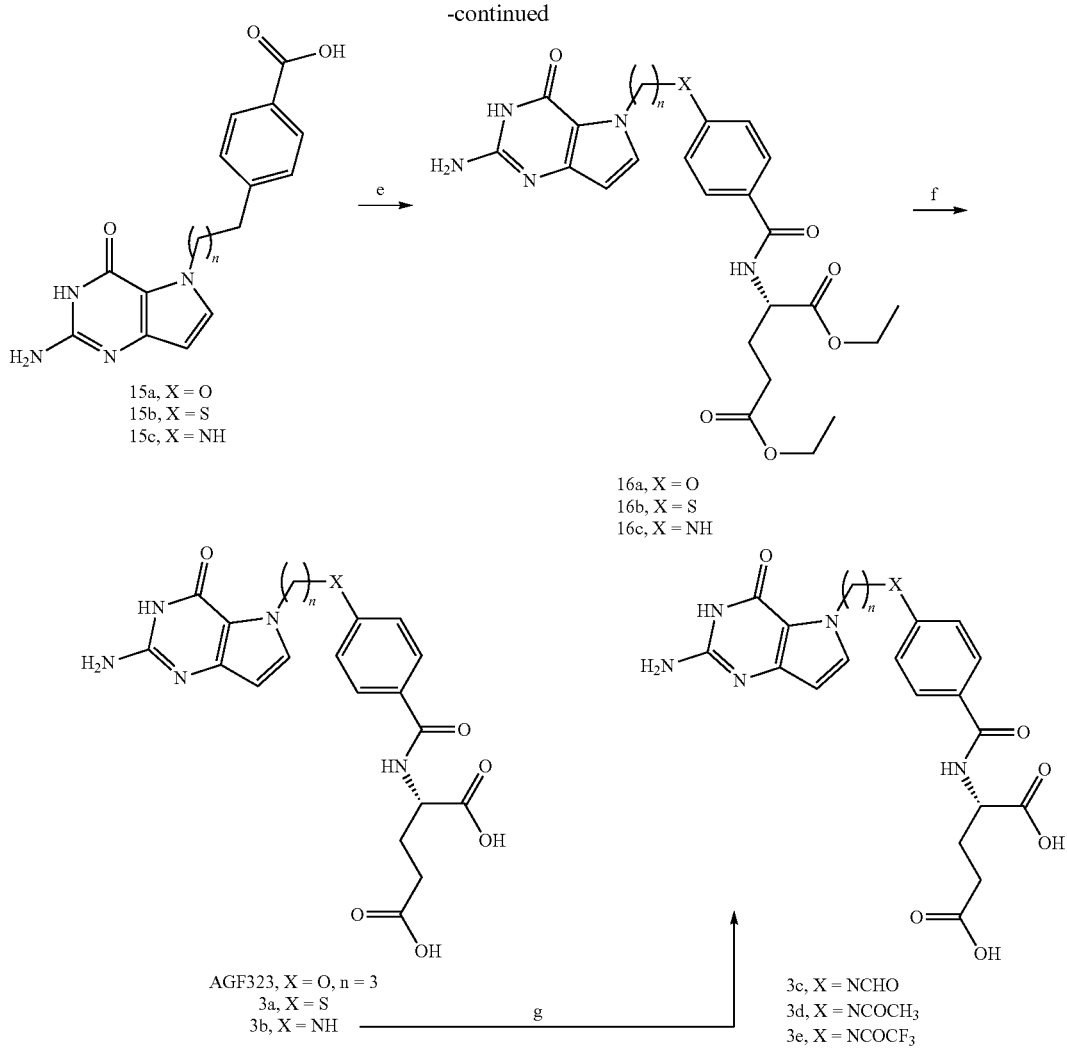

n = 2,4 a1) K$_2$CO$_3$, acetonitrile, 3-bromopropanol or 2-bromoethan-1-ol, reflux, 24 h; a2) 3-aminopropanol, CuI, L-proline, dimethyl sulfoxide, r.t., 48 h; b) PPh$_3$, iodine, imidazole, DCM, 0° C., 1.5 h; c) ethyl 3-amino-1H-pyrrole-2-carboxylate, NaH, DMF, 2 h, r.t.; d) (i) 1,3-bis(methoxycarbonyl)-2-methyl-2-thiopseudourea, MeOH, r.t., 16 h; (ii) NaOMe, MeOH, 16 h, r.t.; (iii) 1N NaOH, 55° C. 3 h; e) L-glutamic acid diethyl ester hydrochloride, 2-chloro-4,6-dimethoxy-triazine, NMM, anhydrous DMF, r.t., 12 h; f) 1N NaOH, r.t., 1 h; g) acetic anhydride, formic acid, 1 h, reflux, or acetic anhydride, rt, 12 h, or trifluoroacetic anhydride, rt, 4 h.

Synthesis of AGF323: Compound 11a was alkylated with 3-bromopropanol to afford alcohol 12a, which was subjected to the Appel reaction with PPh$_3$, imidazole and iodine to afford iodide 13a. Commercially available 3-amino-1H-pyrrole-2-carboxylate was then alkylated with 13a (61%) and the crude N-substituted pyrrole (14a) was directly subjected to condensation with 1,3-bis(methoxycarbonyl)-2-methylthiopseudourea with 5 equivalents of acetic acid as catalyst in MeOH. The hydrolysis of the carbamate group formed, was carried out in situ with aqueous sodium hydroxide at 55° C. to afford the 2-amino-4-oxo-pyrrolo[3,2-d]pyrimidine 15a (14%). Conversion of free acid 15a to the corresponding L-glutamic acid diethyl esters 16a (38%) involved conventional peptide coupling with L-glutamic acid diethyl ester hydrochloride using 2-chloro-4,6-dimethoxy-1,3,5-triazine followed by chromatographic purification. Hydrolysis of 16a with aqueous NaOH at room temperature, followed by acidification with 1 N HCl afforded the target compound AGF323 in 78% yields.

Additional Examples of Compounds of Formula 1

FORMULA I

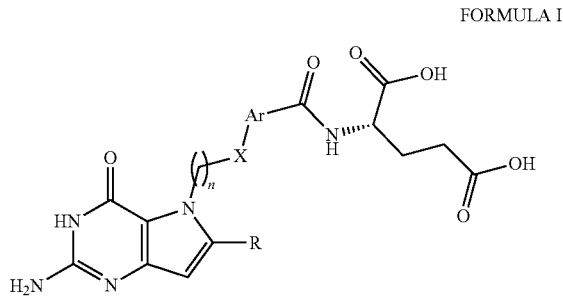

1 n=1, 3-4; R=H; X=CH$_2$; Ar=1',4'-phenyl or 2',5'-thienyl
2 n=1-4; R=CH$_3$; X=CH$_2$; Ar=1',4'-phenyl or 2',5'-thienyl 3 n=2-4; R=H; X=O, S, NH, NCHO, NCOCH₃, NCOCF₃; Ar=1',4'-phenyl or 2',5'-thienyl
4 n=2-4; R=H; X=CH₂; Ar=2'-fluoro-1',4'-phenyl
AGF291 n=2, Ar=1',4'-phenyl, R=H, X=CH₂
AGF299 n=4, Ar=1',4'-phenyl, R=H, X=CH₂
AGF300 n=3, Ar=1',4'-phenyl, R=H, X=CH₂
AGF307 n=4, Ar=1',4'-phenyl, R=CH₃, X=CH₂
AGF312 n=3, Ar=1',4'-phenyl, R=CH₃, X=CH₂
AGF318 n=3, Ar=2',5'-thienyl, R=H, X=CH₂
AGF320 n=4, Ar=2',5'-thienyl, R=H, X=CH₂
AGF323 n=3, Ar=1',4'-phenyl, R=H, X=O
AGF331 n=2, Ar=2',5'-thienyl, R=H, X=CH₂
AGF359 n=2, Ar=2'-fluoro-1',4'-phenyl, R=H, X=CH₂
AGF347 n=3, Ar=2'-fluoro-1',4'-phenyl, R=H, X=CH₂
AGF355 n=4, Ar=2'-fluoro-1',4'-phenyl, R=H, X=CH₂

For Formula I, Synthesis of AGF307, AGF312, AGF299, AGF359, AGF347 and AGF355:

Scheme 2

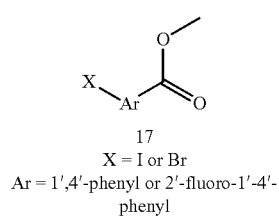

17
X = I or Br
Ar = 1',4'-phenyl or 2'-fluoro-1'-4'-phenyl

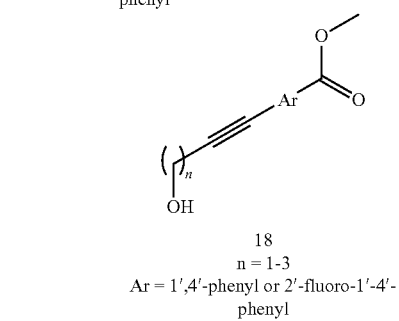

18
n = 1-3
Ar = 1',4'-phenyl or 2'-fluoro-1'-4'-phenyl

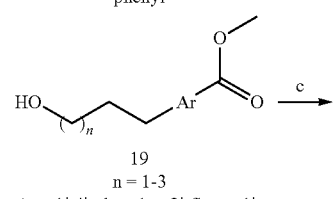

19
n = 1-3
Ar = 1',4'-phenyl or 2'-fluoro-1'-4'-phenyl

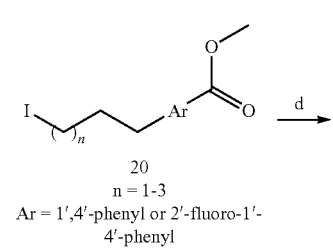

20
n = 1-3
Ar = 1',4'-phenyl or 2'-fluoro-1'-4'-phenyl

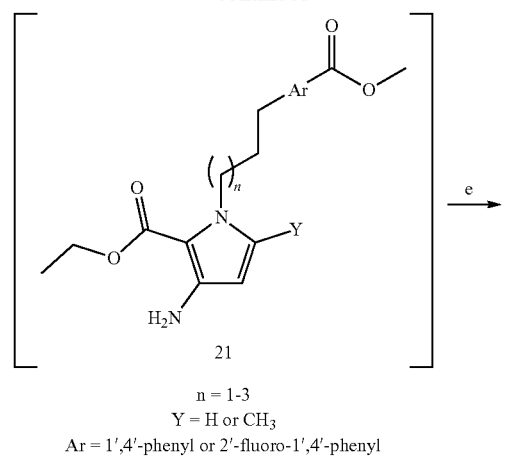

21
n = 1-3
Y = H or CH₃
Ar = 1',4'-phenyl or 2'-fluoro-1',4'-phenyl

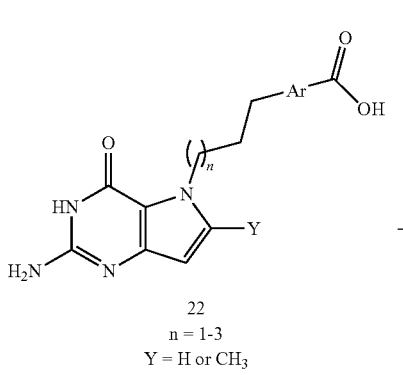

22
n = 1-3
Y = H or CH₃
Ar = 1',4'-phenyl or 2'-fluoro-1',4'-phenyl

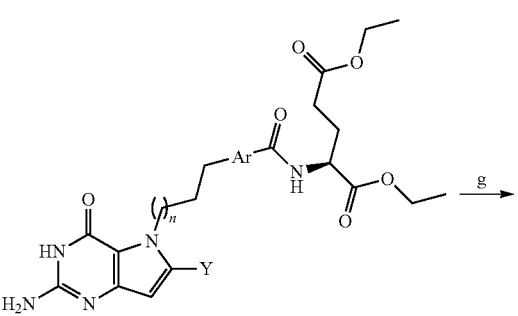

23
n = 1-3
Y = H or CH₃
Ar = 1',4'-phenyl or 2'-fluoro-1',4'-phenyl

-continued

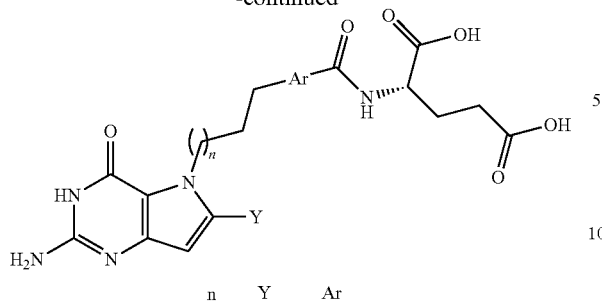

| | n | Y | Ar |
|---|---|---|---|
| AGF307 | 3 | CH₃ | 1',4'-phenyl |
| AGF312 | 2 | CH₃ | 1',4'-phenyl |
| AGF299 | 3 | H | 1',4'-phenyl |
| AGF359 | 1 | H | 2'-fluoro-1',4'-phenyl |
| AGF347 | 2 | H | 2'-fluoro-1',4'-phenyl |
| AGF355 | 3 | H | 2'-fluoro-1',4'-phenyl | a) PdCl₂, PPh₃, TEA, CuI, alcohol, acetonitrile, 1 h, 100° C., microwave; b) H₂/Pd, high parr vessel, 24 h, r.t.; c) (i) mesyl chloride, TEA, DCM, 0° C., 2 h; (ii) NaI, acetone, 4 h, reflux; d) ethyl-3-amino-1H-pyrrole-2-carboxylate or ethyl 3-amino-5-methyl-1H-pyrrole-2-carboxylate, NaH, DMF, 2 h, r.t.; e) (i) 1,3-bis(methoxycarbonyl)-2-methyl-2-thiopseudourea, MeOH, r.t., 16 h; (ii) NaOMe, MeOH, 16 h, r.t.; (iii) 1N NaOH, 55° C., 3 h; f) L-glutamic acid diethyl ester hydrochloride, 2-chloro-4,6-dimethoxy-triazine, NMM, DMF, r.t., 12 h; g) 1N NaOH, r.t., 1 h Synthesis of the target compounds AGF299, AGF307, AGF312, AGF359, AGF347 and AGF355 started with a palladium-catalyzed Sonogashira coupling of 4-iodobenzoate methyl ester or methyl 4-bromo-2-fluorobenzoate with the appropriate alkyne alcohols to afford the appropriate 4-substituted alcohol benzoates 18 (78-88%). Catalytic hydrogenation afforded the saturated alcohols 19 (85-98%). The alcohols were converted to the mesylate derivatives using mesyl chloride and triethylamine base at 0° C. The mesylate derivatives were converted to their respective iodide 20 (72-85%) using the Finkelstein reaction. The N-alkylation of iodides, using ethyl 3-amino-1H-pyrrole-2-carboxylate or ethyl 3-amino-5-methyl-1H-pyrrole-2-carboxylate and sodium hydride under anhydrous conditions afforded the N-5 substituted pyrroles 21. The crude N-substituted pyrroles (21) were directly subjected to condensation with 1,3-bis(methoxycarbonyl)-2-methylthiopseudourea with 5 equivalents of acetic acid as catalyst and MeOH. The hydrolysis of the carbamate group formed was carried out in situ with aqueous sodium hydroxide at 55° C. to afforded the 2-amino-4-oxo-pyrrolo[3,2-d]pyrimidines 22 (23-30%). Conversion of free acids (22) to the corresponding L-glutamic acid diethyl esters 23 (32-75%) involved conventional peptide coupling with L-glutamic acid diethyl ester hydrochloride using 2-chloro-4,6-dimethoxy-1,3,5-triazine followed by chromatographic purification to afford the coupled products. Hydrolysis of 23 with aqueous NaOH at room temperature, followed by acidification with 1 N HCl in the cold, afforded target compounds AGF299, AGF307, AGF312, AGF347, AGF355 and AGF359 in 25-67% yield. For Formula II, Synthesis of AGF287:

Scheme 3

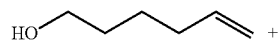

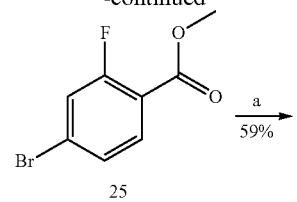

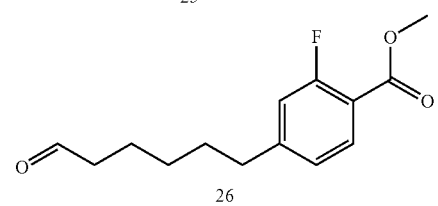

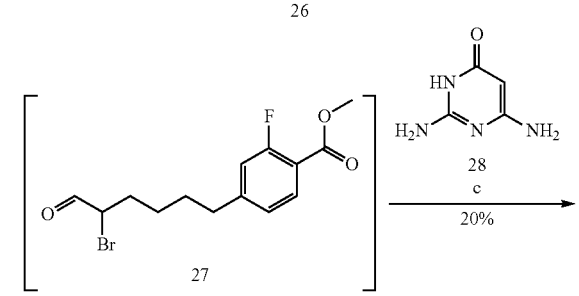

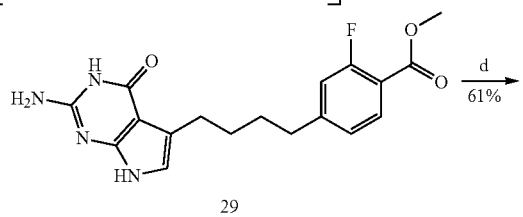

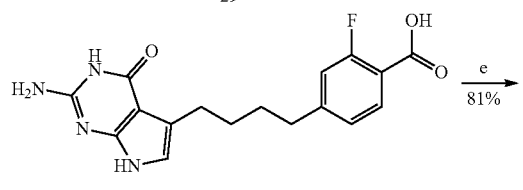

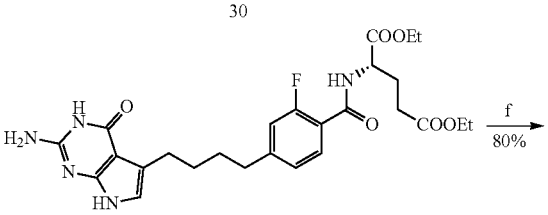

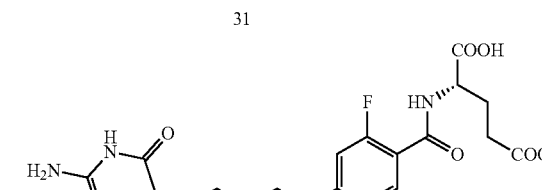

AGF287

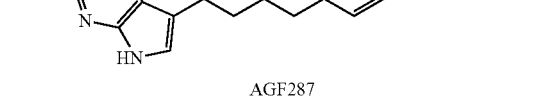

Reagents and conditions: (a) Pd(OAc)₂, LiCl, LiOAc, Bu₄NCl, DMF, 90° C., 2.5 h, 59%; (b) 5,5-dibromo-2,2-dimethyl-4,6-dioxo-1,3-dioxane 302, 1N HCl in (Et)₂O, (Et)₂O, rt, 48 h; (c) CH₃COONa, MeOH, H₂O, 45° C., 4 h, 20% yield over 2 steps; (d) (i) 1N NaOH, rt, 12 h; (ii) 1N HCl, 61% yield; (e) NMM, CDMT, diethyl-L-glutamate, DMF, rt, 12 h, 81%; (f) (i) 1N, NaOH, rt, 1 h; (ii) 0-4° C., 1N HCl, 80%.

Synthesis of AGF287: Heck coupling reaction of commercially available hex-5-en-1-ol 24 and methyl 4-bromo-2-fluorobenzoate 25 afforded the unsaturated, coupled alcohol that rearranged to the vinyl alcohol and tautomerized to afford the aldehyde 26 in 59% yield. Subsequent α-bromination of 26 with 5,5-dibromo-2,2-dimethyl-4,6-dioxo-1,3-dioxane (DBMA) at room temperature afforded corresponding α-bromo aldehyde 27, which was immediately condensed with 2,6-diamino-4-oxo-pyrimidine 28 in the presence of sodium acetate to afford the 5-substituted pyrolo[2,3-d]pyrimidine 29 in 20% yield over 2 steps. The terminal ester of 29 was subjected to base catalyzed hydrolysis to afford the pteroic acid 30 in 61% yield. The acid 30 was subsequently peptide coupled with L-glutamate diethyl ester hydrochloride in the presence of NMM and CDMT as the coupling agents to afford the diester 31 in 81% yield. Final saponification of the diesters with 1 N NaOH and neutralization to pH 4, provided target compound AGF287 in 80% yield.

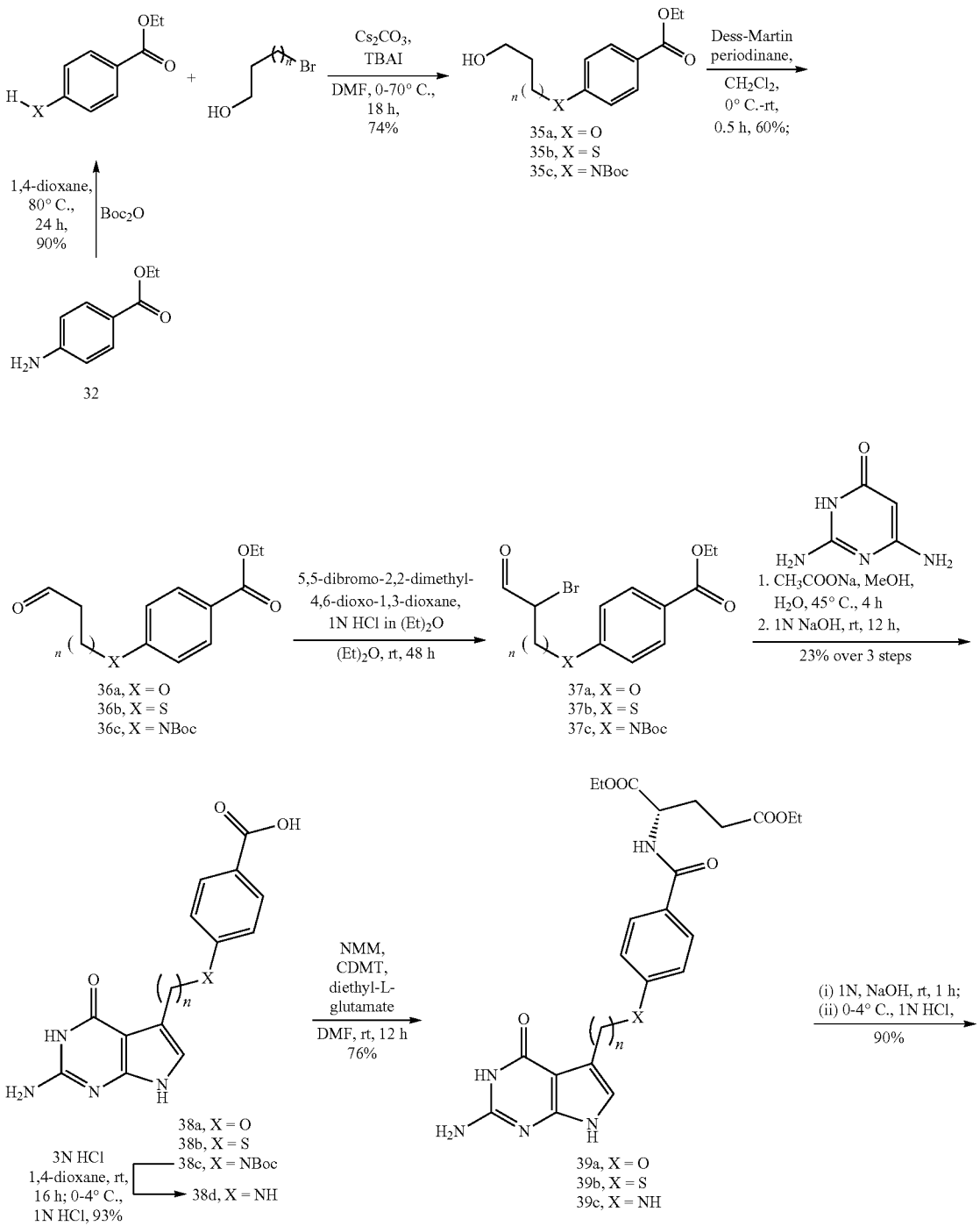

Scheme 4

-continued
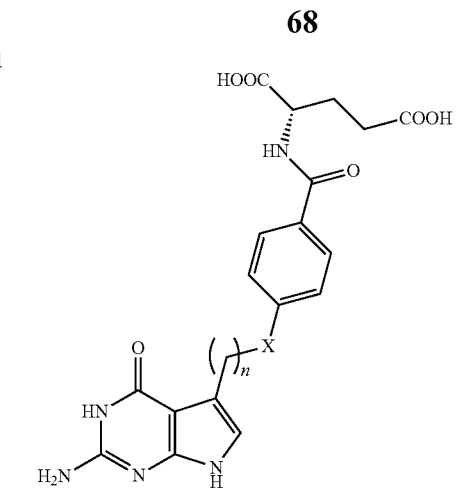
6a, X = O
6b, X = S
6c, X = NH
6d, X = NCHO
6e, X = NCOCH₃
6f, X = NCOCF₃
acetic anhydride, formic acid, 1 h, reflux or acetic anhydride, rt, 12 h, or trifluoroacetic anhydride, rt, 4 h
n = 1-4
For Formula III, Synthesis of AGF 315 and AGF 317
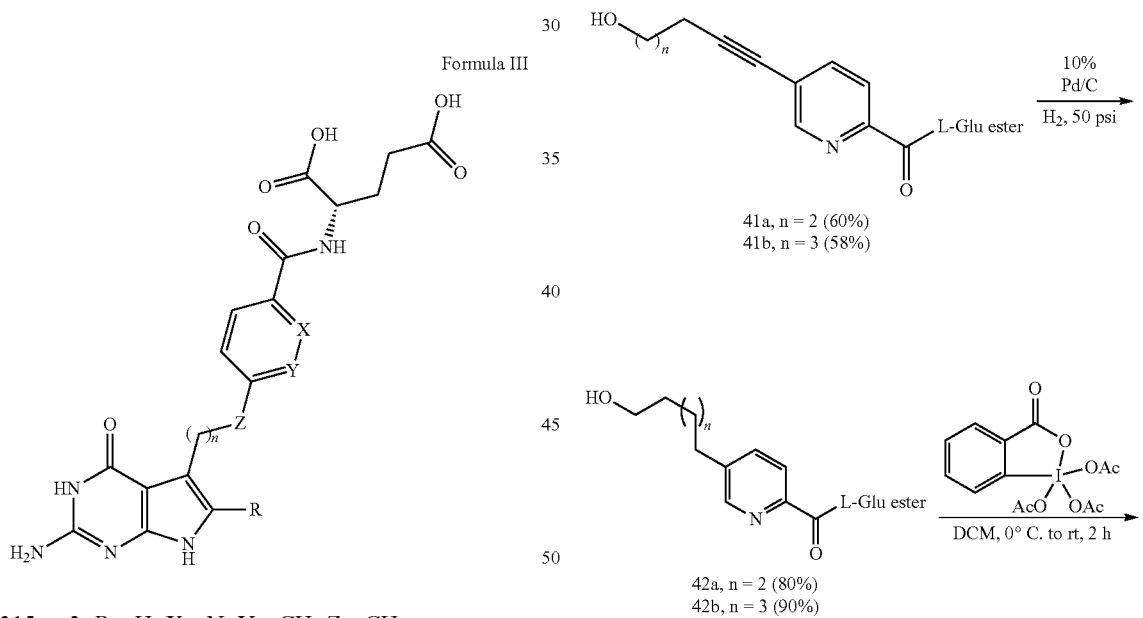
Formula III
AGF315 n=2, R=H, X=N, Y=CH, Z=CH₂
AGF317 n=3, R=H, X=N, Y=CH, Z=CH₂
Scheme 5
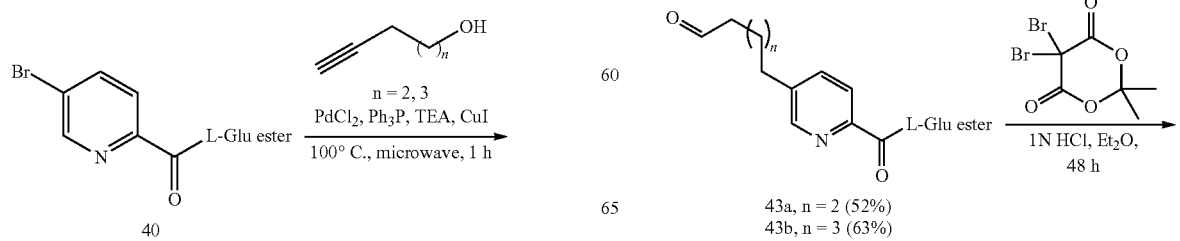
41a, n = 2 (60%)
41b, n = 3 (58%)
42a, n = 2 (80%)
42b, n = 3 (90%)
43a, n = 2 (52%)
43b, n = 3 (63%)

69
-continued

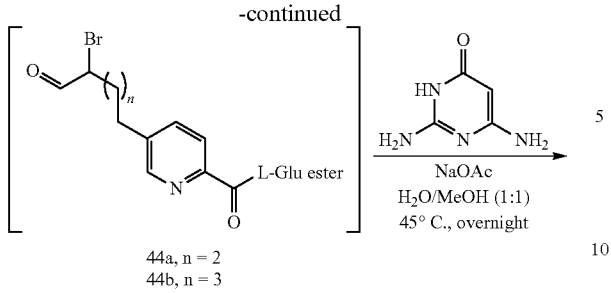

44a, n = 2
44b, n = 3

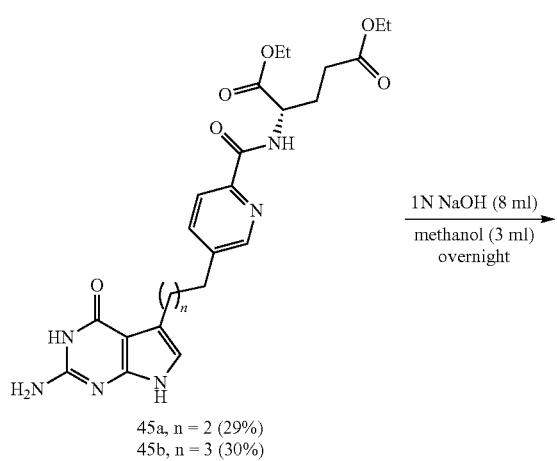

45a, n = 2 (29%)
45b, n = 3 (30%)

70
-continued

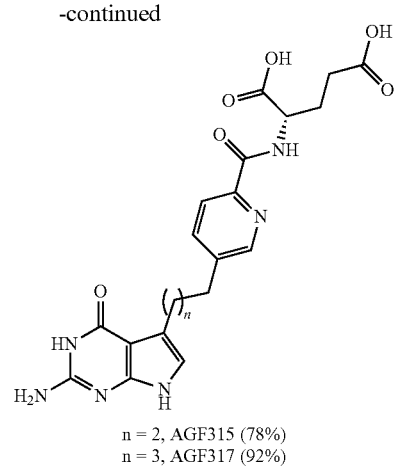

n = 2, AGF315 (78%)
n = 3, AGF317 (92%)

Synthesis of AGF315 and AGF317: Sonogashira coupling of 5-bromo picolinic L-glu ethyl ester (40) with corresponding alkyn-1-ol gave compound 41 (scheme 5). Hydrogenation of triple bond of alkyne gave compound 42. Oxidation of hydroxyl group of compound 42 using DMP gave aldehydes 43. Alpha bromination of aldehydes 43 with DMBA gave α-bromo aldehyde 44 which was used for next reaction without purification. Cyclization of α-bromo aldehyde 44 with 2,6-diamino-4-oxopyrimidine gave pyrrolo[2,3-d]pyrimidine 45. Hydrolysis of ester 45 produced final compounds AGF315 and AGF317.

Scheme 6

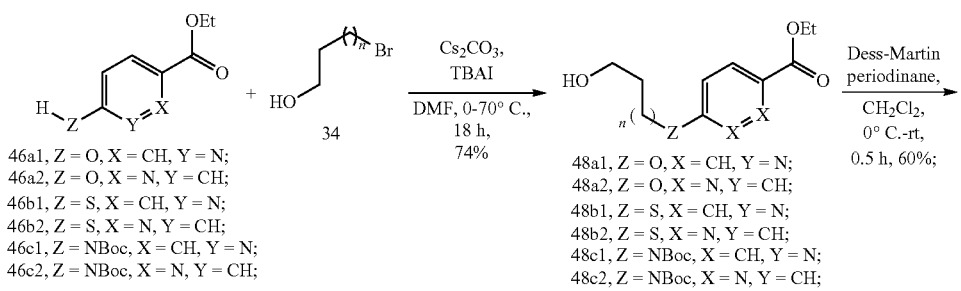

46a1, Z = O, X = CH, Y = N;
46a2, Z = O, X = N, Y = CH;
46b1, Z = S, X = CH, Y = N;
46b2, Z = S, X = N, Y = CH;
46c1, Z = NBoc, X = CH, Y = N;
46c2, Z = NBoc, X = N, Y = CH;

48a1, Z = O, X = CH, Y = N;
48a2, Z = O, X = N, Y = CH;
48b1, Z = S, X = CH, Y = N;
48b2, Z = S, X = N, Y = CH;
48c1, Z = NBoc, X = CH, Y = N;
48c2, Z = NBoc, X = N, Y = CH;

1,4-dioxane, 80° C., 24 h, 90% | Boc₂O

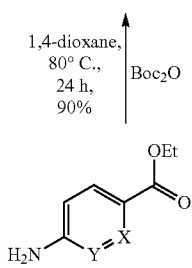

47a X = CH, Y = N
47b X = N, Y = CH

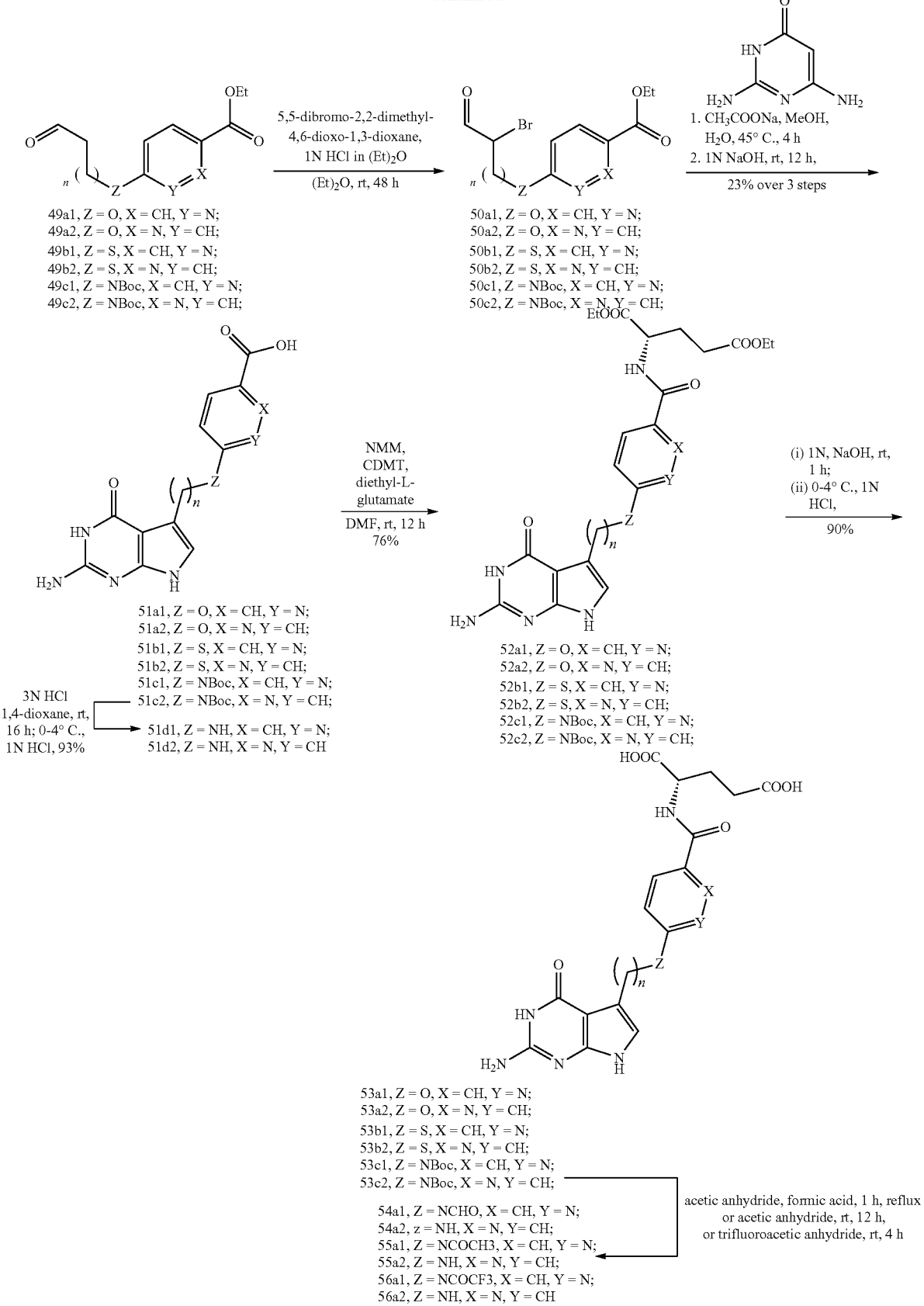

Inhibitors of cytosolic C1 metabolism were among the first chemotherapy agents used for cancer and continue to be a mainstay for treating many cancers (8). However, the clinical utility of standard chemotherapy drugs is often limited by their toxicities toward normal tissues (reflecting a lack of tumor selectivity) and/or drug resistance. Discovery of new and potent inhibitors of tumor-selective pathways, while essential, remains a formidable challenge.

This invention provides compounds and pharmaceutically acceptable salts thereof as novel inhibitors of C1 metabolism in mitochondria, the primary catabolic pathway for serine and for synthesis of glycine (2-5). Serine catabolism in mitochondria is the principal source of C1 units for cytosolic de novo purine and thymidylate biosynthesis, and of reducing equivalents and ATP (2-5, 40). For SHMT2, the first enzyme in the mitochondrial C1 pathway, CRISPR-Cas9 deletion in cultured cells results in defective mitochondrial respiration due to impaired synthesis of respiratory chain proteins (40, 41), accompanied by a commensurate increase in glycolytic flux (40). We targeted SHMT2 with a novel series of 5-substituted pyrrolo[3,2-d]pyrimidine compounds of this invention, and we identify lead compounds of this invention, namely, AGF291, AGF320 and AGF347 that inhibited proliferation of a broad spectrum of tumor subtypes including lung (H460), colon (HCT116), and pancreatic (MIA PaCa-2) cancer.

We identified critical enzyme targets of our compounds through glycine/nucleoside protection experiments and targeted metabolomics with a [2,3,3-$^2$H]serine tracer, and identified SHMT2 in mitochondria as the principal intracellular target, along with SHMT1, and GARFTase and/or AICARFTase in the cytosol. Inhibition of all these intracellular targets was confirmed by in vitro assays with purified recombinant enzymes. Our finding that SHMT1 is a direct target of our compounds resembles results for a dual-SHMT1/SHMT2 pyrazolopyran inhibitor SHIN1 (21) and is of particular interest as this prevents metabolic "compensation" by reversal of SHMT1 catalysis in response to loss of SHMT2 activity (20, 21).

Not to be bound by any particular theory, a number of pharmacodynamic factors could contribute to the in vitro anti-tumor effects of the novel compounds of this invention. These include transport across the plasma membrane by PCFT and/or RFC and into mitochondria (potentially by the mitochondrial folate transporter (11, 12)), metabolism to drug polyglutamates, analogous to pemetrexed and other classic antifolates (6, 8), and binding to intracellular targets in both the mitochondria and the cytosol. Variations in these parameters likely account for differences in relative antiproliferative activities toward the assorted tumor models in this report. As compound of the present invention AGF291 showed selectivity for PCFT over RFC, this compound was further tested in vivo with a MIA PaCa-2 xenograft model in SCID mice. AGF291 exhibited potent in vivo anti-tumor efficacy exceeding that of GEM (standard-of-care for PaC), albeit at a 20-fold decreased dose.

The active 5-substituted pyrrolo[3,2-d]pyrimidine compounds described herein expand upon earlier results with non-folate pyrazolopyran inhibitors of human SHMT2 (21) and, to our knowledge, represent the first bona fide inhibitors of this intracellular target with demonstrated in vivo antitumor efficacy. Thus, inhibition of SHMT2, coupled with direct inhibition of multiple C1-dependent targets including de novo purine biosynthesis and SHMT1, afford a valuable and exciting new platform for future drug development for a variety of tumors.

The mouse work reported in this application was approved by the Wayne State University Institutional Animal Care and Use Committee. For metabolite measurements by targeted metabolomics, cultured cells were incubated in media containing dialyzed fetal bovine serum and the isotopically labeled serine. For the 5-substituted pyrrolo[3,2-d]pyrimidine compounds of this invention, complete chemical synthesis and compound characterizations are provided herein. These and all other experimental procedures are all described in detail herein.

REFERENCES

1. Hanahan D & Weinberg Robert A (2011) Hallmarks of Cancer: The Next Generation. Cell 144(5):646-674.
2. Newman A C & Maddocks O D K (2017) One-carbon metabolism in cancer. British Journal of Cancer 116(12): 1499-1504.
3. Yang M & Vousden K H (2016) Serine and one-carbon metabolism in cancer. Nat Rev Cancer 16(10):650-662.
4. Ducker G S & Rabinowitz J D (2017) One-Carbon Metabolism in Health and Disease. Cell Metabolism 25(1):27-42.
5. Tibbetts A S & Appling D R (2010) Compartmentalization of Mammalian folate-mediated one-carbon metabolism. Annu Rev Nutr 30:57-81.
6. Chattopadhyay S, Moran R G, & Goldman I D (2007) Pemetrexed: biochemical and cellular pharmacology, mechanisms, and clinical applications. Molecular cancer therapeutics 6(2):404-417.
7. Matherly L H, Wilson M R, & Hou Z (2014) The major facilitative folate transporters solute carrier 19A1 and solute carrier 46A1: biology and role in antifolate chemotherapy of cancer. Drug Metab Dispos 42(4):632-649.
8. Visentin M, Zhao R, & Goldman I D (2012) The Antifolates. Hematology/oncology clinics of North America 26(3):629-ix.
9. Matherly L H, Hou Z, & Deng Y (2007) Human reduced folate carrier: translation of basic biology to cancer etiology and therapy. Cancer metastasis reviews 26(1):111-128.
10. Zhao R D-B, Ndeye; Visentin, Michele; Goldman, David I. (2011) Mechanisms of Membrane Transport of Folates into Cells and Across Epithelia. Annual Review of Nutrition 31(1):177-201.
11. McCarthy E A, Titus S A, Taylor S M, Jackson-Cook C, & Moran R G (2004) A mutation inactivating the mitochondrial inner membrane folate transporter creates a glycine requirement for survival of chinese hamster cells. J Biol Chem 279(32):33829-33836.
12. Lawrence S A, Hackett J C, & Moran R G (2011) Tetrahydrofolate Recognition by the Mitochondrial Folate Transporter. J Biol Chem 286(36):31480-31489.
13. Lawrence S A, et al. (2014) Mammalian mitochondrial and cytosolic folylpolyglutamate synthetase maintain the subcellular compartmentalization of folates. J Biol Chem 289(42):29386-29396.
14. Jain M, et al. (2012) Metabolite Profiling Identifies a Key Role for Glycine in Rapid Cancer Cell Proliferation. Science (New York, N.Y.) 336(6084):1040-1044.
15. Kim D, et al. (2015) SHMT2 drives glioma cell survival in the tumor microenvironment but imposes a dependence on glycine clearance. Nature 520(7547):363-367.
16. Nilsson R, et al. (2014) Metabolic enzyme expression highlights a key role for MTHFD2 and the mitochondrial folate pathway in cancer. Nature communications 5:3128.

17. Zhang L, et al. (2016) Prognostic and therapeutic value of mitochondrial serine hydroxyl-methyltransferase 2 as a breast cancer biomarker. *Oncology reports* 36(5):2489-2500.
18. Loayza-Puch F, et al. (2016) Tumour-specific proline vulnerability uncovered by differential ribosome codon reading. *Nature* 530(7591):490-494.
19. Ye J, et al. (2014) Serine catabolism regulates mitochondrial redox control during hypoxia. *Cancer discovery* 4(12): 1406-1417.
20. Ducker G S, et al. (2016) Reversal of Cytosolic One-Carbon Flux Compensates for Loss of the Mitochondrial Folate Pathway. *Cell Metab* 23(6):1140-1153.
21. Ducker G S, et al. (2017) Human SHMT inhibitors reveal defective glycine import as a targetable metabolic vulnerability of diffuse large B-cell lymphoma. *Proceedings of the National Academy of Sciences* 114(43):11404-11409.
22. Lee G Y, et al. (2014) Comparative oncogenomics identifies PSMB4 and SHMT2 as potential cancer driver genes. *Cancer Res* 74(11):3114-3126.
23. Deng Y, et al. (2008) Synthesis and Discovery of High Affinity Folate Receptor-Specific Glycinamide Ribonucleotide Formyltransferase Inhibitors With Antitumor Activity. *Journal of medicinal chemistry* 51(16):5052-5063.
24. Deng Y, et al. (2009) Synthesis and biological activity of a novel series of 6-substituted thieno[2,3-d]pyrimidine antifolate inhibitors of purine biosynthesis with selectivity for high affinity folate receptors over the reduced folate carrier and proton-coupled folate transporter for cellular entry. *J Med Chem* 52(9):2940-2951.
25. Golani L K, et al. (2016) Tumor Targeting with Novel 6-Substituted Pyrrolo [2,3-d] Pyrimidine Antifolates with Heteroatom Bridge Substitutions Via Cellular Uptake by Folate Receptor α and the Proton-coupled Folate Transporter and Inhibition of De Novo Purine Nucleotide Biosynthesis. *Journal of medicinal chemistry* 59(17): 7856-7876.
26. Mitchell-Ryan S, et al. (2013) Discovery of 5-substituted pyrrolo[2,3-d]pyrimidine antifolates as dual acting inhibitors of glycinamide ribonucleotide formyltransferase and 5-aminoimidazole-4-carboxamide ribonucleotide formyltransferase in de novo purine nucleotide biosynthesis: implications of inhibiting 5-aminoimidazole-4-carboxamide ribonucleotide formyltransferase to AMPK activation and anti-tumor activity. *J Med Chem* 56(24):10016-10032.
27. Wang L, et al. (2011) Synthesis, biological and antitumor activity of a highly potent 6-substituted pyrrolo[2,3-d] pyrimidine thienoyl antifolate inhibitor with proton-coupled folate transporter and folate receptor selectivity over the reduced folate carrier that inhibits β-glycinamide ribonucleotide formyltransferase. *Journal of medicinal chemistry* 54(20):7150-7164.
28. Wang Y, et al. (2015) Novel 5-substituted pyrrolo[2,3-d]pyrimidines as dual inhibitors of glycinamide ribonucleotide formyltransferase and 5-aminoimidazole-4-carboxamide ribonucleotide formyltransferase and as potential antitumor agents. *J Med Chem* 58(3): 1479-1493.
29. Ravindra M P, et al. (2018) Fluorinated Substituted Pyrrolo[2,3-d]Pyrimidine Antifolates With Tumor-Targeting Via Cellular Uptake by Folate Receptor α and the Proton-coupled Folate Transporter and Inhibition of De Novo Purine Nucleotide Biosynthesis. *Journal of medicinal chemistry*.
30. Flintoff W F, Davidson S V, & Siminovitch L (1976) Isolation and partial characterization of three methotrexate-resistant phenotypes from Chinese hamster ovary cells. *Somatic Cell and Molecular Genetics* 2(3):245-261.
31. Desmoulin S K, Hou Z, Gangj ee A, & Matherly L H (2012) The human proton-coupled folate transporter: Biology and therapeutic applications to cancer. *Cancer Biology & Therapy* 13(14):1355-1373.
32. Mitchell-Ryan S, et al. (2013) Discovery of 5-substituted pyrrolo[2,3-d]pyrimidine antifolates as dual-acting inhibitors of glycinamide ribonucleotide formyltransferase and 5-aminoimidazole-4-carboxamide ribonucleotide formyltransferase in de novo purine nucleotide biosynthesis: implications of inhibiting 5-aminoimidazole-4-carboxamide ribonucleotide formyltransferase to ampk activation and antitumor activity. *J. Med. Chem.* 56:10016-10032.
33. Fu T F, Scarsdale J N, Kazanina G, Schirch V, & Wright H T (2003) Location of the pteroylpolyglutamate-binding site on rabbit cytosolic serine hydroxymethyltransferase. *J Biol Chem* 278(4):2645-2653.
34. Wilson M R, et al. (2016) Targeting Nonsquamous Nonsmall Cell Lung Cancer via the Proton-Coupled Folate Transporter with 6-Substituted Pyrrolo[2,3-d]Pyrimidine Thienoyl Antifolates. *Molecular Pharmacology* 89(4):425-434.
35. Kugel Desmoulin S, et al. (2011) Therapeutic Targeting of a Novel 6-Substituted Pyrrolo [2,3-d]pyrimidine Thienoyl Antifolate to Human Solid Tumors Based on Selective Uptake by the Proton-Coupled Folate Transporter. *Molecular Pharmacology* 80(6):1096-1107.
36. Altschul S F, et al. (2005) Protein database searches using compositionally adjusted substitution matrices. *The FEBS journal* 272(20):5101-5109.
37. Altschul S F, Gish W, Miller W, Myers E W, & Lipman D J (1990) Basic local alignment search tool. *Journal of molecular biology* 215(3):403-410.
38. Cheong C G, et al. (2004) Crystal structures of human bifunctional enzyme aminoimidazole-4-carboxamide ribonucleotide transformylase/IMP cyclohydrolase in complex with potent sulfonyl-containing antifolates. *J Biol Chem* 279(17):18034-18045.
39. Deis S M, et al. (2016) Structural and Enzymatic Analysis of Tumor-Targeted Antifolates That Inhibit Glycinamide Ribonucleotide Formyltransferase. *Biochemistry* 55(32):4574-4582.
40. Morscher R J, et al. (2018) Mitochondrial translation requires folate-dependent tRNA methylation. *Nature* 554 (7690):128-132.
41. Minton D R, et al. (2018) Serine Catabolism by SHMT2 Is Required for Proper Mitochondrial Translation Initiation and Maintenance of Formylmethionyl-tRNAs. *Mol Cell* 69(4):610-621 e615.
42. Ducker, G. S., Ghergurovich, J. M., Mainolfi, N., Suri, V., Jeong, S. K., Hsin-Jung Li, S., Friedman, A., Manfredi, M. G., Gitai, Z., Kim, H., and Rabinowitz, J. D. (2017) Human SHMT inhibitors reveal defective glycine import as a targetable metabolic vulnerability of diffuse large B-cell lymphoma. *Proceedings of the National Academy of Sciences* 114, 11404-11409
43. Fu, T. F., Scarsdale, J. N., Kazanina, G., Schirch, V., and Wright, H. T. (2003) Location of the pteroylpolyglutamate-binding site on rabbit cytosolic serine hydroxymethyltransferase. *J Biol Chem* 278, 2645-2653
44. Schrödinger Release 2018-1: Maestro, Schrödinger, LLC, New York, N.Y., 2018.

45. Schrödinger Release 2018-1: Schrödinger Suite 2018-1 Induced Fit Docking protocol; Glide, Schrödinger, LLC, New York, N.Y., 2016; Prime, Schrödinger, LLC, New York, N.Y., 2018.
46. Wang, L., Desmoulin, S. K., Cherian, C., Polin, L., White, K., Kushner, J., Fulterer, A., Chang, M.-H., Mitchell, S., Stout, M., Romero, M. F., Hou, Z., Matherly, L. H., and Gangjee, A. (2011) Synthesis, biological and antitumor activity of a highly potent 6-substituted pyrrolo[2,3-d]pyrimidine thienoyl antifolate inhibitor with proton-coupled folate transporter and folate receptor selectivity over the reduced folate carrier that inhibits β-glycinamide ribonucleotide formyltransferase. *Journal of medicinal chemistry* 54, 7150-7164
47. Ducker, G. S., Ghergurovich, J. M., Mainolfi, N., Suri, V., Jeong, S. K., Hsin-Jung Li, S., Friedman, A., Manfredi, M. G., Gitai, Z., Kim, H., and Rabinowitz, J. D. (2017) Human SHMT inhibitors reveal defective glycine import as a targetable metabolic vulnerability of diffuse large B-cell lymphoma. *Proceedings of the National Academy of Sciences* 114, 11404-11409
48. Newman, A. C., and Maddocks, O. D. K. (2017) One-carbon metabolism in cancer. *British Journal of Cancer* 116, 1499-1504
49. Yang, M., and Vousden, K. H. (2016) Serine and one-carbon metabolism in cancer. *Nat Rev Cancer* 16, 650-662
50. Ducker, G. S., and Rabinowitz, J. D. (2017) One-Carbon Metabolism in Health and Disease. *Cell Metabolism* 25, 27-42
51. Tibbetts, A. S., and Appling, D. R. (2010) Compartmentalization of Mammalian folate-mediated one-carbon metabolism. *Annu Rev Nutr* 30, 57-81
52. Fu, T. F., Scarsdale, J. N., Kazanina, G., Schirch, V., and Wright, H. T. (2003) Location of the pteroylpolyglutamate-binding site on rabbit cytosolic serine hydroxymethyltransferase. *J Biol Chem* 278, 2645-2653
53. Ducker, G. S., Chen, L., Morscher, R. J., Ghergurovich, J. M., Esposito, M., Teng, X., Kang, Y., and Rabinowitz, J. D. (2016) Reversal of Cytosolic One-Carbon Flux Compensates for Loss of the Mitochondrial Folate Pathway. *Cell Metab* 23, 1140-1153
54. Flintoff, W. F., Davidson, S. V., and Siminovitch, L. (1976) Isolation and partial characterization of three methotrexate-resistant phenotypes from Chinese hamster ovary cells. *Somatic Cell and Molecular Genetics* 2, 245-261
55. Deng, Y., Wang, Y., Cherian, C., Hou, Z., Buck, S. A., Matherly, L. H., and Gangjee, A. (2008) Synthesis and Discovery of High Affinity Folate Receptor-Specific Glycinamide Ribonucleotide Formyltransferase Inhibitors With Antitumor Activity. *Journal of medicinal chemistry* 51, 5052-5063
56. Deng, Y., Zhou, X., Desmoulin, S. K., Wu, J., Cherian, C., Hou, Z., Matherly, L. H., and Gangjee, A. (2009) Synthesis and biological activity of a novel series of 6-substituted thieno[2,3-d]pyrimidine antifolate inhibitors of purine biosynthesis with selectivity for high affinity folate receptors over the reduced folate carrier and proton-coupled folate transporter for cellular entry. *J Med Chem* 52, 2940-2951
57. Wong, S. C., Proefke, S. A., Bhushan, A., and Matherly, L. H. (1995) Isolation of human cDNAs that restore methotrexate sensitivity and reduced folate carrier activity in methotrexate transport-defective Chinese hamster ovary cells. *J Biol Chem* 270, 17468-17475
58. Wilson, M. R., Hou, Z., Yang, S., Polin, L., Kushner, J., White, K., Huang, J., Ratnam, M., Gangjee, A., and Matherly, L. H. (2016) Targeting Nonsquamous Nonsmall Cell Lung Cancer via the Proton-Coupled Folate Transporter with 6-Substituted Pyrrolo[2,3-d]Pyrimidine Thienoyl Antifolates. *Molecular Pharmacology* 89, 425-434
59. Lowry, O. H., Rosebrough, N. J., Farr, A. L., and Randall, R. J. (1951) Protein measurement with the Folin phenol reagent. *J Biol Chem* 193, 265-275
60. Laemmli, U. K. (1970) Cleavage of structural proteins during the assembly of the head of bacteriophage T4. *Nature* 227, 680-685
61. Matsudaira, P. (1987) Sequence from picomole quantities of proteins electroblotted onto polyvinylidene difluoride membranes. *J Biol Chem* 262, 10035-10038
62. Cherian, C., Kugel Desmoulin, S., Wang, L., Polin, L., White, K., Kushner, J., Stout, M., Hou, Z., Gangjee, A., and Matherly, L. H. (2013) Therapeutic targeting malignant mesothelioma with a novel 6-substituted pyrrolo[2,3-d]pyrimidine thienoyl antifolate via its selective uptake by the proton-coupled folate transporter. *Cancer Chemother Pharmacol* 71, 999-1011
63. Golani, L. K., Wallace-Povirk, A., Deis, S. M., Wong, J. E., Ke, J., Gu, X., Raghavan, S., Wilson, M. R., Li, X., Polin, L., de Waal, P. W., White, K., Kushner, J., O'Connor, C., Hou, Z., Xu, H. E., Melcher, K., Dann, C. E., Matherly, L. H., and Gangjee, A. (2016) Tumor Targeting with Novel 6-Substituted Pyrrolo [2,3-d] Pyrimidine Antifolates with Heteroatom Bridge Substitutions Via Cellular Uptake by Folate Receptor α and the Proton-coupled Folate Transporter and Inhibition of De Novo Purine Nucleotide Biosynthesis. *Journal of medicinal chemistry* 59, 7856-7876
64. Ravindra, M. P., Wilson, M. R., Tong, N., O'Connor, C., Karim, M. A., Polin, L., Wallace-Povirk, A., White, K., Kushner, J., Hou, Z., Matherly, L. H., and Gangjee, A. (2018) Fluorinated Substituted Pyrrolo[2,3-d]Pyrimidine Antifolates With Tumor-Targeting Via Cellular Uptake by Folate Receptor α and the Proton-coupled Folate Transporter and Inhibition of De Novo Purine Nucleotide Biosynthesis. *Journal of medicinal chemistry*
65. Wang, L., Cherian, C., Desmoulin, S. K., Polin, L., Deng, Y., Wu, J., Hou, Z., White, K., Kushner, J., Matherly, L. H., and Gangjee, A. (2010) Synthesis and antitumor activity of a novel series of 6-substituted pyrrolo[2,3-d]pyrimidine thienoyl antifolate inhibitors of purine biosynthesis with selectivity for high affinity folate receptors and the proton-coupled folate transporter over the reduced folate carrier for cellular entry. *J Med Chem* 53, 1306-1318
66. Wang, L., Desmoulin, S. K., Cherian, C., Polin, L., White, K., Kushner, J., Fulterer, A., Chang, M.-H., Mitchell, S., Stout, M., Romero, M. F., Hou, Z., Matherly, L. H., and Gangjee, A. (2011) Synthesis, biological and antitumor activity of a highly potent 6-substituted pyrrolo[2,3-d]pyrimidine thienoyl antifolate inhibitor with proton-coupled folate transporter and folate receptor selectivity over the reduced folate carrier that inhibits β-glycinamide ribonucleotide formyltransferase. *Journal of medicinal chemistry* 54, 7150-7164
67. Wang, L., Wallace, A., Raghavan, S., Deis, S. M., Wilson, M. R., Yang, S., Polin, L., White, K., Kushner, J., Orr, S., George, C., O'Connor, C., Hou, Z., Mitchell-Ryan, S., Dann, C. E., Matherly, L. H., and Gangjee, A. (2015) 6-Substituted Pyrrolo[2,3-d]pyrimidine Thienoyl Regioisomers as Targeted Antifolates for Folate Receptor α and the Proton-Coupled Folate Transporter in Human Tumors. *Journal of medicinal chemistry* 58, 6938-6959
68. Varela-Moreiras, G., and Selhub, J. (1992) Long-term folate deficiency alters folate content and distribution differentially in rat tissues. *J Nutr* 122, 986-991
69. Kotake, Y., Iijima, A., Yoshimatsu, K., Tamai, N., Ozawa, Y., Koyanagi, N., Kitoh, K., and Nomura, H. (1994) Synthesis and Antitumor Activities of Novel 6-5 Fused Ring Heterocycle Antifolates: N-[4-[.omega.-(2-Amino-4-substituted-6,7-dihydrocyclopenta[d]pyrimidin-5-yl)alkyl]benzoyl]-L-glutamic Acids. *J. Med. Chem.* 37, 1616-1624
70. Gangjee, A., Li, W., Yang, J., and Kisliuk, R. L. (2008) Design, Synthesis, and Biological Evaluation of Classical and Nonclassical 2-Amino-4-oxo-5-substituted-6-methyl-pyrrolo[3,2-d]pyrimidines as Dual Thymidylate Synthase and Dihydrofolate Reductase Inhibitors. *J. Med. Chem.* 51, 68-76
71. Guan, Y., López-Alberca, M. P., Lu, Z., Zhang, Y., Desai, A. A., Patwardhan, A. P., Dai, Y., Vetticatt, M. J., and Wulff, W. D. (2014) Catalytic Asymmetric Synthesis of Alkynyl Aziridines: Both Enantiomers of cis-Aziridines from One Enantiomer of the Catalyst. *Chemistry—A European Journal* 20, 13894-13900
72. Gangjee, A., Zeng, Y., McGuire, J. J., Mehraein, F., and Kisliuk, R. L. (2004) Synthesis of Classical, Three-Carbon-Bridged 5-Substituted Furo[2,3-d]pyrimidine and 6-Substituted Pyrrolo[2,3-d]pyrimidine Analogues as Antifolates. *J. Med. Chem.* 47, 6893-6901
73. Rondla, N. R., Levi, S. M., Ryss, J. M., Vanden Berg, R. A., and Douglas, C. J. (2011) Palladium-Catalyzed C—CN Activation for Intramolecular Cyanoesterification of Alkynes. *Organic Letters* 13, 1940-1943
74. de Leseleuc, M., and Collins, S. K. (2015) Direct synthesis of macrodiolides via hafnium(iv) catalysis. *Chemical Communications* 51, 10471-10474
75. Golani, L. K., George, C., Zhao, S., Raghavan, S., Orr, S., Wallace, A., Wilson, M. R., Hou, Z., Matherly, L. H., and Gangjee, A. (2014) Structure—Activity Profiles of Novel 6-Substituted Pyrrolo[2,3-d]pyrimidine Thienoyl Antifolates with Modified Amino Acids for Cellular Uptake by Folate Receptors α and β and the Proton-Coupled Folate Transporter. *J. Med. Chem.* 57, 8152-8166
76. Cheong, C. G.; Wolan, D. W.; Greasley, S. E.; Horton, P. A.; Beardsley, G. P.; Wilson, I. A., Crystal structures of human bifunctional enzyme aminoimidazole-4-carboxamide ribonucleotide transformylase/IMP cyclohydrolase in complex with potent sulfonyl-containing antifolates. *J Biol Chem* 2004, 279 (17), 18034-45.
77. Deis, S. M.; Doshi, A.; Hou, Z.; Matherly, L. H.; Gangjee, A.; Dann, C. E., 3rd, Structural and Enzymatic Analysis of Tumor-Targeted Antifolates That Inhibit Glycinamide Ribonucleotide Formyltransferase. *Biochemistry* 2016, 55 (32), 4574-82.

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

What is claimed is:

1. A method of treating a patient having cancer comprising administering a therapeutically effective amount of a compound of Formula I, and optionally a pharmaceutically acceptable salt thereof:

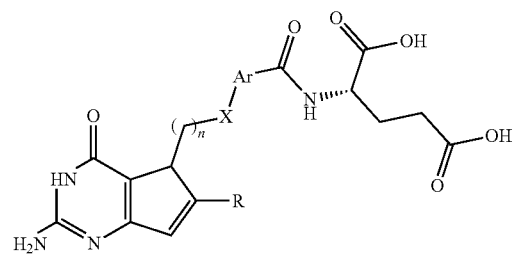

Formula I,
wherein,
R is one selected from the group consisting of H and $CH_3$;
n is an integer ranging from 3 to 4 when X is —$CH_2$— and Ar is 1,4-phenyl, or n is an integer ranging from 1 to 4 when X is —$CH_2$— and Ar is either 2'-fluoro-1,4-phenyl or 2,5-thienyl, or n is an integer ranging from 1 to 4 when X is one selected from the group consisting of O, S, —NH—, —NHCHO—, —NHCOCH$_3$—, and —NHCOCF$_3$— and Ar is one selected from the group consisting of (a) 1,4-phenyl, (b) 2'-fluoro-1,4-phenyl, and (c) 2,5-thienyl, wherein said cancer is selected from the group consisting of non-small cell lung cancer, pancreatic cancer, ovarian cancer, and colon cancer.

* * * * *